(12) United States Patent
Yaksh et al.

(10) Patent No.: US 6,573,282 B1
(45) Date of Patent: Jun. 3, 2003

(54) PERIPHERALLY ACTIVE ANTI-HYPERALGESIC OPIATES

(75) Inventors: Tony L. Yaksh, San Diego, CA (US); Alan L. Maycock, Malvern, PA (US)

(73) Assignees: Adolor Corporation, Malvern, PA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/374,634

(22) Filed: Aug. 16, 1999

Related U.S. Application Data

(63) Continuation-in-part of application No. 09/199,873, filed on Nov. 24, 1998, now Pat. No. 6,166,039, which is a continuation of application No. 08/712,881, filed on Sep. 12, 1996, now Pat. No. 5,994,372, which is a continuation-in-part of application No. 08/528,510, filed on Sep. 12, 1995, now Pat. No. 5,849,761.

(51) Int. Cl.⁷ ............................................. A61K 31/451
(52) U.S. Cl. .................................................... 514/330
(58) Field of Search ................................. 514/327, 330

(56) References Cited

U.S. PATENT DOCUMENTS

| | | | |
|---|---|---|---|
| 3,275,510 A | 9/1966 | Magid et al. ................... 167/58 |
| 3,714,159 A | 1/1973 | Jansssen et al. .......... 260/247.1 |
| 3,789,072 A | 1/1974 | Bernstein ................. 260/557 B |
| 3,884,916 A | 5/1975 | Janssen et al. ............ 260/247.7 |
| 3,914,238 A | 10/1975 | Soudijn et al. ........ 260/293.58 |
| 3,950,537 A | 4/1976 | DeBenneville et al. ..... 424/322 |
| 3,996,214 A | 12/1976 | Dajani et al. ................. 260/240 |
| 3,998,832 A | 12/1976 | Adelstein et al. ....... 260/293.54 |
| 4,012,374 A | 3/1977 | Wade et al. ............... 260/239.3 |
| 4,012,393 A | 3/1977 | Markos et al. .......... 260/293.54 |
| 4,013,668 A | 3/1977 | Adelstein et al. ....... 260/293.54 |
| 4,025,652 A | 5/1977 | Diamond et al. ............ 424/322 |
| 4,057,549 A | 11/1977 | Adelstein et al. ....... 260/293.54 |
| 4,060,635 A | 11/1977 | Diamond et al. ............ 424/322 |
| 4,066,654 A | 1/1978 | Adelstein et al. ....... 260/293.69 |
| 4,069,223 A | 1/1978 | Adelstein et al. ....... 260/293.76 |
| 4,072,686 A | 2/1978 | Adelstein et al. ....... 260/293.69 |
| 4,115,564 A | 9/1978 | Diamond et al. ............ 424/244 |
| 4,116,963 A | 9/1978 | Adelstein et al. ....... 260/293.69 |
| 4,125,531 A | 11/1978 | Yen ............................ 546/133 |
| 4,147,804 A | 4/1979 | Diamond et al. ............ 424/322 |
| 4,160,099 A | 7/1979 | Bodor ......................... 560/110 |
| 4,194,045 A | 3/1980 | Adelstein .................... 546/209 |
| 4,203,920 A | 5/1980 | Diamond et al. ....... 260/553 A |
| 4,218,454 A | 8/1980 | DeGraw et al. ............. 424/260 |
| 4,238,390 A | 12/1980 | Meienhofer et al. ..... 260/112.5 |
| 4,269,843 A | 5/1981 | DeGraw et al. ............. 424/260 |
| 4,277,605 A | 7/1981 | Buyniski et al. ............. 546/74 |
| 4,326,074 A | 4/1982 | Diamond et al. .............. 564/47 |
| 4,326,075 A | 4/1982 | Diamond et al. .............. 546/48 |
| 4,328,803 A | 5/1982 | Pape ............................ 128/276 |
| 4,371,463 A | 2/1983 | Pert et al. .............. 260/112.5 E |
| 4,384,000 A | 5/1983 | Lanier .......................... 424/267 |
| 4,407,794 A | 10/1983 | Roques et al. ............... 424/177 |
| 4,416,886 A | 11/1983 | Bernstein .................... 424/260 |
| 4,430,327 A | 2/1984 | Frederickson ............... 424/177 |
| 4,493,848 A | 1/1985 | LaHann et al. .............. 424/324 |
| 4,517,295 A | 5/1985 | Bracke et al. ............... 435/101 |
| 4,533,739 A | 8/1985 | Pitzele et al. ................ 548/559 |

(List continued on next page.)

FOREIGN PATENT DOCUMENTS

| | | |
|---|---|---|
| EP | 0127154 | 5/1984 |
| EP | 171742 A2 | 8/1985 |
| EP | 325406 A3 | 1/1989 |
| EP | 325406 A2 | 1/1989 |
| EP | 325406 B1 | 1/1989 |
| EP | 351897 A3 | 6/1989 |
| EP | 351897 A2 | 6/1989 |
| EP | 0363635 | 9/1989 |
| EP | 0350221 | 1/1990 |
| EP | 0383635 | 8/1990 |
| EP | 512902 A1 | 4/1992 |
| EP | 0544391 | 8/1992 |
| EP | 0582727 | 2/1994 |
| EP | 0640596 | 3/1995 |
| FR | 2100711 | 3/1972 |
| GB | 2169292 | 7/1986 |
| GB | 2287404 | 9/1995 |
| WO | 9102497 | 3/1991 |
| WO | 9202223 | 8/1991 |
| WO | 9213540 | 8/1992 |
| WO | 9316707 | 9/1993 |
| WO | 9527510 | 10/1995 |
| WO | 9709973 | 3/1997 |
| WO | 9732857 | 9/1997 |
| WO | 9733634 | 9/1997 |
| WO | 9827985 | 7/1998 |
| WO | 9842275 | 10/1998 |

OTHER PUBLICATIONS

Abbott, "Peripheral and central antinociceptive actions of ethylketocyclazocine in the formalin test." *Eur. J. Pharmacol.* 142:93–100 (1988).

Acne in Teens: Ways to Control it, AAFP patient education brochure series, Health Notes from Your Family Doctor, (1994).

Adelstein, Gilbert W., et al., "3,3–Diphenyl–3–(2–alkyl–1,3,4–oxadiazol–5–yl)propylcycloalkylamines, a Novel Series of Antidiarrheal Agents,"*J. Med. Chem.* 19:1221–1225, (1976).

(List continued on next page.)

*Primary Examiner*—Phyllis G. Spivack
(74) *Attorney, Agent, or Firm*—Stephanie L. Seidman; Heller Ehrman White & McAuliffe, LLP.

(57) ABSTRACT

Compositions and methods using the compositions for treatment of peripheral hyperalgesia are provided. The compositions contain an anti-hyperalgesia effective amount of one or more compounds that directly or indirectly interact with peripheral opiate receptors, but that do not, upon topical or local administration, elicit substantial central nervous system effects. The anti-diarrheal compound 4-(p-chlorophenyl)-4-hydroxy-N-N-dimethyl-$\alpha,\alpha$-diphenyl-1-piperidinebutyramide hydrochloride is preferred for use in the compositions and methods.

39 Claims, 5 Drawing Sheets

U.S. PATENT DOCUMENTS

| | | | |
|---|---|---|---|
| 4,626,539 A | 12/1986 | Ayngst et al. | 514/282 |
| 4,749,706 A | 6/1988 | Lawson et al. | 514/282 |
| 4,824,853 A | 4/1989 | Wals et al. | 514/327 |
| 4,867,979 A | 9/1989 | Sheth et al. | 424/195.1 |
| 4,870,084 A | 9/1989 | Eggler et al. | 514/320 |
| 4,871,750 A | 10/1989 | Roberts | 514/328 |
| 4,892,735 A | 1/1990 | Harrap | 424/435 |
| 4,897,260 A | 1/1990 | Ross et al. | 424/59 |
| 4,898,873 A | 2/1990 | Wals et al. | 514/327 |
| 4,917,896 A | 4/1990 | Peck et al. | 424/449 |
| 4,939,142 A | 7/1990 | Budai et al. | 514/238 |
| 4,990,521 A | 2/1991 | Van Daele et al. | 514/327 |
| 5,039,642 A | 8/1991 | Chrobaczek | 502/155 |
| 5,069,909 A | 12/1991 | Sharma et al. | 424/449 |
| 5,100,903 A | 3/1992 | Lalinde et al. | 514/327 |
| 5,109,135 A | 4/1992 | D'Ambra et al. | 544/73 |
| 5,112,596 A | 5/1992 | Malfroy-Camine | 424/2 |
| 5,116,847 A | 5/1992 | Gilbert et al. | 514/327 |
| 5,116,868 A | 5/1992 | Chen et al. | 514/546 |
| 5,143,938 A | 9/1992 | Calvet et al. | 514/653 |
| 5,149,538 A | 9/1992 | Granger et al. | 424/449 |
| 5,202,130 A | 4/1993 | Grant et al. | 424/617 |
| 5,214,080 A | 5/1993 | Iwamura et al. | 523/336 |
| 5,229,127 A | 7/1993 | McKinzie | 424/427 |
| 5,236,947 A | 8/1993 | Calvet et al. | 514/433 |
| 5,240,932 A | 8/1993 | Morimoto et al. | 514/282 |
| 5,242,944 A | 9/1993 | Park et al. | 514/466 |
| 5,248,505 A | 9/1993 | Garwin | 424/472 |
| 5,266,465 A | 11/1993 | Rubin et al. | 435/69.2 |
| 5,273,056 A | 12/1993 | McLaughlin et al. | 128/898 |
| 5,273,751 A | 12/1993 | Dubroff | 424/427 |
| 5,278,126 A | 1/1994 | Katqno et al. | 503/201 |
| 5,282,851 A | 2/1994 | Jacob-LaBarre | 623/6 |
| 5,286,751 A | 2/1994 | Sunshine et al. | 514/570 |
| 5,292,362 A | 3/1994 | Bass et al. | 106/124 |
| 5,300,648 A | 4/1994 | Emonds-Alt et al. | 546/193 |
| 5,312,899 A | 5/1994 | Schiller | 530/331 |
| 5,345,943 A | 9/1994 | Hargreaves et al. | 128/742 |
| 5,354,863 A | 10/1994 | Dappen et al. | 546/35 |
| 5,366,979 A | 11/1994 | Lawson | 514/282 |
| 5,369,131 A | 11/1994 | Poli et al. | 514/772.4 |
| 5,384,124 A | 1/1995 | Courteille et al. | 424/430 |
| 5,387,688 A | 2/1995 | Feldman et al. | 546/223 |
| 5,403,867 A | 4/1995 | Okumura et al. | 514/573 |
| 5,432,176 A | 7/1995 | Walser | 514/252 |
| 5,434,292 A | 7/1995 | Saita et al. | 560/51 |
| 5,436,009 A | 7/1995 | Jauw et al. | 424/436 |
| 5,437,994 A | 8/1995 | Emerson et al. | 435/240.2 |
| 5,446,052 A | 8/1995 | Emonds-Alt et al. | 514/318 |
| 5,446,070 A | 8/1995 | Mantelle | 514/772.6 |
| 5,466,821 A | 11/1995 | Worthington | 424/449 |
| 5,478,814 A | 12/1995 | Packman | 514/53 |
| 5,589,480 A | 12/1996 | Elkhoury et al. | 514/282 |
| 5,618,557 A | 4/1997 | Wille et al. | 424/449 |
| 5,645,854 A | 7/1997 | Masiz | 424/449 |
| 5,646,151 A | 7/1997 | Kruse et al. | 514/255 |
| 5,667,773 A | 9/1997 | Farrar et al. | 424/78.05 |
| 5,686,106 A | 11/1997 | Kelm et al. | 424/463 |
| 5,688,955 A | 11/1997 | Kruse et al. | 546/276.4 |
| 5,744,458 A | 4/1998 | Kruse et al. | 514/91 |
| 5,760,023 A | 6/1998 | Farrar et al. | 514/150 |
| 5,763,445 A | 6/1998 | Kruse et al. | 514/255 |
| 5,798,093 A | 8/1998 | Farrar et al. | 424/45 |
| 5,811,078 A | 9/1998 | Maycock et al. | 424/45 |
| 5,834,480 A | 11/1998 | Elkhoury | 514/289 |
| 5,849,761 A | 12/1998 | Yaksh | 514/327 |
| 5,849,762 A | 12/1998 | Farrar et al. | 514/327 |
| 5,855,907 A | 1/1999 | Peyman | 424/434 |
| 5,866,143 A | 2/1999 | Elkhoury | 424/401 |
| 5,869,521 A | 2/1999 | Farrar et al. | 514/422 |
| 5,888,494 A | 3/1999 | Farrar et al. | 424/78.5 |
| 5,919,473 A | 7/1999 | Elkhoury | 424/423 |
| 5,945,443 A | 8/1999 | Kruse et al. | 514/429 |
| 5,962,477 A | 10/1999 | Mak | 514/327 |
| 5,981,513 A | 11/1999 | Kruse et al. | 514/91 |
| 5,994,372 A | 11/1999 | Yaksh et al. | 514/327 |
| 6,166,039 A | 12/2000 | Yaksh | 514/327 |
| 6,190,691 B1 | 2/2001 | Mak | 424/449 |

OTHER PUBLICATIONS

Alreja, et al., The formalin test: A tonic pain model in the primate, *Pain*, 20:97–105 (1984).

Andreev et al., "Opoids suppress spontaneous activity of polymodal nociceptors in rat paw skin induced by ultraviolet radiation." *Neuroscience* 58(4):793–798 (1994).

Ansel et al., "Cytokine modulation of keratinocyte cytokines", *J. of Inv. Derm.* 94(6):101–107 (1990).

Antonijevic, et al., Perineurial defect and peripheral opioid analgesia in inflammation, *J. Neurosci.*, 15(1):165–172 (1995).

Atwouters, et al., "Loperamide: Survey of studies on mechanism of its antidiarrheal activity," *Dig. Dis. and Sci.* 38(6):977–995, (1993).

Atwouters et al., "Pharmacology of antidiarrheal drugs." *Ann. Rev. Pharmacol. Toxicol.* 23:279–301 (1983).

Bergfeld, et al., The evaluation and management of acne: Economic considerations, *J. Am. Acad. Dermatol.* 32(5)S52–56 (1995).

Berrebi et al., "Verapamil inhibits B–cell proliferation and tumor necrosis factor release and induces a clinical response in B–cell chronic lymphocytic leukemia", *Leukemia* 8(12):2214–2216 (1994).

Berson, et al., The treatment of acne: The role of combination therapies, *J. Am. Acad. Dermatol.* 32:S31–41 (1995).

Bianchi and Goi, "On the antidiarrheal and analgesic properties of diphenoxylate, difenoxine and loperamide in mice and rates." *Arzeneimittel–Forschung/Drug Research* 27(*1*), 5,1040–1043 (1977).

Buerkle et al., "Comparison of the spinal actions of the $\mu$–opioid remifentanil with alfentanil and morphine in the rat", *Anesthesiology* 84(1):94–102 (1996).

Burkhardt et al., "Metkephamid (Tyr–D–Ala–Gly–Phe–N–(Me)Met–NH$_2$), a potent opoid peptide: Receptor binding and analgesic properties." *Peptides* 3:869–871 (1982).

Chemical Abstr. 100:17470j (1984), citing Iizuka et al., "Pharmacodynamics of a new antidiarrheic nufenoxole", *Jitchuken Zenrinsho Kenkyho* 9 (*1*): 19–41 (1983).

Chemical Abstr. 105.208764w (1986), citing DE 3,545,981 (Jul. 10, 1986).

Chemical Abstr. 111:17521d (1989), citing Shaw et al., "ICI 204448: A κ–opoid agonist with limited access to the CNS", *Br. J. Pharmacol.* 96(*4*):986–992 (1989).

Chemical Abstr. 118:124404j (1993), citing EP 512,902, (May 3, 1991).

Chemical Abstr. 120:116860f (1994), citing Japanese patent JP 05,286,851 (Nov. 2, 1993).

Chemical Abstr. 120:289632 (1994), citing Park et al., "Pain reducing effects of 4–amino and 4–(1–piperazinyl)phenacetamide derivatives", *Korean J. Med. Chem.* 3(*2*): 116–123 (1993).

Chemical Abstr. 121:57079d (1994), citing Park et al., "Synthesis of caspicinoids: 3–nitrogen–substituted phenylacetamides", *Korean J. Med. Chem.* 3(*2*): 142–147 (1993).

Chemical Abstr. 123:22673g, citing Park et al., KR–25003, "a potent analgesic capsaicinoid", *Acta Crystallogr. Sect. C: Cryst. Struct. Comm.* C51(5): 927–929 (1995).

Chemical Abstr. 123:256289p, citing Lee et al., "Synthesis of phenylacetamides and their analgesic activities", *Korean J. Med. Chem.* 5(1): 6–12 (1995).

Chemical Abstr. 80:82443k (1974), citing U.S. 3,789,072.

Chemical Abstr. 82:156117x (1975), citing Ger. Offen. DE 2,440,541, (Mar. 6, 1975).

Chemical Abstr. 84: 44072p (1976), citing Ger. Offen. DE 2,514,229, (Oct. 9, 1975).

Chemcial Abstr. 84:44071n (1976), citing Ger. Offen. DE 2,514,183 (Oct. 9, 1975).

Chemical Abstr. 84:44072p (1976), citing Ger. Offen. DE 2,514,229 (Oct. 9, 1975).

Chemical Abstr. 85:116541m, citing Adelstein et al., "3,3–Diphenyl–3–(2–alkyl–1,3, 4–oxadiazol–5–yl)propylcycloalkylamines, a novel series of antidiarrheal agents", *J. Med. Chem* 19(10): 1221–1225 (1976).

Chemical Abstr. 96:20297n (1982), citing Belgian Patent BE 886,579 (Jun. 10, 1981).

Cortes, et al., Tape stripping–induced hyperalgesia as a model for the evaluation of analgesic agents, *Soc. Neurosci. Abstr.*, 22:1315 (1996).

Craft, R.M., et al., "Opioid Antiociception in a Rat Model of Visceral Pain: Systemic Versus Local Drug Adminstration," 275:1535–1542, (1995).

D'Amour et al., "A method for determining loss of pain sensation." *J. Pharmacol. Exp. Ther.* 72:74 (1941).

Dajani et al., "Effects of E prostaglandins, diphenoxylate and morphine on intestinal motility in vivo." *Eur. J. Pharmacol.* 34: 105–113 (1975).

Dajani et al., "The pharmacology of SC–27166: A novel antidiarrheal agent." *J. Pharmacol. Exp. Ther.* 203: 512–526 (1977).

Dashwood et al., "Autoradiographic demonstration of [$^3$H] loperamide binding to opoid receptors in rat and human small intestine." *The International Narcotics Reserach Conference (INRC) '89*, Alan R. Liss, Inc., pp. 165–169 (1990).

Database, Derwent Publication 199236, citing patent # 9213540, Analgesic ointment contg. cocaine or novocaine— together with menthol and salicylate ester.

DeHaven–Hydkins et al., ADL 2–1294, a peripherally selective opiate analgesic, *Society for Neuroscience Abstracts* 22(1–3): 1362 (1996).

Dickenson, Neurophysiology of opioid poorly responsive pain, *Cancer Surveys* 21:5–16 (1994).

Dixon, The up–and–down method for small samples, *Am. Stat. Assoc. J.* 60:967–978 (1965).

Dubner et al., "Spinal dorsal horn plasticity following tissue or nerve injury." Ion, *Textbook of Pain*, Melzack et al., eds., Churchill–Livingstone, London, pp. 225–242 (1994).

Dubuisson, et al., The formalin test: A quantitative study of the analgesic effects of morphine, meperidine, and brain stem stimulation in rats and cats, *Pain*, 4:161–174 (1977).

Eddy, et al., Synthetic Analgesics. II. Dthienylbutenyl– And Dithienylbutylamines, *J. Pharmacol Exptl. Therap.* 107: 385 (1953).

Enk et al., "Early molecular events in the induction phase of contact sensitivity", *Proc. Natl. Acad. Sci USA* 89:1398–1402 (1992).

Ercoli et al., "I. The Time–Action Curves of Morphine, Codeine, Dilaudid and Drmerol by Various Methods of Administration. II. Analgesic Activity of Acetylsalicylic Acid and Aminopyrine." *J. Pharmacol. Exptl. Therap.* 84:301 (1945).

Ferreira et al., "Prostaglandin hyperalogesia: The peripheral analgesic activity of morphine, enkephalins and opioid antagonists." *Prostaglandins* 73:191–200 (1979).

Frederickson, "Animal and human analgesic studies of metkephamid." *Advanced in Pain Research and Therapy*, vol. 8, Foley and Inturrsi, Eds., Raven Press, New York pp. 293–301 (1986).

Frederickson et al., "Metkephamid, a systemically active analogue of methionine enkephalin with potent opioid δ–receptor activity." *Science* 211:603–605 (1981).

Gamse, "Capsaicin and nociception in the rat and mouse." *Naunyn–Schmiedeberg's Arch. Pharmacol.* 320:205–216 (1982).

Gasbarrini, G., et al., "Multicenter Double–blinded Controlled Trial Comparing idamidine HC1 and Loperamide in the Symptomatic Treatment Acute Diarrhoea," *Drug Res.* 36:1843–1845.

Gesellchen et al., "Structure–activity relationships of enkephalin analogs." *Peptides: Synthesis, structure, function and processing. American Peptide Symposium, 7th*, Rich and Gross, Eds., Pierce Chemical Co., Rockford, III. pp. 621–624 (1981).

Giagnoni et al., "Loperamide: Evidence of interaction with $\mu$ and δ opid receptors." *Life Sci.* 33(Suppl. 1):315–318 (1983).

Giardina, et al., Central and peripheral analgesic agents: chemical strategies for limiting brain penetration in kappa–opioid agonists belonging to different chemical classes, *II Farmaco* 50(6):405–18 (1995).

Goodman et al., *The pharmacological basis for therapeutics*, McMillian, New York, NY, pp. 505–517 (1985).

Gottschlich et al., "The peripherally acting K–opiate agonist EMD 61753 and analogues: opioid activity versus peripheral selectivity", *Drugs Exptl. Clin. Res.* XXI(5):171–174 (1995).

Handwerker et al., "Pain and Inflammation." *Proceedings of the VIth World Congress on Pain, Chapter 7*, Bond, et al., Eds., Elsevier Science Publishers BV, Amsterdam, pp. 59–70 (1991).

Hertz, Role of Immune Processes in Peripheral Opioid Analgesia, *The Brain Immune Axis and Substance Abuse*, Plenum Press, New York (1995).

Heykants, et al., Loperamide (R 18 553), a novel type of antidiarrheal agent, *Arzneim.–Forsch. Drug Res.*, 24:1649–1653 (1974).

Hurwitz, A., et al., "Lopermide effects on hepatobiliary function, intestinal transit and analgesia in mice," *Life Scineces*, 54:1687–1698, (1994).

IUPAC–IUB Commission on Biochemical Nomenclature Abbreviated Nomenclature of Synthetic Polypeptides (Polymerized Amino Acids), *Biochem.* 11:942–944 (1972).

Jaffe et al., "Abuse potential of loperamide." *Clin. Pharmacol. Ther.* 28(6):812–819 (1980).

James et al., "Naloxazone Treatment in the Guinea Pig Ileum in Vivo Reveals Second Functional Opioid Receptor Site." *J. Pharmacol Exp. Ther.* 240:138–144 (1987).

Kaminer, et al., The many faces of acne, *J. Am. Acad. Dermatol.* 32(5):S6–14 (1995).

Keita, Hawa, et al., "Antinociceptive effect of a κ–opioid receptor agonist that minim? Crosses the blood–brain (ICI 204448) in a rat model of mononeuropathy," *Eur. J. of Pharmacol.* 277:275–280, (1995).

Kinnman, et al., Peripherally administered morphine attenuates capsaicin–induced mechanical hypersensitivity in humans, *Anesth. Analg.* 84:595–9 (1997).

Koo, The psychosocial impact of acne: Patients' perceptions, *J. Am. Acad. Dermatol.* 32(5):S26–30 (1995).

Kosterlitz et al., *Br. J. Pharmacol.* 33:266–276 (1968).

Lee, Buyean, et al., "RK–25018: A Novel, Orally Active Analgesic with Non–narcotic Properties," *Arch. Pharm. Res.,* 17:5:304–308, (1994).

Levine et al., "Involvement of the mu–opiate receptor in peripheral analgesia." *Neurosci.* 32(3):571–575 (1989).

Mackerer et al., "Antidiarrheal and central nervous system activities of SC–277166 (2–[3–5–methyl–1,3, 4–oxadiazol–2–yl–3,3–diphenylpropyl]–2–azabicyclo [2.2.2]octane), a newantidiarrheal agent, resulting from binding to opiate receptor sites of brain and myenteric plexus." *J. Pharmocol. Exper. Ther.* 203(1):527–538 (1977).

Mackerer et al., Loperamide binding to opiate receptor sites of brain and myenteric plexus. *J. Pharmacol. Exp. Ther.* 1999:131–140 (1976).

Mackerer et al., Review of the involvement of opiate receptors in producing the central and peripheral effects carused by two new antidiarrheal drugs, loperamide and SC–27166. *J. Am. Coll. Toxicol.* 3:81–91 (1984).

Makman, Morphine receptors in imunocytes and neurons, *Advances in Neuroimmunology* 4:69–82 (1994).

Mather, Opioids: A pharmacologist's delight!, *Clinical and Experimental Pharmacology and Physiology* 22:833–36 (1995).

Megens et al., Is in vivo association between the antipropulsive and antidarrheal properties of opioids in rats related to gut selectivity? *Arch. Int. Pharmacodyn. Ther.* 298:220–229 (1989).

Megens et al., Normalization of small intestinal propulsion with loperamide–like antidiarrheals in rats. *Eur. J. Pharmacol.* 178:357–364 (1990).

Mir, G.N., et al., "In vivo antimotility and antidiarheal activity of lidamidine hydrochloride (WHR–1142A), a novel antidiarrheal agent," *Drug Res., 28:*(III), 1448–1480).

Moiniche, et al., Peripheral antinociceptive effects of morphine after burn injury, *Acta Anaesth. Scand.*, 37:710–712, 1993.

Molina et al., The peripheral analgesic effect of morphine, codeine, pentazocine and D–propoxyphene, *Brazilian J. Med. Biol. Res.* 16: 345–352 (1983).

Nagasaka et al., Peripheral and spinal actions of opioids in the blockade of the autonomic response evoked by compression of the inflamed knee joint. *Anesthesiol.* 85:808–816 (1996).

Needham, Painless lumbar surgery: morphine nerve paste, *Connecticut Medicine* 60(3):141–43 (1996).

Neugebauer et al., "N–Methyl–D–Aspartate (NMDA) and Non–NMDA Receptor Antagonists Block the Hyperexcitability of Dorsal Horn Neurons During Development of Acute Arthritis in Rat's Knee Joint." *J. Neurophysiol.* 70(4):1365–1377 (1993).

Niemegeers, et al., Difenoxine (R 15403), the Active Metabolite of Diphenoxylate (R 1132), *Arzneim.–Forsch,* 22:516–518 (1972).

Nguyen, et al., Management of acne vulgaris, *American Family Physician* 50(1):89–96 (1994).

Niemegeers et al., Dissociation between opiate–like and antidiarrheal activities of antidiarrheal drugs. *J. Pharmacol. Exp. Ther.* 203:527–538 (1979).

Niemegeers et al., Loperamide (R 18 533), a novel type of antidiarrheal agent, *Arzneim.–Forsch. (Drug Res.)* 24(10): 1633–1641 (1974).

Nogrady, *Medicinal Chemistry: A Biochemical Approach*, Oxford Univ. Press, New York, pp 388–392 (1985).

Oluyomi, et al., Differential antinociceptive effects of morphine and methylmorphine in the formalin test, *Pain*, 49:415–418 (1992).

Osborne, Richard, et al., "Analgesic Activity of Morphine–6–Glucuronide," *The Lancet*, :828, (1988).

Park, No–Sang, et al., "KR–25003, a Potent Analgesic Capsaicinoid," *Acta Crystallographica* C51:927–929 (1995).

Paul, Dennis, et al., Pharmacological Characterization of Morphine–6δ–Glucuronide, a Very Potent Morphine Metabolite[1], *The Journal of Pharmacology and Experimental Therapeutics,* 251:477–483, (1989).

Shaw, John S., "ICI 204448: a k–opioid agonist with limited access to the CNS," *Br. J. Pharmacol.* 96:986–992, (1989).

Shriver et al., "Loperamide." *Pharmacological and Biochemical Properties of Drug Substances, vol. 3*, Goldberg, Ed., American Pharmaceutical Ass'n Press pp. 461–476 (1981).

Smith et al., "Peripheral antinociceptive effects of N–methyl morphine", *Life Sciences* 31 (12 & 13): 1205–1208 (1982).

Solomon, et al., Effects of detergents on acne, *Clinics in Dermatology* 14:95–99 (1996).

Stahl et al., "Receptor affinity and pharmacological potency of a series of narcotic analgesic, anti–diarrheal and neuroleptic drugs." *Eur. J. Pharmacol.* 46:199–205 (1977).

Stein, "Peripheral analgesic actions of opioids", *J. Pain and Sympt Mgmt.* 6(3):119124 (1991).

Stein, "Peripheral analgesic actions of opioid analgesia." *Anesth. Analg.* 76:182–191 (1993).

Stein, "Peripheral opioid receptors", *Ann Med* 27:219–221 (1995).

Stein et al., "Analgesic effect of intraarticular morphine after arthroscopic knee surgery." *New Eng. J. Med.* 325(16):1123–1126 (1991).

Stein et al., "Peripheral opoid receptors mediating antinociception in inflammation. Evidence for involvement of Mu, Delta and Kappa receptors." *J. Pharmacol. Exp. Ther.* 248(3): 1269–1275 (1989).

Stein, et al., Antinociceptive effects of $\mu$–and κ–agonists in inflammation are enhanced by a peripheral opioid recetptor–specific mechanism, *European Journal of Pharmacolog* 3:255–64 (1988).

Stein, et al., No tolerance to peripheral morphine analgesia in presence of opioid expression in inflamed synovia, *J. Clin. Invest.* 98(3):793–99 (1996).

Stein, et al., Opioids as novel intra–articular agents in arthritis, *Progress in Pain Research and Management* 1:289–96 (1994).

Stein, et al., Peripheral effect of fentanyl upon nociception in inflamed tissue of the rat, *Neurosci. Lett.*, 84:225–228 (1988).

Stein, et al., Unilateral inflammation of the hindpaw in rats as a model of prolonged noxious stimulation: Alterations in behavior and nociceptive thresholds, *Pharmacol. Biochem. Behav.*, 31:445–451 (1988).

Stokbroekx et al., Synthetic antidiarrheal agents: 2,2–diphenyl–4–(4'–aryl–4'–hydroxypiperidino)butyramides, *J. Medicinal Chem.* 16(7): 782–786 (1973).

Sykes, et al., Acne: A review of optimum treatment, *Drugs* 48(1):59–70 (1994).

Peyman, et al., Effects of morphine on corneal sensitivity and epithelial wound healing: Implications for topical ophthalmic analgesia, *British Journal of Ophthalmology* 78:138–41 (1994).

Peyman et al., Effects of morphine on corneal sensitivity and epithelial wound healing: implications for topical ophthalmic analgesia, *Brit. J. Ophthalmol.* 78: 138–141 (1994).

Porreca et al., "Roles of Mu, Delta and Kappa Opioid Receptors in Spinal and Supraspinal Mediation of Gastrointestinal Transit Effects and Hot–Plate Analgesia in the Mouse." *J. Pharmacol. Exp. Ther.* 230(2):341–348 (1984).

Raja, et al., "Peripheral Mechanisms of Somatic Pain" *Anesthesiology* 68:571–590, (1988).

Randall et al., "A method for measurement of analgesic activity on inflamed tissue." *Arch. Int. Pharmacodyn.* 111(4):409–419 (1957).

Reinstein et al., "Suppression of lipopolysaccharide–stimulated release of tumor necrosis factor by adenosine: Evidence of $A_2$ receptors of kat kupffer cells", *Hepatology* 19(6):1445–1452 (1994).

Rogers, et al., GR94839, a κ–opioid agonist with limited access to the central nervous system, has antinociceptive activity, *J. Pharmacol.*, 106:783–789 (1992).

Russell et al., "Opiates inhibit the discharges of fine afferent units from inflamed knee joint of the cat." *Neurosci. Lttrs.* 76:107–112 (1987).

Sasaki, Yusuki, et al., "Synthesis and Biological Properties of Quaternized N–Methylation Analogs of D–Arg–2–Dermorphin Tetrapeptide," *Bioorganic & Medicinal Chemistry Letters*, 4:2049–2054, (1994).

Sato et al., "Changes in blood pressure and heart rate induced by movements of normal and inflamed knee joints." *Neurosci. Lett.* 52:55–60 (1984).

Sato et al., Catecholamine secretion and adrenal nerve activity in response to movements of normal and inflamed knee joints in cats, *J. Physiol.* 375: 611–624 (1986).

Schafer, et al., Inflammation Enhances peripheral μ–opioid receptor–mediated analgesia, but not μ–opioid receptor transcription in dorsal root ganglia, *Eur. J. Pharmacol.*, 279:165–169 (1995).

Schaible et al., "Afferent and spinal mechanisms of joint pain." *Pain* 55:5–54 (1993).

Schaible et al., "Effects of an experimental arthritis on the sensory properties of fine articular afferent units." *J. Neurophysiol.* 54(5):1109–1122 (1985).

Schnikel, et al., P–Glycogprotein in the blood–brain barrier of mice influences the brain penetration and pharmacological activity of many drugs, *Br. J. Clin. Invest.*, 97:2517–2524 (1996).

Takasuna et al., "Opoid pharmacology of the antinociceptive effects of loperamide in mice." *Behav. Pharmacol.* 5:189–195 (1994).

Tallarida et al., *Manual of Pharmacologic Calculations with Computer Programs*, 2nd Ed., New York, Springer–Verlag, pp. 7–18, (1986).

Thompson, D., et al., "Local Analgesia with Opioid Drugs", *The Annals of Pharmacotherapy*, 29:189–190, (1995).

Tjolsen et al., The formalin test: an evalution of the method, *Pain*, 51:5–17 (1992).

Traynor, Critique: Opioid receptors and their subtypes: focus on peripheral isolated tissue preparations, *Neurochem. Int.* 24(5):427–32 (1994).

van Joost et al., "Cyclosporine in atopic dermatitis", *J. Amer Acad of Derm.* 27(6):922–928 (1992).

Van der Kooy, Hyperalgesic functions of peripheral opiate receptors. *Ann. N.Y. Acad. Sci.* 467:154–168 (1986).

Wheeler–Aceto et al., Characterization of nociception and edema after formalin–induced tissue injury in the rat: Pharmacological analysis of opioid activity, *UMI Dissertaion Services* pp. 321–336; 398–406, (1995).

Williams et al., "CD28–stimulated IL–2 gene expression in Jurkat T cells occurs in part transcriptionally and is cyclosporine–A sensitive[1]", *J. of Immun.* 148:2609–2616 (1992).

Williamson et al., "Reflex increase in blood pressure induced by leg compression in man." *J. Physiol.* 475(2):351–357 (1994).

Winter et al., "Nociceptive thresholds as affected by parenteral administration of irritants and of various antinociceptive drugs." *J. Pharm. Exp. Ther.* 148(3):373 (1965).

Woolf et al., "Preemptive Analgesia—Treating Postoperative Pain by Preventing the Establishment of Central Sensitization." *Anesth. Analg.* 77:362–79 (1993).

Woolf et al., "The induction and maintenance of central sensitization is dependent on N–methyl–D–aspartic acid receptor activiation; implications for the treatment of post–injury pain hypersensitivity states." *Pain* 44:293–299 (1991).

Woolfe et al., The Evaluation of the Analgesic Action of Pethidine Hydrochloride (Demerol) *J. Pharmacol. Exptl. Exptl. Therap.*, 80:300.

Wuster, Michael, et al., "Opiate Agonist Action of Antidiarrheal Agents in vitro and in vivo—Findings in Support for Selective Action," *Archives of Pharmacology*, 301:187–194, (1978).

Yaksh, "Multiple opioid receptor systems in brain and spinal cord: Part 2" *European Journal of Anaesthesiology*, 1:201–243, (1984).

Yaksh, "Multiple opioid receptor systems in brain and spinal cord: Part I." *Eur. J. Anaesthesiol.* 1:171–199 (1984).

Yaksh, "The spinal actions of opoids." *Handbook of Experimental Pharmacology, vol. 104/II Opoids II, Chapter 33*, Herz, Ed., Springer–Verlag, Berlin and Heidelberg, pp. 53–90 (1993).

Yaksh, "The spinal pharmacology of facilitation of afferent processing evoked by high–threshold afferent input of the postinjury pain state." Current Opinion in Neurology and Neurosurgery, *Current Science* 6:250–256 (1993).

Yaksh et al., "Brief Communication. Chronic Catheterization of the Spinal Subarachnoid Space." *Physiol. Behav.* 17:1031–1036 (1976).

Yaksh et al., "Sites of action of opiates in production of analgesia." In, *Progress in Brain Research, vol. 77,.* Chap. 28, Elsevier Science Pub., B.V., pp. 371–94 (1988).

Zerbe et al., "A new Met–enkalphin analogue suppresses plasma vasopressin in man." *Peptides* 1:199–201 (1982).

PERIPHERALLY ACTIVE ANTI-HYPERALGESIC OPIATES

RELATED APPLICATIONS

This application is a continuation of allowed U.S. application Ser. No. 08/712,881, filed Sep. 12, 1996, now U.S. Pat. No. 5,994,372 Tony Yaksh, entitled "PERIPHERALLY ACTIVE ANTI-HYPERALGESIC OPIATES". This application is also a continuation-in-part of U.S. application Ser. No. 08/528,510, filed Sep. 12, 1995, now U.S. Pat. No. 5,849,761 to Tony Yaksh, entitled "PERIPHERALLY ACTIVE ANTI-HYPERALGESIC OPIATES". This application is also a continuation-in-part of U.S. application Ser. No. 09/199,873, filed Nov. 24, 1998; now U.S. Pat. No. 6,166,039 to Tony Yaksh, entitled "PERIPHERALLY ACTIVE ANTI-HYPERALGESIC OPIATES". U.S. application Ser. No. 09/199,873 is a continuation of U.S. application Ser. No. 08/528,510.

The subject matter of each of U.S. application Ser. Nos. 08/528,510, 08/712,881 and 09/199,873 is herein incorported in its entirety by reference. All patents, copending applications and publications referred to herein are, unless noted otherwise, incorporated by reference in their entirety.

FIELD OF THE INVENTION

The present invention relates to compositions and methods for treatment and/or prevention of hyperalgesic states. The compositions, which are formulated for topical and local administration, contain anti-hyperalgesics that are substantially devoid of central nervous system effects, and, thus, have very little, if any, potential for abuse.

BACKGROUND OF THE INVENTION

Pain and Analgesia

Pain has been defined in a variety of ways. For example, pain can be defined as the perception by a subject of noxious stimuli that produces a withdrawal reaction by the subject. The most commonly experienced form of pain may be defined as the effect of a stimulus on nerve endings, which results in the transmission of impulses to the cerebrum. This somatic sensation and normal function of pain, referred to as nociception or nociceptive pain, informs the organism of impending tissue damage. Somatic and visceral free nerve endings, termed nociceptors, initially process such pain signals.

Despite numerous definitions, the brain pathways governing the perception of pain are not completely understood. Sensory afferent synaptic connections to the spinal cord, so-called "nociceptive pathways", however, have been documented in some detail. The nociceptive pathway, which exists for protection of the organism (such as the pain experienced in response to a burn), is inactive. Activity is initiated by the application of a high intensity, potentially damaging stimulus. This stimulus serves to depolarize certain classes of afferent (sensory) axons of the small unmyelinated category, designed C fibers.

The signal carried by the C fibers travels up the peripheral nerve and into the spinal cord where synapses are made on second order and higher order neurons, which then transmit the pain signal up the spinal cord in the spinothalamic tract ending in the thalamus. Polysynaptic junctions in the dorsal horn of the spinal cord are involved in the relay and modulation of sensations of pain to various regions of the brain, including the periaqueductal grey region. The ventrolateral and ventromedial thalamic nuclei project to the cortex where the pain is then processed with regard to localization and other integrative characteristics.

Opioid Analgesia

Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C-fiber terminal and which, when they fire, inhibit release of substance P from the C-fiber. Descending pathways from the brain are also inhibitory to C-fiber firing. Thus, CNS-mediated analgesia leads to an overall inhibition of the pain transmission.

Agents that selectively block an animal's response to a strong stimulus without obtunding general behavior or motor function is referred to as an analgesic. Opiates, via interaction with specific receptors in the brain and spinal cord, are able to block the release of transmitters from central terminals (Yaksh et al. (1988) In: *Progress in Brain Research, Vol.* 77, Chapter 28, Elsevier Science Pub., B. V. pp. 371–94]). They are thus able to increase the intensity of the peripheral stimulus necessary to produce a given pain state. Accordingly, these agents are referred to as analgesics.

Opiate Receptors and Opiate Side Effects

Central opiate receptors (in brain and spinal cord) appear to mediate the effects of systemically administered opiates. Three principal classes of opiate receptors have been identified: $\mu$, $\kappa$ and $\delta$ (Yaksh, T. L.: *Eur. J. Anaesthesiol.* 1:201–243, 1984). The use of selective agonists and antagonists have demonstrated that these receptors also appear to mediate peripheral opioid effects. The central and peripheral actions activities of opiates are an important component of their therapeutic utility. It appears that after systemic delivery of opiates such as morphine, the primary effect may be mediated by both sites of action.

On the other hand, many of the principal drawbacks of systemic opiates are the results of their actions within the brain. These actions include sedation, depression of respiration, constipation, nausea and emesis, abuse liability and the development of addiction. These effects serve to limit the utility of opiates for controlling post injury pain. Addiction liability can occur secondary to medical uses of the drug where the central effects lead to an addicted and dependent state.

Because constipation is among the actions of opiates, many agents selected for anti-diarrheal activity act via one or more of these opioid receptors. Also, because of the diverse actions mediated by opioid receptors, such agents also have undesirable central nervous system effects and abuse potential. Because of these diverse activities and the potential for abuse, anti-diarrheal opioid drug development has been directed towards identifying compounds in which the potentially beneficial activities are separated from the activities that lead to abuse and dependence.

During the mid to late 1960's, several agents derived from classes of molecules known to have opioid activity were synthesized. These agents were shown to have naloxone reversible suppressant effects in smooth muscle bioassays and were able to readily displace opioid ligands in receptor binding assays. These results indicated that they act via direct or indirect action with opioid receptors. These compounds were designed to be selective anti-diarrheal opioid receptor (believed to be the $\mu$ receptor) agonists that are substantially free from analgesic and habit-forming activities (see, e.q., Shriver et al. (1987) "Loperamide" in *Pharmacological and Biochemical Properties of Drug Substances,* Vol. 3, Goldberg, M. E., ed. Am. Pharm. Assoc., Washington, D.C., p. 462).

Compounds, such as loperamide [4-(p-chlorophenyl)-4-hydroxy-N-N-dimethyl-α,α-diphenyl-1- piperidinebutyramide hydrochloride], and its analogs were among those synthesized. Loperamide was widely reported to be completely devoid of analgesic effects and CNS effects [see, e.g., Jaffe et al. (1980) Clin. Pharmacol. Ther. 80:812–819] even at relatively high dosages. Subsequent work has explored whether loperamide administered to mice intraparenterally might provide analgesic effects [see, e.g., Takasuna et al. (1994) Behavioural Pharm. 5:189–195]. Specifically, Takasuna et al. report that suppression of acetic acid-induced writhing was observed when loperamide was administered. The authors note, however, that the writhing response depends on sensorimotor integration, and that drugs may suppress writhing by impairing the subject's motoric ability to respond without affecting the sensory events consequent to the administration of a chemical irritant (see, Takasuna et al. (1994) Behavioural Pharm. 5:189–195). The authors state that it remains to be determined whether or not loperamide has any analgesic properties.

In contrast to conventional opiates, however, loperamide and analogs thereof and other such agents exhibit little or no analgesic effects as measured in acute pain models, such as the tail clip and hot plate tail withdrawal tests, when given systemically [see, e.g., Stahl et al. (1977) Eur. J. Pharmacology 46:199–205; Shriver et al. (1981) "Loperamide" in Pharmacological & Biochemical Properties of Drug ubstances Vol. 3, Goldenberg, Ed., American Pharmaceutical Assn. Press, pp. 461–476; see, also U.S. Pat. Nos. 3,714,159 and 3,884,916]. This absence of CNS effects, including analgesic effects, is believed to be related to the failure of such compounds to effectively cross the blood brain barrier. This failure is in part due to the extremely high lipid partition coefficient of the compounds. The high partition coefficient results in sequestration of the compound in the lipid membrane. This local absorption is thought to contribute to its failure to cross the blood brain barrier. In support of this conclusion, antinociceptive analgesic action has been observed after direct delivery into the brain [Stahl et al. (1977) Eur. J. Pharmacology 46:199–205].

Peripheral Injury and Hyperalgesia

Changes in the milieu of the peripheral sensory terminal occur secondary to local tissue damage. Mild damage [such as abrasions or burns] and inflammation in the cutaneous receptive fields or joints will produce significant increases in the excitability of polymodal nociceptors [C fibers] and high threshold mechanoreceptors [Handwerker et al. (1991) Proceeding of the VIth World Congress on Pain, Bond et al., eds., Elsevier Science Publishers BV, pp. 59–70; Schaible èt al. (1993) Pain 55:5–54]. This increased excitability leads to increased spontaneous activity [in otherwise silent sensory afferents] and an exaggerated response to otherwise minimal stimuli.

These events have several consequences. First, the magnitude of the pain state in humans and animals is proportional to the discharge rate in such sensory afferent [Raja et al. (1988) Anesthesiology 68:571–590]. The facilitated response secondary to the local peripheral injury may lead to an exaggerated pain state simply because of the increased afferent activity. Secondly, spontaneous activity in small sensory afferent causes central neurons in the spinal cord to develop an exaggerated response to subsequent input [Woolf et al. (1991) Pain 44:293–299; Neugebauer et al. (1993) J. Neurosci. 70:1365–1377]. Both of these events, secondary to the increased spontaneous activity and reactivity in small sensory afferents generated by the peripheral injury leads to a behavioral state referred to as hyperalgesia (Yaksh (1993) Current Opinion in Neurology and Neurosurgery 6:250–256).

Thus, in the instance where the pain response is the result of an exaggerated response to a given stimulus, the organism is hyperalgesic. The importance of the hyperalgesic state in the post injury pain state has been repeatedly demonstrated and this facilitated processing appears to account for a major proportion of the post-injury/inflammatory pain state [see, e.q., Woold et al. (1993) Anesthesia and Analgesia 77:362–79; Dubner et al. (1994) In, Textbook of Pain, Melzack et al., eds., Churchill-Livingstone, London, pp. 225–242].

Certain drug actions may serve to normalize the sensitivity of the organism. Experimental investigations have shown that opiates with an action in the vicinity of the peripheral terminal in injured or inflamed tissue will normalize the activity in afferent innervating inflamed skin [Russell et al. (1987) Neurosci. Lett 76:107–112; Andreev et al. (1994) Neurosci. 58:793–798] and normalize the hyperalgesic threshold [Stein (1988) Eur. J. Pharmac. 155:255–264 Stein (1993) Anesth. Analg. 76:182–191]. Opiates, such as morphine, however, when peripherally applied, may have a short duration of action and would, if applied at sufficient levels, have effects upon consciousness and respiration. The possible systemic effects, CNS effects and abuse potential render conventional opioids unsuitable for local application and unsuitable as peripheral anti-hyperalgesics. Thus, there is a need for effective anti-hyperalgesics that directly block peripheral sensitization, but that do not have concomitant central nervous system [CNS] effects, including the potential for abuse.

Therefore, it is an object herein to provide anti-hyperalgesics for local and topical application that have minimal or no CNS effects.

SUMMARY OF THE INVENTION

Methods for treatment and/or prevention of peripheral local inflammatory states, including, but not limited to, inflammation following local infection, blister, boils, or acute skin injuries, such as abrasions, burns, such as thermal, radiation, sunburn and chemical burns, windburn, frostbite, superficial cuts, surgical incisions, contusions, irritations, inflammatory skin conditions, including but not limited to poison ivy, and allergic rashes and dermatitis, insect stings and bites, joint inflammation, post-surgical hyperalgesic conditions and any condition that yields a hyperalgesic pain state are provided. Such conditions and indications, include, but are not limited to: a) skin conditions;; b) oral, laryngal and bronchial conditions and indications; c) ophthalmic indications and conditions; d) post surgical conditions and indications; e) recto-anal inflammations; and f) inflammations associated with infectious agents.

These methods involve topical or local administration of compositions that contain one or more compounds that exert anti-hyperalgesic activity via peripheral opiate receptors, but that do not exhibit CNS, CNS-mediated analgesic or systemic effects [particularly CNS effects] at dosages at which they are topically or locally applied. The intended locus of application includes, but is not limited to, any body surface or part that is amenable to local or topical treatment. Such body parts include, but are not limited to: the skin, joints, eyes, lips and mucosal membranes.

The methods use compositions containing opioid anti-diarrheal compounds or other opiate receptor agonist compounds that do not, upon topical or local administration, evoke CNS effects, as defined herein, particularly at the peripheral anti-hyperalgesic dosage. The compositions that contain the opioid anti-diarrheal compounds or other opiate receptor compounds are also provided.

Typically the compounds intended for use in the compositions and methods herein possess peripheral antihyperalgesic and substantially no CNS activities, as defined herein, because, without being bound by any theory, they do not effectively cross the blood brain barrier. The failure to cross the blood brain barrier precludes the occurrence of the CNS systemic effects, so that there is limited potential for abuse. Other opioids, such as morphine, that readily cross the blood brain barrier could be effective as antihyperalgesics, but their permeability through the blood brain barrier results in abuse liability. Their scheduling by the Drug Enforcement Agency limits their applicability.

In contrast, the compositions provided herein, contain opioids that do not, upon topical or local administration, substantially cross the blood brain barrier as assessed by assays described herein. The compounds intended for use in the methods and compositions provided herein include any compound that by virtue of its interaction, either directly or indirectly, with peripheral opioid receptors ameliorates the peripheral hyperalgesic state, but does not exhibit systemic CNS-mediated analgesic activity [i.e., analgesic activity by virtue of interaction with CNS opioid receptors] or CNS side-effects, including heaviness of the limbs, flush or pale complexion, clogged nasal and sinus passages, dizziness, depression, respiratory depression, sedation and constipation. These compounds include anti-diarrheals that act as anti-diarrheals via interaction with $\mu$, $\delta$ or $\kappa$ receptors, especially $\mu$ and $\delta$ receptors, and opiate agonists, such as metkephamide and related enkephalin analogs. Examples of such compounds include, but are not limited to:

(i) loperamide [4-(p-chlorophenyl)-4-hydroxy-N-N-dimethyl-α,α-diphenyl-1-piperidinebutyramide hydrochloride]], loperamide analogs and related compounds as defined herein [see, Formula (I); see, also, U.S. Pat. Nos. 3,884,916 and 3,714,159; see, also U.S. Pat. Nos. 4,194,045, 4,116,963, 4,072,686, 4,069,223, 4,066,654,], N-oxides of loperamide and analogs, metabolites and prodrugs thereof and related compounds as defined herein [see, also, U.S. Pat. No. 4,824,853], and related compounds, such as (a), (b) and (c) as follows:
  (a) 4-(aroylamino)piperidine-butanamide derivatives and N-oxides thereof as defined herein [see, also U.S. Pat. No. 4,990,521];
  (b) 5-(1,1-diphenyl-3-(5- or 6-hydroxy-2-azabicyclo-(2.2.2)oct-2-yl)propyl)-2-alkyl-1,3,4-oxadiazoles, 5-(1,1-diphenyl-4-(cyclic amino)but-2-trans-en-1-yl)-2-alkyl-1,3,4-oxadiazoles, 2-[5-(cyclic amino)-ethyl-10,11-dihydro-5H-dibenzo[a,d]-cyclohepten-5-yl]-5-alkyl-1,3,4-oxadiazoles] and related compounds [see, U.S. Pat. Nos. 4,013,668, 3,996, 214 and 4,012,393];
  (c) 2-substituted-1-azabicyclo[2,2,2]octanes [see, U.S. Pat. No. 4,125,531];

(ii) 3-hydroxy-7-oxomorphinans and 3-hydroxy-7-oxoisomorphinans [see, e.g., U.S. Pat. No. 4,277,605] including, but not limited to: 3-hydroxy-7-oxomorphinan and 3-hydroxy-7-oxoisomorphinans including d,l-3-hydroxy-7-oxo-N-methylmorphinan, l-3-hydroxy-7-oxo-N-methyl-morphinan, d,l-3-hydroxy-7-oxomorphinan, l-3-hydroxy-7-oxomorphinan, d,l-3-hydroxy-7-oxo-N-methylisomorphinan, l-3-hydroxy-7-oxo-N-methylisomorphinan, d,l-3-hydroxy-7-oxoisomorphinan and l-3-hydroxy-7-oxoisomorphinan;

(iii) amidinoureas as provided herein [see, also U.S. Pat. Nos. 4,326,075, 4,326,074, 4,203,920, 4,060,635, 4,115,564, 4,025,652] and 2-[(aminophenyl and amidophenyl)amino]-1-azacycloalkanes [see, U.S. Pat. No. 4,533,739];

(iv) metkephamid [H-L-Tyr-D-Ala-Gly-L-Phe-N(Me)Met-NH$_2$; see, e.g., U.S. Pat. No. 4,430,327; Burkhart et al. (1982) *Peptides* 3:869–871; Frederickson et al. (1991) *Science* 211:603–605] and other synthetic opioid peptides, such as H-Tyr-D-Nva-Phe-Orn-NH$_2$, H-Tyr-D-Nle-Phe-Orn-NH$_2$, H-Tyr-D-Arg-Phe-A$_2$bu-NH$_2$, H-Tyr-D-Arg-Phe-Lys-NH$_2$, and H-Lys-Tyr-D-Arg-Phe-Lys-NH$_2$ [see, U.S. Pat. No. 5,312,899; see, also Gesellchen et al. (1981) *Pept.: Synth., Struct., Funct., Proc. Am. Pept. Symp.*, 7th,; Rich et al. (Eds), Pierce Chem. Co., Rockford, Ill., pp. 621–62] that do not cross the blood brain barrier;

(v) propanamines as defined in U.S. Pat. No. 5,236,947; and (vi) other opioid compounds that may agonize peripheral $\mu$ or $\kappa$ receptors, especially $\mu$ receptors, but that, upon topical or local administration, do not cross the blood brain barrier and do not exhibit substantial CNS effects as defined herein.

The methods will employ compounds, such as those listed above, and further include compounds, such as: (viii) certain phenylacetamide derivatives [see, U.S. Pat. No. 5,242,944], including, but not limited to N-{(3,4-dimethylphenyl)propyl}-4-(2-aminoethoxy)-3-methoxy-phenylacetamide, N-{(3,4-dimethylphenyl)propyl}-4-(2-aminoethoxy)-3-hydroxy-phenylacetamide, N-{(3,4-dimethylphenyl)propyl}-4-(2-aminoethoxy)-3-aminophenylacetamide, N-{(3-methylphenyl)propyl}-4-(2-aminoethoxy)-3-methoxy-phenylacetamide, N-{(3-methylphenyl)propyl}-4-(2-aminoethoxy)-3-hydroxy-phenylacetamide and N-{(3-dimethylphenyl)propyl}-4-(2-aminoethoxy)-3-amino phenylacetamide.

Preferred compounds for use in the compositions and methods herein are the loperamide analogs and N-oxides, preferably an N-oxide of a piperidine-nitrogen, thereof or other pharmaceutically acceptable derivatives thereof and related compounds [see (i), above]. These preferred compounds include compounds of formula (I):

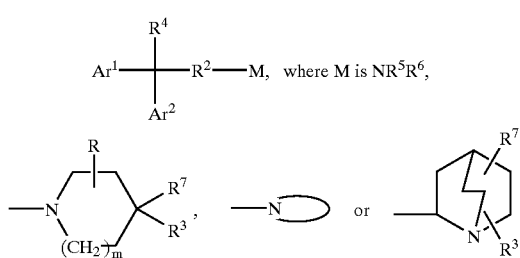

in which:

m is an integer from 0 to 3, preferably 1 to 3, more preferably 1 or 2, and most preferably 2;

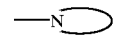

is an azabicycloalkyl containing from 6 to 9 carbon atoms with at least 5 atoms in each ring, which ring is preferably pyrrolidino, piperidino, or hexamethylenimino, where the tertiary amine is:

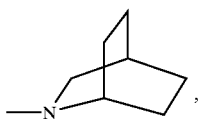

and is unsubstituted or substituted with $OR^{18}$ in which $R^{18}$ is hydrogen or lower alkanoyl containing 2 to 7, preferably 2 or 3, carbon atoms, and $OR^{18}$ is preferably attached at the 5 position in 5-membered rings or the 5 or 6 position in 6-membered rings and is attached in the endo or exo configuration, where $R^3$, $R^7$, $R^5$ and $R^6$ are as defined below. The tertiary amine is preferably:

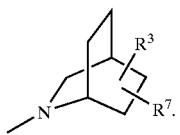

M is more preferably selected from among:

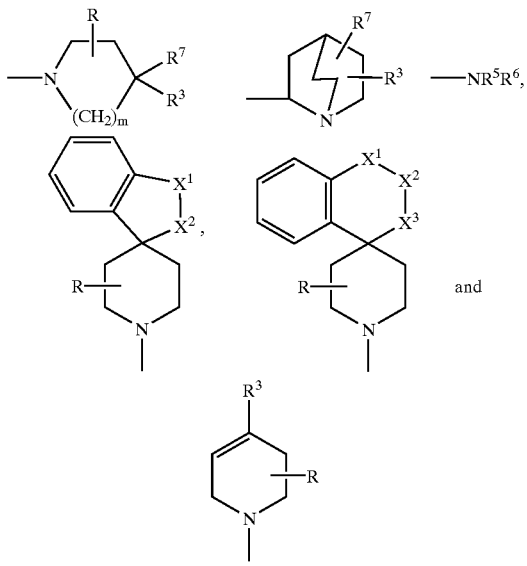

where m is an integer from 1 to 3, preferably 1 or 2, more preferably 2; and $X^1$, $X^2$ and $X^3$ are $-C(R^{24})(R^{25})-$, $-C(R^{24})=C(R^{25})-$, $-C(R^{24})=N-$, $-N=C(R^{24})-$, $-C(=O)-$, $-O-$, $-S-$ or $-N(R^{24})-$, with the proviso that only one of $X^1$, $X^2$ and $X^3$ may be O, S or $NR^{24}$; and $R^{24}$ and $R^{25}$ are hydrogen or lower alkyl.

$Ar^1$ and $Ar^2$ are either (i) or (ii) as follows:

(i) each is independently selected from a ring system, preferably a 6- to 10-membered ring system, more preferably an aryl ring system, or a heteroatom-containing ring system, preferably a 5- to 10-membered heteroatom-containing ring system, more preferably a heteraryl ring system, containing 1 or more heteroatoms, preferably 1 to 3 heteroatoms, such as oxygen, sulfur or nitrogen atoms, wherein the aryl and heteroaryl ring systems are each optionally substituted with one or more, preferably up to three, aryl group substituents [as defined herein], and $Ar^1$ and $Ar^2$ are each preferably independently phenyl or pyridyl, optionally substituted with halo, hydroxy, haloalkyl, preferably halo lower alkyl, particularly trifluoromethyl, alkyl, alkyloxy, aminosulfonyl, alkylcarbonyl, nitro, amino, aminocarbonyl, phenylcarbonyl which is optionally substituted with one or more, preferably up to three, substituents selected from halo, halo alkyl and alkyl, or thienyl which is optionally substituted with halo, haloalkyl or alkyl, where the alkyl groups are straight or branched chain and preferably contain from 1 to 6 carbons, more preferably 1 to 3 carbons; or (ii) $Ar^1$ and $Ar^2$ are each independently phenyl or pyridyl groups, which are unsubstituted or substituted with, preferably aryl substituent groups, as defined herein, preferably phenyl, and with the carbon to which they are commonly linked form a fused ring system, so that the compounds of formula (I) have the structure:

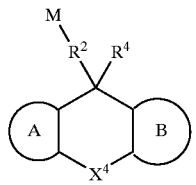

and is preferably,

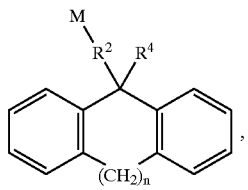

where:

A and B are independently selected from phenyl and pyridyl, preferably phenyl, which are unsubstituted or substituted, preferably with up to three aryl group substituents;

$X^4$ is a direct bond, $-(CH_2)_n-$, $-CH=CH-$, $-CH=CHCH_2-$, $-(CH_2)_pO(CH_2)_q-$, $-(CH_2)_pS(O)_r(CH_2)_q-$, $-(CH_2)_pNR^{21}(CH_2)_q-$ or

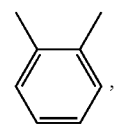

n is an integer from 0 to 3, preferably 1 to 3, and more preferably 2 or 3;

each of p and q is 0 or 1, and the sum of p and q is no greater than 2;

r is 0 to 2;

$R^2$ is a direct bond, is alkylene in which the alkylene group is a straight or branched chain, preferably is alkylene containing from 1 to 12, preferably 1 to 6, more preferably 1 to 3 carbons and most preferably is $-(CH_2)_2-$ or $-CH_2CH(CH_3)-$, is alkenylene having 2 to 6 carbon atoms, preferably 2 to 3 carbons atoms, and one or two, preferably one, double bond, or is alkynylene in which the alkynylene group is a straight or branched chain, preferably is alkynylene containing from 2 to 12, preferably 2 to 6, more preferably 2 to 3 carbons; in all instances the chains are unsubstituted or substituted, and, if substituted, preferably with one or more hydroxy groups;

$R^3$ is selected from $Ar^3$, —Y—$Ar^3$, where Y is alkylene or alkenylene having, preferably, 2 to 4 carbon atoms; alkenyl containing 2 to 4 carbons; cycloalkyl containing 3 to 8 carbons; heterocycle, preferably 1-pyrrolidinyl, 1-piperidinyl, 1-hexamethyleneiminyl, 1-morpholinyl or —N($Ar^4$)—$R^{23}$, where $R^{23}$ is alkyl; alkenyl; alkanoyl which is optionally substituted, preferably with halo, hydroxy or alkoxy, preferably lower alkanoyl; alkenoyl having 3 to 10 carbons and 1 to 3 double bonds; optionally substituted aroyl, preferably benzoyl; heteroaroyl, preferably pyridoyl, furoyl and thienoyl; alkoxycarbonyl, preferably lower alkoxycarbonyl; alkenyloxycarbonyl having 3 to 10 carbons and 1 to 3 double bonds; aryloxycarbonyl, preferably phenoxycarbonyl; formyl (—CHO); cyano; aminocarbonyl (—CONH$_2$); alkylaminocarbonyl; dialkylaminocarbonyl, arylaminocarbonyl, diarylaminocarbonyl or arylalkylaminocarbonyl; or

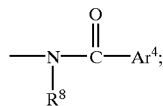

$R^8$ is hydrogen or alkyl that is a straight or branched chain, preferably containing from 1 to 6, more preferably 1 to 3, carbon atoms;

$Ar^3$ is selected from a ring system, preferably a 6- to 10-membered ring system, more preferably an aryl ring sytem, or a heteroatom-containg ring system, preferably a 5- to 10-membered heteroatom-containing ring system, more preferably a heteraryl ring system, containing 1 or more heteroatoms, preferably 1 to 3 heteroatoms, such as oxygen, sulfur or nitrogen atoms, wherein the aryl and heteroaryl ring systems are each optionally substituted with one or more, preferably up to three, aryl group substituents [as defined herein]; it is more preferably an aryl ring system, preferably a 6- to 10-membered aryl ring system, or a heteroaryl ring system, preferably a 5- to 10-membered heteroaryl ring system, containing 1 or more heteroatoms, preferably 1 to 3 heteroatoms, such as oxygen, sulfur or nitrogen atoms, in which the aryl and heteroaryl ring systems are each unsubstituted or substituted with one or more, preferably up to three, substitutents, preferably aryl group substituents halo, halo lower alkyl or lower alkyl, and $Ar^3$ is preferably phenyl or pyridyl unsubstituted or substituted with halo, halo lower alkyl or lower alkyl;

$Ar^4$ is either:

(i) heterocycle containing 1 ring or 2 or more fused rings, preferably 1 ring or 2 to 3 fused rings, where each ring contains 1 or more, preferably 1 to 3 heteroatoms, and preferably contains 4 to 10 members, more preferably 5 to 7 members, and is optionally substituted with one or more, preferably up to three, aryl group substituents, preferably halo, halo lower alkyl or lower alkyl, and $Ar^4$ is preferably selected from heterocycles that include, but are not limited to, indolyl, benzofuranyl, benzothienyl, isoquinolinyl, quinolinyl, benzimidazoly, thienyl, furanyl, pyridinyl, thiazolyl and imidazolyl, each of which is optionally substituted, preferably with halo, halo lower alkyl or lower alkyl, preferably halo, and the heterocycle is more preferably selected from thienyl, furanyl, pyridinyl, thiazolyl and imidazolyl; or (ii) a radical of formula:

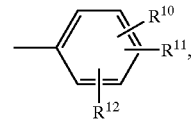

in which:

$R^{10}$, $R^{11}$ and $R^{12}$ are each independently selected from hydrogen, alkyloxy, alkoxyalkyl, halo, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, $C_{3-6}$alkynyloxy, arylalkyloxy, aryloxy and alkyl, in which alkyl, alkenyl, alkynyl or aryl group defined by $R^{10}$, $R^{11}$ and $R^{12}$ is unsubstituted or substituted with one or more, preferably 1 to 4 substituents selected from halo, halo alkyl, preferably halo lower alkyl, or alkyl, preferably lower alkyl, and the alkyl groups are straight or branched chains that are preferably lower alkyl ($C_{1-6}$) and more preferably $C_{1-3}$ or (iii) 1- or 2-naphthyl, dihydronaphthyl, tetrahydronaphthyl, indenyl or dihydroindenyl, each of which is optionally substitituted with one or more aryl group substituents;

R is halo, haloalkyl, preferably lower halo alkyl, or alkenyl having 3 to 12 carbons, preferably lower alkenyl or hydroxy and is preferably at the 3-position [relative to the N], more preferably a 3-halo or 3-lower alkyl, or R is OR$^9$ that is preferably at the 3-position so that the piperidinyl ring has the formula:

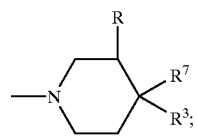

$R^9$ is selected from hydrogen, alkyl, arylalkyl, alkylcarbonyl, aminoalkyl, alkylaminoalkyl, dialkylaminoalkyl, in which the alkyl groups are straight or branched chains and preferably contain 1 to 12, more preferably 1 to 6 carbons, more preferably 1–3 carbons in the chain;

$R^4$ is selected from among:

(i) an aryl ring system, preferably a 6- to 10-membered aryl ring system, or a heteroaryl ring system, preferably a 5- to 10-membered heteroaryl ring system, containing 1 or more heteroatoms, preferably 1 to 3 heteroatoms, such as oxygen, sulfur or nitrogen atoms, in which the aryl and heteroaryl ring systems are each optionally substituted with one or more, preferably up to three aryl group substituents, and $R^4$ is preferably phenyl or pyridyl which is optionally substituted with lower alkyl, halo or halo lower alkyl, with phenyl being even more preferred, or (ii) a heterocyclic ring containing one to three heteroatoms, that is unsubstituted or substituted with halo, halo lower alkyl or lower alkyl, and is preferably a pyrrolidinyl, oxadiazolyl or triazolyl radical, more preferably oxadiazolyl, most preferably 1,3,4-oxadiazolyl, particularly a 5-substituted 1,3,4-oxadiazolyl in which the substituent is halo, halo lower alkyl, hydroxy, lower alkoxy or lower alkyl, or (iii) alkyl containing 1 to 8 carbons which is optionally substituted with hydroxy or alkylcarbonyloxy (—OCOR), preferably 1 to 6 carbons, more preferably 1 to 3 carbons; alkenyl containing 3 to 6 carbons; cycloalkylalkyl in which the cycloalkyl contains 3 to 8 carbons and the alkyl contains 1 to 3 carbons; cycloalkenylalkyl in which the cycloalkenyl contains 3 to 8 carbons and the alkyl contains 1 to 3 carbons; or (iv)

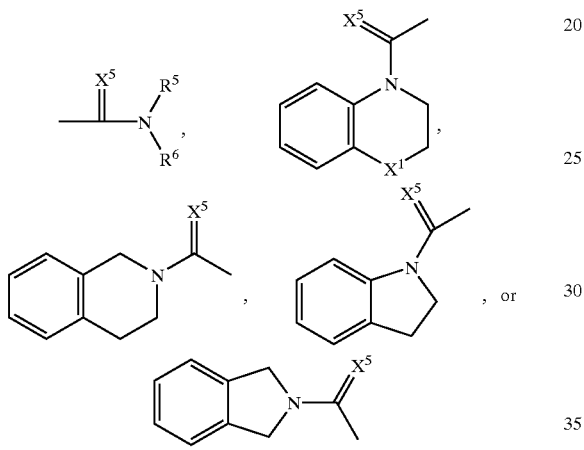

where
$X^1$ is as previously defined;
$X^5$ is O or S;
$R^5$ and $R^6$ are either:
(a) independently selected from hydrogen, alkyl that is a straight or branched chain containing 1 to 12, preferably 1 to 6 carbons, more preferably 1–3 carbons, alkenyl that is straight or branched chain, containing 2 to 12, preferably containing 3–6 carbons and one or two double bonds, alkynyl that is straight or branched chain, containing 2 to 12, preferably containing 3–6 carbons and one or two double bonds, or aryl, preferably a 6- to 10-membered aryl ring system that is optionally substituted with one or more, preferably up to three, aryl group substituents, or arylalkyl, and each is preferably 2-propenyl, ethyl, methyl or aryl, preferably phenyl or phenylmethyl, or (b) $R^5$ and $R^6$ are each independently selected from carbon chains, heteroatoms, and carbon chains containing one or more heteroatoms, so that together with the nitrogen atom to which each is attached, they form a 3- to 10-, preferably 4–7, more preferably 5 to 6-membered heterocyclic ring containing one to three heteroatoms, that is preferably a piperidinyl, alkylpiperidinyl, morpholinyl, oxadiazolyl, triazolyl or pyrrolidinyl radical that is unsubstituted or substituted with halo, halo lower alkyl, hydroxy, lower alkoxy or lower alkyl, and is more preferably a 1,3,4-oxadiazolyl, 4-morpholinyl, or di($C_1$–$C_6$ alkyl)-morpholinyl, preferably 2,6-di($C_1$–$C_6$ alkyl)-4-morpholinyl, radical;

(v) cyano, formyl, alkoxycarbonyl, aryloxycarbonyl, alkylcarbonyl or arylcarbonyl;

(vi) —$NR^5COR^5$; or (vii) —$S(O)_r$alkyl or —$S(O)_r$aryl, where r is 1 or 2; and $R^7$ is selected from among:
—H;
OH;
—$R^{14}OR^{13}$ in which $R^{13}$ is hydrogen, lower alkyl, preferably containing 1 to 4 carbons, or alkanoyl containing 2 to 5, preferably 2 or 3, carbon atoms, and $R^{14}$ is lower alkylene, preferably alkylene of 2 to 4 carbon atoms, more preferably methylene or ethylene, or $R^{14}$ is alkenylene of 2 to 6 carbon atoms, alkynylene of 2 to 4 carbon atoms;
—$CH_2NR^{15}R^{16}$ in which $R^{15}$ is hydrogen, lower alkyl, lower alkanoyl, aryl or aroyl, and $R^{16}$ is hydrogen or lower alkyl or, together with the nitrogen atom to which they are attached, $R^{15}$ and $R^{16}$ form a 3 to 7-membered ring which optionally contains an additional heteroatom selected from oxygen, nitrogen or sulfur;
—$OR^{15}$;
—C(O)H;
—CN;
—C(=O)$NR^5R^6$ in which $R^5$ and $R^6$ are as previously defined; alkyl, preferably lower alkyl;
aryl, preferably phenyl;
—C(O)$OR^{17}$ in which $R^{17}$ is hydrogen, alkyl containing from 1 to 7 carbon atoms, alkenyl having 3 to 7 carbon atoms, an optionally substituted aryl ring system (preferably a 6 to 10-membered aryl ring system), an optionally substituted heteroaryl ring system (preferably a 5 to 10-membered heteroaryl ring system) containing 1 or more heteroatoms, preferably 1 to 3 heteroatoms, such as oxygen, sulfur or nitrogen atoms, alkylaryl, arylalkyl, preferably benzyl, phenethyl, phenylpropyl or phenylbutyl, heteroarylalkyl, preferably furylmethyl, thienylethyl or pyridylpropyl, particularly pyridyl, phenyl, tolyl, ethylphenyl, butylphenyl or halophenyl, or a pharmaceutically acceptable cation, such as an alkali metal or alkaline earth metal, including sodium, potassium, calcium and ammonium cations;

where the optional aryl group substituents are selected from halo, alkyl, cycloalkyl, cycloalkylalkyl, aryl, heteroaryl, arylalkyl, heteroarylalkyl, alkenyl containing 1 to 2 double bonds, alkynyl containing 1 to 2 triple bonds, haloalkyl and polyhaloalkyl, especially trifluoromethyl, formyl, alkylcarbonyl, arylcarbonyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfonyl.

In certain embodiments herein, when $Ar^3$ is 1-(3-propionyl-2-imidazolinon)yl, then $R^4$ is other than —CN. Also in certain embodiments herein, when $R^4$ is —C(=$X^5$)—$NR^5R^6$, $X^5$ is O and $R^5$ and $R^6$, together with the nitrogen atom to which they are attached form pyrrolidinyl, then M is other than 4-morpholinyl. In yet other certain embodiments, when M is —$NR^5R^6$ and $R^5$ and $R^6$ are methyl, then $R^4$ is other than 1-hydroxypropyl ($CH_3CH_2CH(OH)$—) or ethylcarbonyl ($CH_3CH_2C(=O)$—). In still other certain embodiments, when M is 4-morpholinyl or 1-piperidinyl, then $R^4$ is other than ethylcarbonyl ($CH_3CH_2C(=O)$—). In certain other embodiments, when M is 4-morpholinyl, than $R^4$ is other than ethoxycarbonyl ($CH_3CH_2OC(=O)$—).

Also intended for use herein are salts of the compounds of formula (I), including salts with pharmaceutically acceptable acids and quaternary ammonium salts, N-oxides of the compounds of formula (I) and salts thereof, including salts with pharmaceutically acceptable acids and quaternary ammonium salts, including stereoisomeric forms of quaternary ammonium salts, prodrugs of the compounds of formula (I), and metabolites of the compounds of formula (I), including, for example, glucuronides.

Among the suitable quaternary ammonium salts of the compounds of formula (I), are for example, compounds of the following formulae:

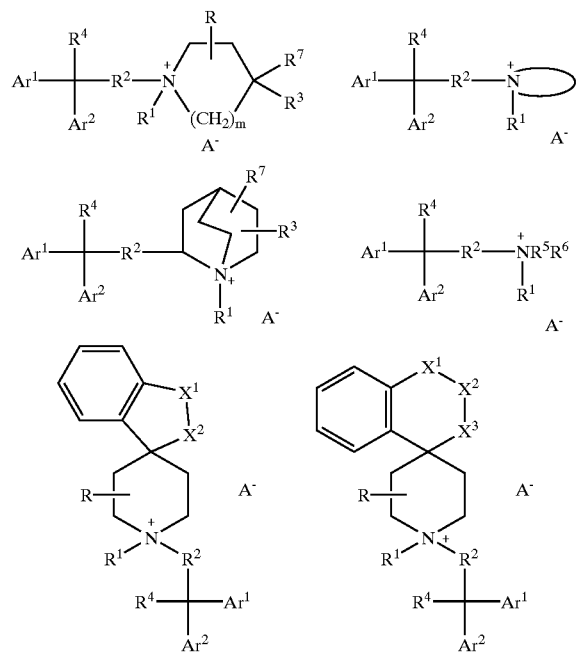

in which:
$R^1$ is alkyl of 1 to 12 carbons which is optionally substituted with 1 to 6 halo atoms, 1 to 3 hydroxy groups or 1 to 3 alkoxy groups; alkenyl of 3 to 12 carbons which contains 1 to 3 double bonds and is optionally substituted with 1 to 6 halo atoms; alkynyl of 3 to 12 carbons which contains 1 to 3 triple bonds and is optionally substituted with 1 to 6 halo atoms; arylalkyl wherein the alkyl chain contains 1 to 6 carbons and the aryl group contains 6 to 10 carbons, preferably phenyl, and is optionally substituted with 1 to 3 aryl group substituents; arylalkenyl wherein the alkenyl chain contains 3 to 6 carbons and 1 to 3 double bonds and the aryl group contains 6 to 10 carbons, preferably phenyl, and is optionally substituted with 1 to 3 aryl group substituents; arylalkynyl where the alkynyl chain contains 3 to 6 carbons and 1 to 3 triple bonds and the aryl group contains 6 to 10 carbons, preferably phenyl, and is optionally substituted with 1 to 3 aryl group substituents; cycloalkyl of 3 to 8 carbons; cycloalkenyl of 3 to 8 carbons; cycloalkylalkyl in which the cycloalkyl group contains 3 to 8 carbons and the alkyl chain contains 1 to 6 carbons; cycloalkenylalkyl in which the cycloalkenyl group contains 3 to 8 carbons and the alkyl chain contains 1 to 6 carbons;

A is halo, hydroxy, alkoxy of 1 to 12 carbons, alkanoyloxy of 1 to 12 carbons or aroyloxy, preferably benzoyloxy, or any other pharmaceutically acceptable group that is capable of forming a counterion in a quaternary ammonium salt; and m, $X^1$, $X^2$, $X^3$, R, $R^2$, $R^3$, $R^4$, $R^5$, $R^6$, $R^7$, $Ar^1$ and $Ar^2$ are as previously defined.

It is understood that compounds of the above formula [or any of the compounds described herein] may have one or more asymmetric centers. Pure enantiomers of the above compounds may be obtained, and diastereoisomers isolated by physical separation methods, including, but not limited to crystallization and chromatographic methods. Cis and trans diasteriomeric racemates may be further resolved into their isomers. If separated, active isomers may be identified by their activity as defined herein. Such purification is not, however, necessary for preparation of the compositions or practice of the methods herein.

Of the above classes of compounds and compounds of formula (I), the compounds for use in the methods and compositions herein are those that, upon topical or local administration, exhibit activity as peripheral anti-hyperalgesics but, upon local or topical administration, are substantially devoid of CNS activity as defined below. Such compounds are typically anti-diarrheal compounds, as assessed in standard assays, that exhibit low or no activity in assays that assess CNS activity. As defined below, for purposes herein, such anti-diarrheal and CNS activity is assessed in standard assays relative to 1-(3-cyano-3,3-diphenylpropyl)-4-phenyl-4-piperidinecarboxylic acid ethyl ester (also know as 2,2-diphenyl-4-[(4-carbethoxy-4-phenyl)piperidino]butyronitrile), generically known as diphenoxylate. Selected compounds for use in the methods and compositions herein have:

(1) activity as a peripheral anti-hyperalgesic agent as assessed in any recognized in vivo or in vitro model or assay; and substantially no CNS-mediated effects, which are preferably assessed by selecting compounds that have (2) either
(a) a B/A ratio greater than or equal to diphenoxylate and a B value at least about 2-fold greater than diphenoxylate, or
(b) a B/A ratio, at least equal to, and preferably more than about 2-fold greater than diphenoxylate, where:
B is the $ED_{50}$ of the compound in an art-recognized assay [the hot plate tail withdrawal test or the tail clip test, described below, tail flick or assay that yields equivalent or substantially equivalent results] that measures CNS activity of the compound, and
A is the $ED_{50}$ of the compound in an art-recognized assay [the Castor Oil test or Antagonism of $PGE_2$-induced diarrhea in mice, described below, or an assay that yields equivalent results] that measures anti-diarrheal activity of the compound. The ratio of these activities of the compound of interest is compared to the ratio of the activities of diphenoxylate in the same assays. Among preferred compounds are those that have a B/A ratio that is more than about 3-fold greater than diphenoxylate, although compounds with a B/A ratio greater than or equal to diphenoxylate may also be used.

Preferred among the compounds of formula (I) are those of formula (II) or N-oxides thereof:

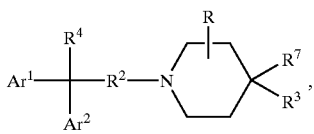

preferably where $R^4$ is

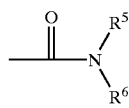

and more preferably where $R^7$ is OH, R is hydrogen or methyl, and $R^3$ is $Ar^3$, preferably phenyl, more preferably 4-halo-phenyl. Yet more preferred are compounds where $R^5$ and $R^6$ are methyl or ethyl, or together with the nitrogen to which they are attached form a pyrrolidine or piperidine ring.

More preferred among these compounds are loperamide [4-(p-chlorophenyl)-4-hydroxy-N-N-dimethyl-α,α-diphenyl-1-piperidinebutyramide hydrochloride] and analogs [see formula III] thereof that exhibit B/A ratios greater than loperamide [see, e.q., U.S. Pat. Nos. 3,884,916 and 3,714,159]. Such compounds include those in which:

(i) $Ar^1$ and $Ar^2$ are phenyl, R is hydrogen, $R^2$ is $(CH_2)_2$, $R^5$ and $R^6$, with the nitrogen to which each is linked form pyrrolidine and $R^3$ is 4-chlorophenyl or 3,4,-dichlorophenyl;

(ii) $Ar^1$ and $Ar^2$ are phenyl, R is hydrogen, $R^2$ is $(CH_2)_2$, $R^5$ and $R^6$, with the nitrogen to which each is linked form piperidinyl and $R^3$ is phenyl;

(iii) $Ar^1$ and $Ar^2$ are phenyl, $R^2$ is $(CH_2)_2$, R is hydrogen, $R^5$ and $R^6$ are each methyl and $R^3$ is 4-bromophenyl;

(iv) $Ar^1$ and $Ar^2$ are phenyl, $R^2$ is $(CH_2)_2$, R is hydrogen, $R^5$ and $R^6$ are methyl and ethyl, respectively, and $R^3$ is 4-chlorophenyl;

(v) $Ar^1$ and $Ar^2$ are phenyl, $R^2$ is $CH_2CHCH_3$, R is hydrogen, $R^5$ and $R^6$ are each methyl and $R^3$ is 4-fluorophenyl; and (vi) $Ar^1$ and $Ar^2$ are phenyl, $R^2$ is $CH_2CH_2$, R is 4-methyl, $R^5$ and $R^6$ are each methyl and $R^3$ is 3-trifluoromethylphenyl or phenyl.

In certain other preferred embodiments, the compounds of formula (I) are those of formula (II) above, preferably where $R^4$ is cyano and $R^7$ is $—C(O)OR^{17}$, in which $R^{17}$ is preferably hydrogen or lower alkyl, more preferably methyl or ethyl. More preferred among these compounds is diphenoxylate (2,2-diphenyl-4-[(4-carbethoxy-4-phenyl)piperidino]butyronitrile) and defenoxine (1-(3-cyano-3,3-diphenylpropyl)-4-phenyl-4-piperidinecarboxylic acid).

Because of its ready availability and demonstrated safety, loperamide HCl is presently most preferred.

Compositions formulated for topical and local administration for treatment and/or prevention of hyperalgesia are also provided. The compositions provided herein, may be formulated for single or multiple dosage administration, and contain an anti-hyperalgesic effective amount (where the amount refers that which is delivered as a single dose) of one or more of the selected compounds in a vehicle formulated for topical or local administration. Generally the compounds are provided in the form of a suspension or emulsion at concentrations of from about 0.1%, preferably from greater than about 1%, particularly when formulated in aqueous medium for application to the nasal passages or lungs, up to 50% or more.

The compositions are formulated as creams, aqueous or non-aqueous suspensions, lotions, emulsions, suspensions or emulsions containing micronized particles, gels, foams, aerosols, solids and other suitable vehicles for application to the skin, eyes, lips and mucosa, as suppositories or creams for vaginal administration, and as combinations with bandages, patches, bioadhesives and dressings. The compounds may be formulated in combination with other agents, such as local anesthetics, vasoconstrictors and other therapeutic agents. The other agents may be mixed in the compositions or provided separately and administered prior to, simultaneously with or subsequent to administration of the compositions provided for the methods herein. Such agents include, but are not limited to: antibiotics, including cephalosporins, β-lactams, tetracyclines, vancomycins, sulfas and aminoglycosides; antivirals, including acylovir; antifungals including clotrimazole; vasoconstrictors; nonsteroidal anti-inflammatories (NSAIs) and steroids.

Methods of treating and/or preventing hyperalgesia by applying an amount of the compositions provided herein effective to ameliorate or eliminate the hyperalgesic state are provided. Thus, methods of treating and/or preventing pain and irritation associated with inflammation following local infection, blisters, boils, or acute skin injuries, such as abrasions, burns, superficial cuts, surgical incisions, toothaches, contusions, irritations, inflammatory skin conditions, including but not limited to poison ivy, and allergic rashes and dermatitis and any condition that yields a hyperalgesic pain state and other such conditions are provided.

Articles of manufacture containing: packaging material, a compound [or compounds] provided herein, which is effective for ameliorating peripheral hyperalgesia within the packaging material, and a label that indicates that the compound, acid, salt or other derivative thereof is used for treating and/or preventing hyperalgesic conditions, are provided.

DETAILED DESCRIPTION OF PREFERRED EMBODIMENTS

Definitions

Figure 1:
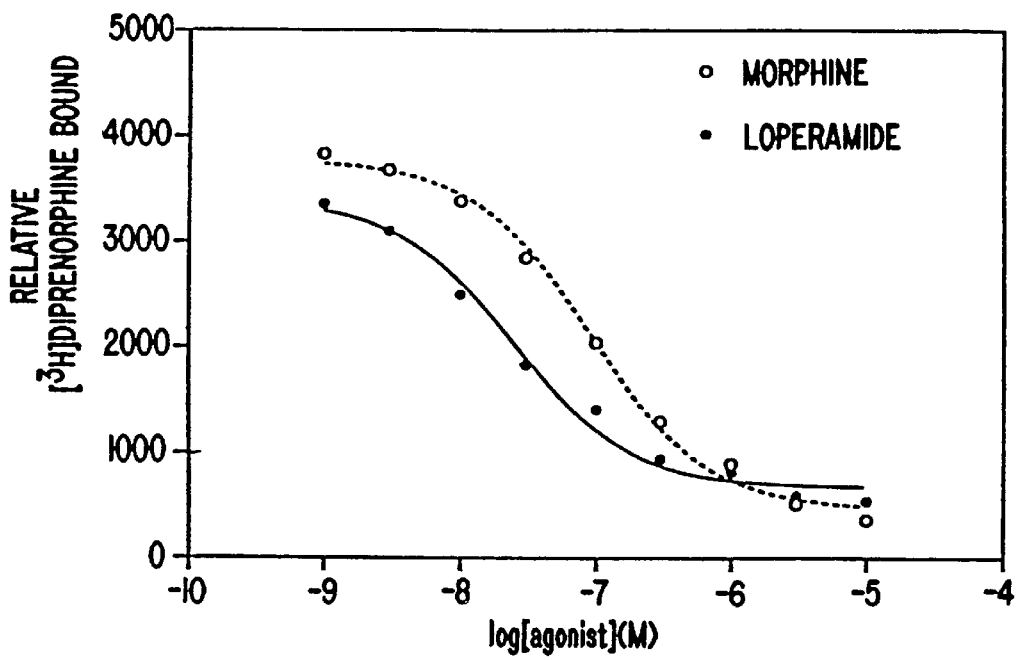
FIG. 1 is a graphical representation of in vitro binding studies involving a compound provided herein and also morphine.

Unless defined otherwise, all technical and scientific terms used herein have the same meaning as is commonly understood by one of skill in the art to which this invention belongs. All patents and publications referred to herein are, unless noted otherwise, incorporated by reference in their entirety.

As used herein, hyperalgesia or a hyperalgesic state refers to a condition in which a warm-blooded animal is extremely sensitive to mechanical, chemical or thermal stimulation that, absent the condition, would be painless. In recent years, it has been shown that after the induction of a local inflammatory state, peripheral afferent terminals, which are otherwise only activated by high intensity stimuli, may develop spontaneous activity [Handwerker et al. (1991) *Pain and inflammation, Proceeding of the VIth World Congress on Pain,* Bond et al. eds, Elsevier Science Publishers BV, pp. 59–70]. Typical models for such a hyperalgesic state include the inflamed rat paw compression model [Stein, et al. (1989) *J. Pharmacol. Exp. Ther.* 248:1269–1275] and they compression of the inflamed knee joint [Sato, et al. (1986) *J. Physiol* 375:611–624]. In these models, it has been shown that the local injection of mu opioids can induce a normalization of the hyperalgesic state. Agents that serve to normalize the sensitized thresholds are behaving as anti-hyperalgesics, rather than as analgesics.

Hyperalgesia is known to accompany certain physical injuries to the body, for example the injury inevitably caused by surgery. Hyperalgesia is also known to accompany certain inflammatory conditions in man such as arthritic and rheumatic disease. Prostaglandins, such as prostaglandin $E_1$ or prostaglandin $E_2$ [hereinafter $PGE_1$ and $PGE_2$ respectively], act to sensitize pain receptors to mechanical or chemical stimulation. Low doses of these prostaglandins can induce the hyperalgesic state. A long-lasting hyperalgesia occurs when $PGE_1$ is infused in man, and the co-administration of $PGE_1$ with a further chemical stimulant, such as bradykinin, causes marked pain that would not be present in the absence of $PGE_1$.

Hyperalgesia, thus refers to mild to moderate pain [and possibly severe pain] such as the pain associated with, but not limited to, inflammatory conditions [such as rheumatoid arthritis and osteoarthritis], postoperative pain, post-partum pain, the pain associated with dental conditions [such as dental caries and gingivitis], the pain associated with burns, including but not limited to sunburns, abrasions, contusions and the like, the pain associated with sports injuries and sprains, inflammatory skin conditions, including but not limited to poison ivy, and allergic rashes and dermatitis, and other such pain that increases sensitivity to mild stimuli. Locally or topically applied or administered anti-hyperalgesic agents do not necessarily abolish pain sensation, but need only restore [or reduce the threshold closer to] the pre-hyperalgesic pain threshold.

As used herein, an agent that acts, directly or indirectly via a receptor or receptors responsible for mediating or involved in peripheral hyperalgesia, by antagonizing the activity of hyperalgesia mediating agents, such as a prostaglandin, is an agent intended for use herein, if it also does not exhibit CNS effects as defined herein. Such agent is a peripheral antihyperalgesic. As intended herein, the activity of antihyperalgesic agents is distinct from the activity of centrally-acting analgesic agents [agents that act by virtue of crossing the blood brain barrier]. Anti-hyperalgesic agents act to block the hypersensitivity. The compositions and methods herein are intended for prevention [i.e., pretreatment] and/or the amelioration of the symptoms [i.e., treatment] of hyperalgesia by decreasing or eliminating the hyperalgesia or by preventing its onset. An antihyperalgesic agent is distinct from a local anesthetic, which is an agent that produces numbness by abolishing sensitivity to touch and other stimuli, including pain stimuli. Local anesthetics abolish sensation, including pain, by blocking conduction in nerve axons in the peripheral nervous system.

Antihyperalgesics, on the other hand, alleviate pain by elevating a patient's threshold to pain. Thus, unlike anesthetics, antihyperalgesics reduce sensation to pain during states of increased sensitivity [hyperalgesia] without substantially affecting normal sensitivity to touch and/or other stimuli.

Antihyperalgesics are agents that may reduce hypersensitivity to touch and other stimuli that would not, under normal circumstances, evoke a pain response. The hyperalgesic response is an exaggerated response, such as excessive sensitiveness or sensibility to pain from touch, slight exertion, warmth and the like. The hyperalgesic state produces a situation in which stimuli that are normally innocuous can produce pain. A particularly striking example is sunburned skin in which severe pain can be produced by a gentle slap on the back or a warm shower. Antihyperalgesics may be identified, for example, by the Randall-Selitto method [see, e.g., Randall et al. (1957) *Arch. Int. Pharmacodyn.* 111:409–419], as well as the formalin, carrageenan and yeast induced inflammation methods. In addition to the antihyperalgesic effect, the antihyperalgesic agents provided herein may concurrently provide an analgesic effect.

Antihyperalgesics may be distinguished from analgesics. Analgesics are agents that may reduce a patient's perception of pain evoked by stimuli that are acutely painful under normal circumstances. Thus, analgesics may be effective in reducing the acute and immediate pain associated with trauma [e.g., pinpricks, burns, or crushing wounds] as well as chronic pain, that is not normally associated with peripheral sensitization, such as cancer or headache pain. Analgesics are typically identified in experiments, such as thermal methods [for example, the hot plate, tail withdrawal or tail flick tests], as compounds that suppress or reduce the evocation of a pain response in an animal model upon exposure to intense heat. Analgesics may also be identified by certain mechanical methods [e.g., the tail clip or tail pinch tests] as compounds that suppress or reduce the evocation of a pain response in a subject [laboratory mouse] upon exposure to intense mechanical pressure. In these standard tests, analgesics may be identified as those compounds that reduce normal sensitivity to an intense, intrinsically painful stimulus.

Central analgesics typically affect the central nervous system, generally via opiate receptors. In preferred form, the antihyperalgesics described herein do not substantially affect the central nervous system.

As used herein, the term peripheral, when used in connection with the term antihyperalgesics, denotes antihyperalgesics that act on the opioid receptor on sensory nerve fibers in the nociceptive (pain) pathways of the peripheral nervous system, as contrasted with the central nervous system.

As used herein, an effective dose or amount of a compound for use herein refers to a concentration or amount that is effective upon topical administration to reduce, including prevent, or ameliorate the hyperalgesic condition and thereby reduce the pain threshold to levels closer to normal or to normal [i.e, the level in the absence of the hyperalgesic condition]. Typically, compounds are provided in compositions that may be formulated for single dosage or multiple dosage administration. The effective concentration is with reference to delivery of an effective amount in a single dose [or in the number of recommended doses].

As used herein, the compounds provided herein, including those of formula (I), also include pharmaceutically acceptable salts, acids and esters thereof, stereoisomers, and also metabolites or prodrugs thereof that possess activity as anti-hyperalgesics but do not cause substantial CNS effects [as defined herein] when topically or locally administered or applied. Metabolites include any compound that is produced upon administration of the compound and metabolism thereof. Thus, loperamide refers to 4-(p-chlorophenyl)-4-hydroxy-N-N-dimethyl-α,α-diphenyl-1-piperidinebutyramide hydrochloride and active metabolites thereof.

As used herein, loperamide and analogs thereof are compounds that have formula (I), below, and active N-oxides and pharmaceutically acceptable salts thereof.

As used herein, local application or administration refers to administration of an anti-hyperalgesic agent to the site, such as an inflamed joint, that exhibits the hyperalgesic condition and that does not exert central analgesic effects or CNS effects associated with systemic administration of opioids that cross the blood brain barrier. Such local application includes intrajoint, such as intra-articular application, via injection, application via catheter or delivery as part of a biocompatible device. Thus, local application refers to application to a discrete internal area of the body, such as, for example, a joint, soft tissue area (such as muscle, tendon, ligaments, intraocular or other fleshy internal areas), or other internal area of the body. In particular, as used herein, local application refers to applications that provide substantially no systemic delivery and/or systemic administration of the active agents in the present compositions. Also, as used herein, local application is intended to refer to applications to discrete areas of the body, that is, other than the various large body cavities (such as, for example, the peritoneal and/or pleural cavities).

As used herein, topical application refers to application to the surface of the body, such as to the skin, eyes, mucosa and lips, which can be in or on any part of the body, including but not limited to the epidermis, any other dermis, or any other body tissue. Topical administration or application means the direct contact of the anti-hyperalgesic with tissue, such as skin or membrane, particularly the cornea, or oral, vaginal or buccal mucosa. Topical administration also includes application to hardened tissue such as teeth and appendages of the skin such as nails and hair. Thus, for purposes herein topical application refers to application to the tissue of an accessible body surface, such as, for example, the skin (the outer integument or covering) and the mucosa (the mucous-producing, secreting and/or containing surfaces). In particular, topical application refers to applications that provide no or substantially no systemic delivery and/or systemic administration of the active compounds in the present compositions. Exemplary mucosal surfaces include the mucosal surfaces of the eyes, mouth (such as the lips, tongue, gums, cheeks, sublingual and roof of the mouth), larynx, esophagus, bronchial, nasal passages, vagina and rectum/anus; in some embodiments, preferably the mouth, larynx, esophagus, vagina and rectum/anus; in other embodiments, preferably the eyes, larynx, esophagus, bronchial, nasal passages, vagina and rectum/anus; and in still other embodiments, preferably the vagina and rectum/anus.

A composition formulated for topical administration may be liquid or semi-solid (including, for example, a gel, lotion, emulsion, cream, ointment, spray or aerosol) or may be provided in combination with a "finite" carrier, for example, a non-spreading material that retains its form, including, for example, a patch, bioadhesive, dressing or bandage. It may be aqueous or non-aqueous; it may be formulated as a solution, emulsion, dispersion, a suspension or any other mixture.

As used herein, a composition refers to a any mixture, including but not limited to, dispersions, emulsions, suspensions, and other other mixtures. It may be a solution, a suspension, liquid, powder, a paste, aqueous, non-aqueous or any combination thereof.

As used herein, a combination refers to any association between two or among more items.

As used herein, a lack of (or without causing) CNS effects or systemic effects, including and particularly CNS effects and CNS-mediated effects, means that the agent preferably exhibits at least about 2-fold less activity in an assay or animal model [particularly those as defined and described herein] for such effects than 2,2-diphenyl-4-[(4-carbethoxy-4-phenyl)piperidino]butyronitrile, generically known as diphenoxylate, which has the formula:

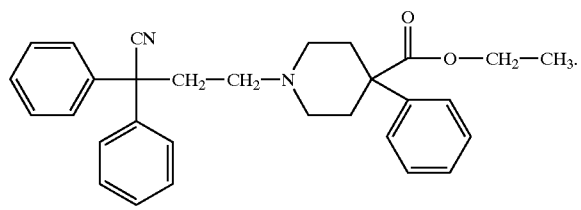

As used herein, the biological activity or bioactivity of a particular compound includes any activity induced, potentiated or influenced by the compound in vivo or in vitro. It also includes the abilities, such as the ability of certain molecules to bind to particular receptors and to induce a functional response. It may be assessed by in vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, N-oxides refer to oxides of one or more nitrogens, preferably the nitrogen on the piperidine ring [see, e.g., formula (I)].

As used herein, substantially pure means sufficiently homogeneous o appear free of readily detectable impurities as determined by standard methods of analysis, such as thin layer chromatography [TLC], mass spectrometry (MS), size exclusion chromatography, gel electrophoresis, particularly agarose and polyacrylamide gel electrophoresis [PAGE] and high performance liquid chromatography [HPLC], used by those of skill in the art to assess such purity, or sufficiently pure such that further purification would not detectably alter the physical and chemical properties, as well as biological activities, of the substance. Methods for purification of the compounds to produce substantially chemically pure compounds are known to those of skill in the art. A substantially chemically pure compound may, however, be a mixture of enantiomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound [see, e.g., Nogrady (1985) *Medicinal Chemistry A Biochemical Approach,* Oxford University Press, New York, pages 388–392].

As used herein, the $IC_{50}$ refers to an amount, concentration or dosage of a particular test compound that achieves a 50% inhibition of a maximal response in an in vitro assay that measures such response.

As used herein, $EC_{50}$ refers to a dosage, concentration or amount of a particular test compound that elicits 50% of maximal expression of a particular dose-dependent response that is induced, provoked or potentiated by the particular test compound in vivo.

As used herein, "halogen" or "halide" or "halo" refers to F, Cl, Br or I, and also pseudohalides. In preferred embodiments halo refers to F, Cl, Br and I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate, azide and trifluoromethyl.

As used herein, carbon chains and carbon chains with heteroatoms, may be straight or branched or, if they contain 3 or more members may be cyclic.

As used herein, alkyl, alkenyl and alkynyl carbon chains, if not specified contain from 1 to 20 carbons, preferably 1 to 12 carbons, and are straight or branched. Alkenyl carbon chains of from 1 to 20 carbons preferably contain 1 to 8 double bonds, and the alkenyl carbon chains of 1 to 12 carbons preferably contain 1 to 4 double bonds. Alkynyl carbon chains of from 1 to 20 carbons preferably contain 1 to 8 triple bonds, and the alkynyl carbon chains of 1 to 12 carbons preferably contain 1 to 4 triple bonds. The alkyl, alkenyl and alkynyl groups may be optionally substituted, with one or more groups, preferably alkyl group substituents that may be the same or different.

As used herein, an alkyl group substituent includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, lower alkyl, lower alkenyl, and lower alkynyl refer to carbon chains having one to about 6 carbons. In preferred embodiments of the compounds provided herein that include alkyl, alkenyl, or alkynyl portions include lower alkyl, lower alkenyl, and lower alkynyl portions. Preferred among lower carbon chains are those having 1–3 carbons.

As used herein, aryl refers to an aromatic carbocyclic radical, preferably containing up to about 16 carbon atoms, more preferably from about 6 to about 10 carbon atoms. The aryl group may be optionally substituted with one or more, preferably one to three, aryl group substituents that may be the same or different.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, arylalkyl, heteroarylalkyl, alkenyl containing 1 to 2 double bonds, alkynyl containing 1 to 2 triple bonds, halo, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfonyl. Exemplary aryl groups include optionally substituted phenyl and optionally substituted naphthyl.

As used herein, cycloalkyl refers to a saturated mono- or multi-cyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents.

As used herein, heteroaryl refers to a monocyclic or multicyclic ring system, preferably of about 5 to about 10 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolinyl and isoquinolinyl, with pyridyl being preferred.

As used herein, heterocyclic refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, alkoxy containing 1 to 4 carbon atoms, halo lower alkyl, including trihalomethyl, such as trifluoromethyl, and halogen. As used herein, the term heterocycle may include reference to heteroaryl. Exemplary heterocycles include, for example, pyrrolidinyl, piperidinyl, alkylpiperidinyl, morpholinyl, oxadiazolyl or triazolyl.

As used herein, wherever $Ar^1$, $Ar^2$, $Ar^3$, and other groups, for example $R^4$, $R^5$, $R^6$ and $R^{17}$ in which ring systems are among alternative embodiments, when such embodiments are specified, among the preferred selections therefor are those in which each is independently selected from a ring system, preferably a 6- to 10-membered ring system, more preferably an aryl ring sytem, or a heteroatom-containg ring system, preferably a 5- to 10-membered heteroatom-containing ring system, more preferably a heteraryl ring system, containing 1 or more heteroatoms, preferably 1 to 3 heteroatoms, such as oxygen, sulfur or nitrogen atoms, wherein the aryl and heteroaryl ring systems are each optionally substituted with one or more, preferably up to three, aryl group substituents [as defined herein], and $Ar^1$ and $Ar^2$ are each preferably independently phenyl or pyridyl, optionally substituted with halo, hydroxy, haloalkyl, preferably halo lower alkyl, particularly trifluoromethyl, alkyl, alkyloxy, aminosulfonyl, alkylcarbonyl, nitro, amino, aminocarbonyl, phenylcarbonyl which is optionally substituted with one or more, preferably up to three, substituents selected from halo, halo alkyl and alkyl, or thienyl which is optionally substituted with halo, haloalkyl or alkyl, where the alkyl groups are straight or branched chain and preferably contain from 1 to 6 carbons, more preferably 1 to 3 carbons.

As used herein, the nomenclature alkyl, alkoxy, carbonyl, etc. are used as is generally understood by those of skill in this art. For example, as used herein alkyl refers to non-aromatic carbon chains that contain one or more carbons; the chains may be straight or branched or include cyclic portions or be cyclic. As used herein, alicyclic refers to alkyl groups that are cyclic.

As used herein, "haloalkyl" refers to an alkyl radical, preferably lower alkyl, in which one or more of the hydrogen atoms are replaced by halogen including, but not limited to, chloromethyl, trifluoromethyl, 1-chloro-2-fluoroethyl and other such groups. Halo lower alkyl refers to lower alkyl substituted with one or more halo substituents, and is preferably trichloromethyl or trifluoromethyl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is alkyl, preferably lower alkyl.

As used herein, "dialkylaminocarbonyl" refers to —C(O)NR'R in which R' and R are independently selected from alkyl, preferably lower alkyl; "carboxamide" refers to groups of formula RCONH$_2$, where R is alkyl or aryl.

As used herein, "diarylaminocarbonyl" refers to —C(O)NRR' in which R and R' are independently selected from aryl, preferably lower aryl, more preferably phenyl.

As used herein, "arylalkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "thioalkoxy" refer to RO— and RS—, in which R is alkyl, preferably lower alkyl.

As used herein, "aryloxy" and "thioaryloxy" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), —(CH$_2$)$_n$—N(R)—(CH$_2$)$_m$—, where each of m and n is independently an integer from 0 to 30 and R is hydrogen or alkyl, methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 1 to about 20 carbon atoms and at least one double bond, more preferably 1 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and —CH═CH—CH$_2$—. The term "lower alkenylene" refers to alkenylene groups having 2 to 6 carbons. Preferred alkenylene groups are lower alkenylene, with alkylene of 3 to 4 carbon atoms being particularly preferred.

As used herein, when any particular group, such as phenyl or pyridyl, is specified, this means that the group is unsubstituted or is substituted. Preferred substituents where not specified are halo, halo lower alkyl, and lower alkyl.

As used herein, the abbreviations for any protective groups, amino acids, including non-naturally occurring and amino acid analogs, and other compounds, are, unless indicated otherwise, in accord with their common usage, recognized abbreviations, or the IUPAC-IUB Commission on Biochemical Nomenclature [see, (1972) *Biochem.* 11:942–944]. Each naturally or non-naturally occurring L-amino acid is identified by the standard three letter code or the standard three letter code with the prefix "L-"; the prefix "D-" indicates that the enantiomeric form of the amino acid is D.

A. Compounds

In animal models, it is demonstrated herein that the local injection of compounds that directly or indirectly agonize at least one of the $\mu$ and/or $\kappa$ and/or $\delta$, preferably $\mu$ and/or $\kappa$, peripheral receptors induces a normalization of the hyperalgesic state. This peripheral action of opiates in reducing the hyperalgesic state is of value, but traditional opiates, such as morphine, meperidine and fentanyl cross the blood-brain barrier allowing for the appearance of systemically and CNS mediated undesirable side effects. To solve these problems, the compositions provided herein contain compounds that exhibit activity as peripheral anti-hyperalgesics, but do not exhibit substantial CNS effects as determined in suitable animal models as described herein. Intended for use in the methods and compositions herein are any compounds that, by virtue of indirect or direct μ or κ or δ, preferably μ or κ, more preferably μ, agonist activity, act as peripheral anti-hyperalgesics but that, upon local or topical administration, are substantially devoid [as defined herein] of CNS-mediated analgesic and other activities. Such compounds are typically anti-diarrheal compounds, as assessed in standard assays, that exhibit low or no activity in assays that assess CNS activity. In particular, such a compound is one that:

(1) has activity as a peripheral anti-hyperalgesic as assessed in any recognized in vivo or in vitro model or assay; and, substantially no CNS-mediated effects, which are preferably assessed by selecting compounds that have (2) either:
  (a) a B/A ratio greater than or equal to diphenoxylate and a B value at least about 2-fold greater than diphenoxylate, or
  (b) has a B/A ratio greater, at least about equal to, prefearbly about 2-fold, [among the preferred compounds ratios greater than about 3-fold may be observed] than diphenoxylate, where:
    B is the $ED_{50}$ of the compound in an assay [the well known tail clip assay, tail flick assay or hot plate assay, described below and known to those of skill in this art] that measures CNS activity of the compound, the
    A is the $ED_{50}$ of the compound in an assay that measures anti-diarrheal activity of the compound. The assay in which anti-diarrheal activity is measured is the Castor oil test or the assay that measures antagonism of $PGE_2$-induced diarrhea in mice, described below [see, also, Dajani et al. (1977) *J. Pharmacol. Exp. Ther.* 203:512–526, Dajani et al. (1975) *European Jour. Pharmacol.* 34:105–113; U.S. Pat. Nos. 4,870,084; 4,066,654, 4,057,549; 3,950,537; 3,998,832, 3,996,214]. The relative activities of the compound of interest are compared to the activities of diphenoxylate in the same assays. It is understood that the assays are art-recognized assays such that diphenoxylate activity serves as an accurate standard.

Of particular interest herein are compositions that are formulated, at concentrations effective for reducing, alleviating or eliminating, hyperalgesic pain, for topical or local administration and contain one or more compounds of formula (I) or N-oxides, preferably an N-oxide of a piperidine-nitrogen, thereof or other pharmaceutically acceptable derivatives thereof:

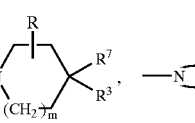

in which:
  m is an integer from 0 to 3, preferably 1 to 3, more preferably 1 or 2, and most preferably 2;

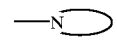

is an azabicycloalkyl containing from 6 to 9 carbon atoms with at least 5 atoms in each ring, which ring is preferably pyrrolidino, piperidino, or hexamethylenimino, where the tertiary amine is:

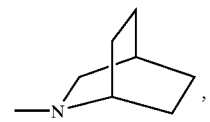

and is unsubstituted or substituted with $OR^{18}$ in which $R^{18}$ is hydrogen or lower alkanoyl containing 2 to 7, preferably 2 or 3, carbon atoms, and $OR^{18}$ is preferably attached at the 5 position in 5-membered rings or the 5 or 6 position in 6-membered rings and is attached in the endo or exo configuration, where $R^3$, $R^7$, $R^5$ and $R^6$ are as defined below. The tertiary amine is preferably:

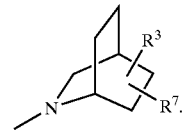

M is more preferably selected from among:

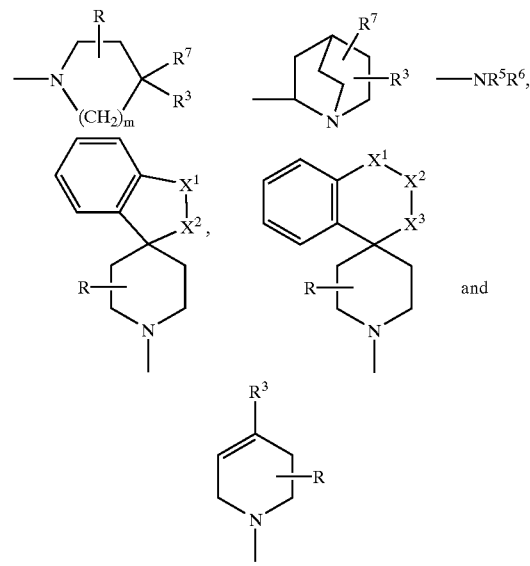

where
  m is an integer from 1 to 3, preferably 1 or 2, more preferably 2; and
  $X^1$, $X^2$ and $X^3$ are —$C(R^{24})(R^{25})$—, —$C(R^{24})$═$C(R^{25})$—, —$C(R^{24})$═N—, —N═$C(R^{24})$—, —$C$(═O)—, —O—, —S— or —$N(R^{24})$—, with the proviso that only one of $X^1$, $X^2$ and $X^3$ may be O, S or $NR^{24}$; and
  $R^{24}$ and $R^{25}$ are hydrogen or lower alkyl.
  $Ar^1$ and $Ar^2$ are either (i) or (ii) as follows:
    (i) each is independently selected from an aryl ring system (preferably a 6- to 10-membered aryl ring system) or a heteroaryl ring system (preferably a 5- to 10-membered heteroaryl ring system) containing 1 or more heteroatoms, preferably 1 to 3 heteroatoms, such as oxygen, sulfur or nitrogen atoms, where the aryl and heteroaryl ring systems are each optionally substituted with one or more (preferably up to three) aryl group substituents, and $Ar^1$ and $Ar^2$ are each preferably independently phenyl or pyridyl, optionally substituted with halo, hydroxy, haloalkyl, preferably halo lower alkyl, particularly trifluoromethyl, alkyl, alkyloxy, aminosulfonyl, alkylcarbonyl, nitro, amino, aminocarbonyl, phenylcarbonyl which is optionally substituted with one or more (preferably up to three) substituents selected from halo, halo alkyl and alkyl, or thienyl which is optionally substituted with halo, haloalkyl or alkyl, where the alkyl groups are straight or branched chain and preferably contain from 1 to 6 carbons, more preferably 1 to 3 carbons; or (ii) $Ar^1$ and $Ar^2$ are each independently phenyl or pyridyl groups, which are unsubstituted or substituted with, preferably aryl substituent groups, as defined herein, preferably phenyl, and with the carbon to which they are commonly linked form a fused ring system, so that the compounds of formula (I) have the structure:

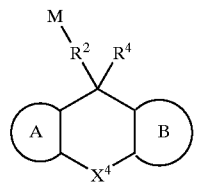

and is preferably,

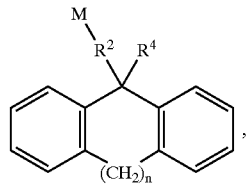

where:

A and B are independently selected from phenyl and pyridyl, preferably phenyl, which are unsubstituted or substituted, preferably with up to three aryl group substituents;

$X^4$ is a direct bond, $-(CH_2)_n-$, $-CH=CH-$, $-CH=CHCH_2-$, $-(CH_2)_pO(CH_2)_q-$, $-(CH_2)_pS(O)_r(CH_2)_q-$, $-(CH_2)_pNR^{21}(CH_2)_q-$ or

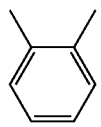

n is an integer from 0 to 3, preferably 1 to 3, and more preferably 2 or 3;

$R^{21}$ is hydrogen or lower alkyl;

each of p and q is 0 or 1, and the sum of p and q is no greater than 2;

r is 0 to 2;

$R^2$ is a direct bond, or is alkylene in which the alkyl group is a straight or branched chain, preferably is alkylene containing from 1 to 12, preferably 1 to 6, more preferably 1 to 3 carbons and most preferably is $-(CH_2)_2-$ or $-CH_2CH(CH_3)-$, is alkenylene having 2 to 6 carbon atoms, preferably 2 to 3 carbons atoms, and one or two, preferably one, double bond, or is alkynylene having 2 to 6 carbon atoms, preferably 2 to 3 carbons atoms, and one or two triple bond, in all instances the chains are unsubstituted or substituted, and, if substituted, preferably with one or more hydroxy groups;

$R^3$ is selected from $Ar^3$, $-Y-Ar^3$, where Y is alkylene or alkenylene having, preferably, 2 to 4 carbon atoms; alkenyl containing 2 to 4 carbons; cycloalkyl containing 3 to 8 carbons; heterocycle, preferably 1-pyrrolidinyl, 1-piperidinyl, 1-hexamethyleneiminyl, 1-morpholinyl or $-N(Ar^4)-R^{23}$, where $R^{23}$ is alkyl; alkenyl; alkanoyl which is optionally substituted, preferably with halo, hydroxy or alkoxy, preferably lower alkanoyl; alkenoyl having 3 to 10 carbons and 1 to 3 double bonds; optionally substituted aroyl, preferably benzoyl; heteroaroyl, preferably pyridoyl, furoyl and thienoyl; alkoxycarbonyl, preferably lower alkoxycarbonyl; alkenyloxycarbonyl having 3 to 10 carbons and 1 to 3 double bonds; aryloxycarbonyl, preferably phenoxycarbonyl; formyl ($-CHO$); cyano; aminocarbonyl ($-CONH_2$); alkylaminocarbonyl; dialkylaminocarbonyl, arylaminocarbonyl, diarylaminocarbonyl or arylalkylaminocarbonyl; or

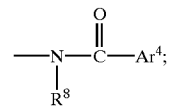

$R^8$ is hydrogen or alkyl that is a straight or branched chain, preferably containing from 1 to 6, more preferably 1 to 3, carbon atoms;

$Ar^3$ is an aryl ring system, preferably a 6- to 10-membered aryl ring system, or a heteroaryl ring system, preferably a 5- to 10-membered heteroaryl ring system, containing 1 or more heteroatoms, preferably 1 to 3 heteroatoms, such as oxygen, sulfur or nitrogen atoms, in the aryl and heteroaryl ring systems are each unsubstituted or substituted with one or more, preferably up to three, substitutents, preferably aryl group substituents halo, halo lower alkyl or lower alkyl, and $Ar^3$ is preferably phenyl or pyridyl unsubstituted or substituted with halo, halo lower alkyl or lower alkyl;

$Ar^4$ is either:

(i) heterocycle containing 1 ring or 2 or more fused rings, preferably 1 ring or 2 to 3 fused rings, where each ring contains 1 or more, preferably 1 to 3 heteroatoms, and preferably contains 4 to 10 members, more preferably 5 to 7 members, and is optionally substituted with one or more, preferably up to three, aryl group substituents, preferably halo, halo lower alkyl or lower alkyl, and $Ar^4$ is preferably selected from heterocycles that include, but are not limited to, indolyl, benzofuranyl, benzothienyl, isoquinolinyl, quinolinyl, benzimidazoly, thienyl, furanyl, pyridinyl, thiazolyl and imidazolyl, each of which is optionally substituted, preferably with halo, halo lower alkyl or lower alkyl, preferably halo, and the heterocycle is more preferably selected from thienyl, furanyl, pyridinyl, thiazolyl and imidazolyl; or (ii) a radical of formula:

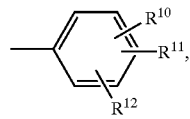

in which:
$R^{10}$, $R^{11}$ and $R^{12}$ are each independently selected from hydrogen, alkyloxy, alkoxyalkyl, halo, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkynyloxy, arylalkyloxy, aryloxy and alkyl, in which alkyl, alkenyl, alkynyl or aryl group defined by $R^{10}$, $R^{11}$ and $R^{12}$ is unsubstituted or substituted with one or more, preferably 1 to 4 substituents selected from halo, halo alkyl, preferably halo lower alkyl, or alkyl, preferably lower alkyl,, and the alkyl groups are straight or branched chains that are preferably lower alkyl ($C_{1-6}$) and more preferably $C_{1-3}$ or (iii) 1- or 2-naphthyl, dihydronaphthyl, tetrahydronaphthyl, indenyl or dihydroindenyl, each of which is optionally substituted with one or more aryl group substituents;

R is halo, haloalkyl, preferably lower halo alkyl, or alkenyl having 3 to 12 carbons, preferably lower alkenyl or hydroxy and is preferably at the 3-position [relative to the N], more preferably a 3-halo or 3-lower alkyl, or R is $OR^9$ that is preferably at the 3-position so that the piperidinyl ring has the formula:

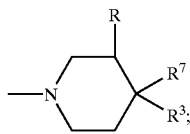

$R^9$ is selected from hydrogen, alkyl, arylalkyl, alkylcarbonyl, aminoalkyl, alkylaminoalkyl, dialkylaminoalkyl, in which the alkyl groups are straight or branched chains and preferably contain 1 to 12, more preferably 1 to 6 carbons, more preferably 1–3 carbons in the chain;

$R^4$ is selected from among:
(i) an aryl ring system, preferably a 6- to 10-membered aryl ring system, or a heteroaryl ring system, preferably a 5- to 10-membered heteroaryl ring system, containing 1 or more heteroatoms, preferably 1 to 3 heteroatoms, such as oxygen, sulfur or nitrogen atoms, in which the aryl and heteroaryl ring systems are each optionally substituted with one or more, preferably up to three aryl group substituents, and $R^4$ is preferably phenyl or pyridyl which is optionally substituted with lower alkyl, halo or halo lower alkyl, with phenyl being even more preferred, or
(ii) a heterocyclic ring containing one to three heteroatoms, that is unsubstituted or substituted with halo, halo lower alkyl or lower alkyl, and is preferably a pyrrolidinyl, oxadiazolyl or triazolyl radical, more preferably oxadiazolyl, most preferably 1,3,4-oxadiazolyl, particularly a 5-substituted 1,3,4-oxadiazolyl in which the substituent is halo, halo lower alkyl, hydroxy, lower alkoxy or lower alkyl, or
(iii) alkyl containing 1 to 8 carbons which is optionally substituted with hydroxy or alkylcarbonyloxy (—OCOR), preferably 1 to 6 carbons, more preferably 1 to 3 carbons; alkenyl containing 3 to 6 carbons; cycloalkylalkyl in which the cycloalkyl contains 3 to 8 carbons and the alkyl contains 1 to 3 carbons; cycloalkenylalkyl in which the cycloalkenyl contains 3 to 8 carbons and the alkyl contains 1 to 3 carbons; or (iv)

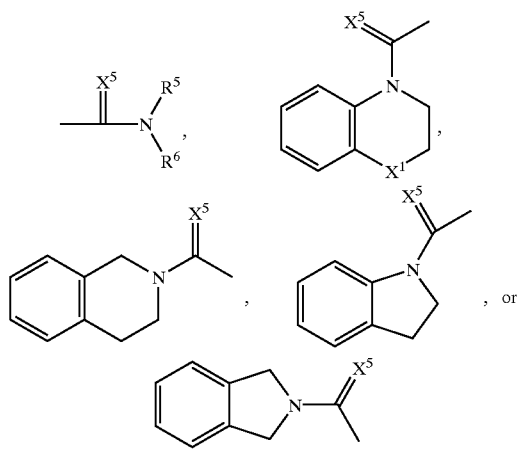

where
$X^1$ is as previously defined;
$X^5$ is O or S;
$R^5$ and $R^6$ are either:
(a) independently selected from hydrogen, alkyl that is a straight or branched chain containing 1 to 12, preferably 1 to 6 carbons, more preferably 1–3 carbons, alkenyl or alkynyl that is straight or branched chain, containing 2 to 12, preferably containing 3–6 carbons and one or two double or triple bonds, or aryl, preferably a 6- to 10-membered aryl ring system that is optionally substituted with one or more, preferably up to three, aryl group substituents, or arylalkyl, and each is preferably 2-propenyl, ethyl, methyl or aryl, preferably phenyl or phenylmethyl, or
(b) $R^5$ and $R^6$ are each independently selected from carbon chains, heteroatoms, and carbon chains containing one or more heteroatoms, so that together with the nitrogen atom to which each is attached, they form a 3- to 10-, preferably 4–7, more preferably 5 to 6-membered heterocyclic ring containing one to three heteroatoms, that is preferably a piperidinyl, alkylpiperidinyl, morpholinyl, oxadiazolyl, triazolyl or pyrrolidinyl radical that is unsubstituted or substituted with halo, halo lower alkyl, hydroxy or lower alkoxy or lower alkyl, and is more preferably a 1,3,4-oxadiazolyl, 4-morpholinyl, or di($C_1$–$C_6$ alkyl)-morpholinyl, preferably 2,6-di($C_1$–$C_6$ alkyl)-4-morpholinyl, radical;
(v) cyano, formyl, alkoxycarbonyl, aryloxycarbonyl, alkylcarbonyl or arylcarbonyl;

(vi) —NR$^5$COR$^5$; or
(vii) —S(O)$_r$alkyl or —S(O)$_r$ aryl, where r is 1 or 2; and R$^7$ is selected from among:
—H;
OH;
—R$^{14}$OR$^{13}$ in which R$^{13}$ is hydrogen, lower alkyl, preferably containing 1 to 4 carbons, or alkanoyl containing 2 to 5, preferably 2 or 3, carbon atoms, and R$^{14}$ is lower alkylene, preferably alkylene of 1 to 4 carbon atoms, more preferably methylene or ethylene, or R$^{14}$ is alkenylene of 2 to 6 carbon atoms;
—CH$_2$NR$^{15}$R$^{16}$ in which R$^{15}$ is hydrogen, lower alkyl, lower alkanoyl, aryl or aroyl, and R$^{16}$ is hydrogen or lower alkyl or, together with the nitrogen atom to which they are attached, R$^{15}$ and R$^{16}$ form a 3 to 7-membered ring which optionally contains an additional heteroatom selected from oxygen, nitrogen or sulfur;
—OR$^{15}$;
—C(O)H;
—CN;
—C(=O)NR$^5$R$^6$ in which R$^5$ and R$^6$ are as previously defined;
alkyl, preferably lower alkyl;
aryl, preferably phenyl;
—C(O)OR$^{17}$ in which R$^{17}$ is hydrogen, alkyl containing from 1 to 7 carbon atoms, alkenyl having 3 to 7 carbon atoms, an optionally substituted aryl ring system (preferably a 6 to 10-membered aryl ring system), an optionally substituted heteroaryl ring system (preferably a 5 to 10-membered heteroaryl ring system) containing 1 or more heteroatoms, preferably 1 to 3 heteroatoms, such as oxygen, sulfur or nitrogen atoms, alkylaryl, arylalkyl, preferably benzyl, phenethyl, phenylpropyl or phenylbutyl, heteroarylalkyl, preferably furylmethyl, thienylethyl or pyridylpropyl, particularly pyridyl, phenyl, tolyl, ethylphenyl, butylphenyl or halophenyl, or a pharmaceutically acceptable cation, such as an alkali metal or alkaline earth metal, including sodium, potassium, calcium and ammonium cations;

where the optional aryl group substituents are selected from halo, alkyl, cycloalkyl, cycloalkylalkyl, aryl, heteroaryl, arylalkyl, heteroarylalkyl, alkenyl containing 1 to 2 double bonds, alkynyl containing 1 to 2 triple bonds, haloalkyl and polyhaloalkyl, especially trifluoromethyl, formyl, alkylcarbonyl, arylcarbonyl, heteroarylcarbonyl, carboxy, alkoxycarbonyl, aryloxycarbonyl, aminocarbonyl, alkylaminocarbonyl, dialkylamino-carbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfonyl.

In certain embodiments herein, when Ar$^3$ is 1-(3-propionyl-2-imidazolinon)yl, then R$^4$ is other than —CN. Also in certain embodiments herein, when R$^4$ is —C(=X$^5$)—NR$^5$R$^6$, X$^5$ is O and R$^5$ and R$^6$, together with the nitrogen atom to which they are attached form pyrrolidinyl, then M is other than 4-morpholinyl. In yet other certain embodiments, when M is —NR$^5$R$^5$ and R$^5$ and R$^5$ are methyl, then R$^4$ is other than 1-hydroxypropyl (CH$_3$CH$_2$CH(OH)—) or ethylcarbonyl (CH$_3$CH$_2$C(=O)—). In still other certain embodiments, when M is 4-morpholinyl or 1-piperidinyl, then R$^4$ is other than ethylcarbonyl (CH$_3$CH$_2$C(=O)—). In certain other embodiments, when M is 4-morpholinyl, than R$^4$ is other than ethoxycarbonyl (CH$_3$CH$_2$OC(=O)—).

Also intended for use herein are salts of the compounds of formula (I), including salts with pharmaceutically acceptable acids and quaternary ammonium salts, N-oxides of the compounds of formula (I) and salts thereof, including salts with pharmaceutically acceptable acids and quaternary ammonium salts, including stereoisomeric forms of quaternary ammonium salts, prodrugs of the compounds of formula (I), and metabolites of the compounds of formula (I), including, for example, glucuronides.

Among the suitable quaternary ammonium salts of the compounds of formula (I), are for example, compounds of the following formulae:

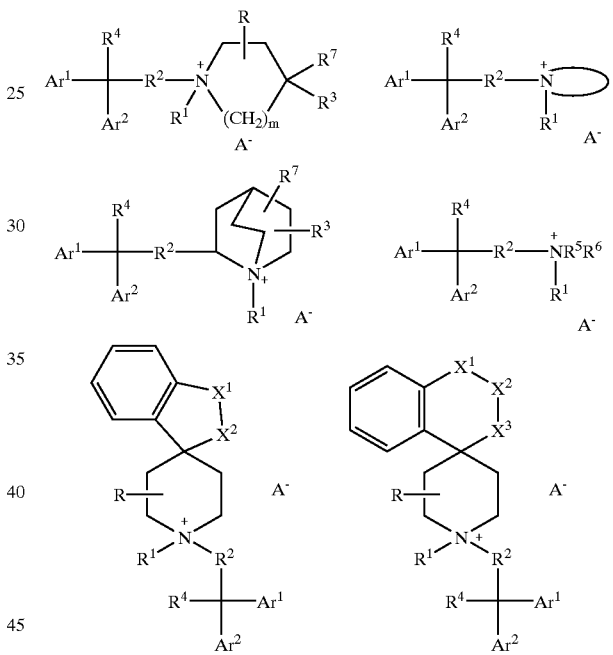

in which:

R$^1$ is alkyl of 1 to 12 carbons which is optionally substituted with 1 to 6 halo atoms, 1 to 3 hydroxy groups or 1 to 3 alkoxy groups; alkenyl of 3 to 12 carbons which contains 1 to 3 double bonds and is optionally substituted with 1 to 6 halo atoms; alkynyl of 3 to 12 carbons which contains 1 to 3 triple bonds and is optionally substituted with 1 to 6 halo atoms; arylalkyl where the alkyl chain contains 1 to 6 carbons and the aryl group contains 6 to 10 carbons, preferably phenyl, and is optionally substituted with 1 to 3 aryl group substituents; arylalkenyl where the alkenyl chain contains 3 to 6 carbons and 1 to 3 double bonds and the aryl group contains 6 to 10 carbons, preferably phenyl, and is optionally substituted with 1 to 3 aryl group substituents; arylalkynyl where the alkynyl chain contains 3 to 6 carbons and 1 to 3 triple bonds and the aryl group contains 6 to 10 carbons, preferably phenyl, and is optionally substituted with 1 to 3 aryl group substituents; cycloalkyl of 3 to 8 carbons; cycloalkenyl of 3 to 8 carbons; cycloalkylalkyl in which the cycloalkyl group contains 3 to 8 carbons and the alkyl chain contains 1 to 6 carbons; cycloalkenylalkyl in which the cycloalkenyl group contains 3 to 8 carbons and the alkyl chain contains 1 to 6 carbons;

A is halo, hydroxy, alkoxy of 1 to 12 carbons, alkanoyloxy of 1 to 12 carbons or aroyloxy, preferably benzoyloxy, or any other pharmaceutically acceptable group that is capable of forming a counterion in a quaternary ammonium salt; and m, $X^1$, $X^2$, $X^3$, R, $R^2$, $R^3$, $R^4$, $R^5$, $R^6$, $R^7$, $Ar^1$ and $Ar^2$ are as previously defined.

Preferred among the compounds of formula (I) are those of formula (II) or N-oxides thereof and other pharmaceutically acceptable derivatives:

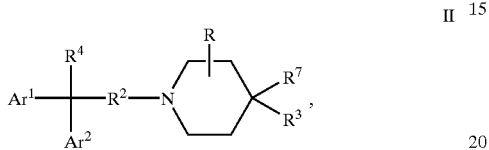

where:

$Ar^1$ and $Ar^2$ are each independently selected from an aryl ring system, preferably a 6- to 10-membered aryl ring system, and a heteroaryl ring system, preferably a 5- to 10-membered heteroaryl ring system, containing 1 or more heteroatoms, preferably 1 to 3 heteroatoms, such as oxygen, sulfur or nitrogen atoms, where the aryl and heteroaryl ring systems are each optionally substituted with one or more, preferably one to three, aryl group substituents, and is preferably phenyl or pyridyl optionally substituted with halo, halo alkyl, preferably halo lower alkyl, particularly trifluoromethyl, hydroxy, alkyl, alkyloxy, aminosulfonyl, alkylcarbonyl, nitro, amino, aminocarbonyl, phenylcarbonyl that is optionally substituted with 1 or more, preferably 1 to 3, substituents selected from halo, halo lower alkyl and alkyl, or thienyl which is optionally substituted with 1 or more, preferably 1 to 3, substituents selected from halo, haloalkyl or alkyl, in which the alkyl groups are substituted with halo, haloalkyl or alkyl, in which the alkyl groups are straight or branched chains that contain 1 to 12 carbons, preferably are lower alkyl, more preferably containing 1 to 3 carbons;

$R^3$ is $Ar^3$ or

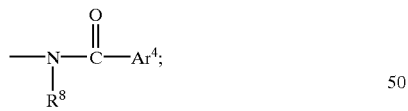

$Ar^3$ is an aryl ring system, preferably a 6- to 10-membered aryl ring system, or a heteroaryl ring system, preferably a 5- to 10-membered heteroaryl ring system, containing 1 or more, preferably 1 to 3, heteroatoms, such as oxygen, sulfur or nitrogen atoms, where the aryl and heteroaryl ring systems are each optionally substituted with one or more, preferably up to 3, aryl group substituents, and is preferably phenyl or pyridyl optionally substituted with halo, halo lower alkyl or lower alkyl;

$Ar^4$ is thienyl, furanyl, pyridinyl, thiazolyl, imidazolyl, each of which is unsubstituted or substituted with 1 or more, preferably 1 to 3, aryl group substituents, preferably halo or halo, lower alkyl, or $Ar^4$ is a radical of formula:

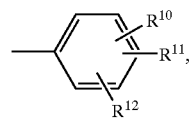

in which $R^{10}$, $R^{11}$ and $R^{12}$ are each independently selected from hydrogen, alkyl, alkyloxy, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, $C_{3-6}$alkynyloxy, arylalkyloxy, aryloxy and alkyl, in which each group is unsubstituted or substituted with up to 4 substituents selected from halo atoms, lower alkyl or halo lower alkyl, and the alkyl groups are straight or branched chains that are preferably lower alkyl, and more preferably $C_{1-3}$;

$R^2$ is alkylene in which the alkylene group is a straight or branched chain containing 1 to 12 carbon atoms, preferably lower alkylene, more preferably containing 1 to 3 carbon atoms and most preferably is —(CH$_2$)$_2$— or —CH$_2$CH(CH$_3$)— or alkynylene containing 1 to 12 carbon atoms, preferably lower alkynylene, more preferably containing 1 to 3 carbon atoms;

R is hydrogen, alkyl, preferably lower alkyl, halo or haloalkyl, and is preferably at the 3-position [relative to the N] is more preferably a 3-lower alkyl, or R is O$R^9$ that is preferably in the 3-position;

$R^9$ is selected from hydrogen, alkyl, arylalkyl, alkylcarbonyl, aminoalkyl, alkylaminoalkyl, dialkylaminoalkyl, in which the alkyl groups are straight or branched chains, preferably containing 1 to 6 carbon atoms, more preferably 1 to 3 carbon atoms in the chain;

$R^4$ is phenyl, pyridyl, cyano or

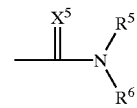

where $X^5$ is O or S;

$R^5$ and $R^6$ are either:
(i) independently selected from hydrogen, aryl, alkyl, that is a straight or branched chain containing 1 to 6, preferably 1 to 3 carbons, alkenyl that is straight or branched chain, preferably containing 2 to 6 carbons and 1 or 2 double bonds, more preferably containing 1 to 4 carbons and 1 double bond, and is more preferably 2-propenyl, aryl, preferably phenyl or arylalkyl, preferably phenylmethyl, or
(ii) $R^5$ and $R^6$, together with the nitrogen atom to which each is attached form a 3- to 10-, preferably 4- or 7-, more preferably 5 or 6-, membered heterocyclic ring containining one to three heteroatoms, that is preferably selected from pyrrolidinyl, piperidinyl, alkylpiperidinyl, morpholinyl, oxadiazolyl or triazolyl radical, each of which is unsubstituted or substituted with one or more substituents selected from halo, halo lower alkyl or lower alkyl, and is more preferably 1,3,4-oxadiazolyl, particualry a 5-substituted 1,3,4-oxadiazolyl in which the substituent is halo, halo lower alkyl, hydroxy, lower alkoxy or lower alkyl, a 4-morpholinyl or di($C_1$–$C_6$ alkyl)-morpholinyl, preferably 2,6-di($C_1$–$C_6$ alkyl)-4-morpholinyl;

$R^7$ is —H, —OH, —C(O)O$R^{17}$ in which $R^{17}$ is hydrogen, alkyl, preferably lower alkyl, more preferably methyl, ethyl or propyl, or aryl, preferably phenyl, —C(O)H— or —$R^{14}$O$R^{13}$ in which $R^{13}$ is hydrogen or lower alkyl, preferably containing 1–4 carbons, or is an alkanoyl containing 2 to 5, preferably 2 or 3 carbon atoms, and $R^{14}$ is lower alkylene, preferably methylene or ethylene, or $R^{14}$ is alkenylene; and $R^8$ is hydrogen or alkyl that is a straight or branched chain containing from 1 to 6, preferably 1 to 3, carbon atoms.

In more preferred embodiments all alkyl groups contain from 1 to 3 carbon atoms; R is hydrogen or methyl, $R^4$ is —CN or

in which:

$X^5$ is as previously defined $R^5$ and $R^6$ are each independently hydrogen, straight or branched chain alkyl, alkenyl, preferably methyl, ethyl or propyl, or phenyl, or $R^5$ and $R^6$ together with the nitrogen to which each is attached form pyrrolidinyl, piperidinyl or morpholinyl that is preferably unsubstituted, and more preferably where $R^7$ is OH or —C(O)O$R^{17}$ in which $R^{17}$ is hydrogen or methyl, ethyl or propyl which is branched or straight chain, and $R^3$ is $Ar^3$, preferably phenyl, more preferably halo-substituted phenyl.

Among preferred compounds of formula (I) are those of formula (III) or N-oxides thereof and other pharmaceutically acceptable derivatives:

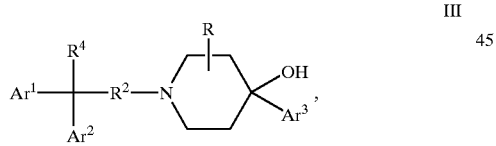

III in which:

$Ar^1$ and $Ar^2$ are each independently selected from an aryl ring system, preferably a 6- to 10-membered aryl ring system, and a heteroaryl ring system, preferably a 5- to 10-membered heteroaryl ring system, containing 1 or more heteroatoms, preferably 1 to 3 heteroatoms, and $Ar^1$ and $Ar^2$ are preferably independently phenyl or pyridyl, where the aryl and heteroaryl ring systems are each unsubstituted or substituted with up to three aryl group substituents, preferably selected from halo, haloalkyl or alkyl in which the alkyl groups are straight or branched chains and preferably are lower alkyl containing from 1–6 carbons, more preferably 1–3 carbons;

$R^2$ is alkylene, alkenylene containing one double bond, where the carbon chain in the alkylene or alkenylene group is a straight or branched chain, in which the alkylene group, preferably contains from 1 to 6, more preferably 1 to 3, carbons, alkynylene containing one triple bond, where the carbon chain in the alkylene, alkenylene or alkynylene group is a straight or branched chain, in which the alkylene group, preferably contains from 1 to 6, more preferably 1 to 3, carbons;

R is hydrogen, alkyl, preferably lower alkyl, halo or halo lower alkyl, and the alkyl group preferably contains 2 to 6 carbons, more preferably 2 to 3 carbons; and most preferably is a 3-lower alkyl or hydrogen;

$R^4$ is:

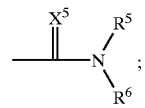

where:

$X^5$ is as previously defined $R^5$ and $R^6$ are either:
(i) independently selected from hydrogen or alkyl, alkenyl, or alkynyl which may be a straight or branched chain, and each is preferably lower alkyl, more preferably methyl or ethyl, or
(ii) $R^5$ and $R^6$, together with the nitrogen atom to which each is attached, form a 3 to 7, preferably 5 or 6, membered carbon ring or heterocyclic ring containing one or two heteroatoms, that is preferably a pyrrolidinyl, piperidinyl, alkylpiperidinyl, morpholinyl, preferably 4-morpholinyl, or di($C_1$–$C_6$ alkyl)-morpholinyl, preferably 2,6-di ($C_1$–$C_6$ alkyl)-4-morpholinyl, radical; and $Ar^3$ is an aryl ring system, preferably a 6- to 10-membered aryl ring system or a heteroaryl ring system, preferably a 5- to 10-membered heteroaryl ring system, containing 1 or more, preferably 1 to 3 heteroatoms, such as oxygen, nitrogen or sulfur atoms, more preferably phenyl or pyridyl, where the aryl and heteroaryl ring systems are each unsubstituted or substituted with up to three aryl group substituents, preferably selected from halo, halo lower alkyl and lower alkyl.

Of the compounds of formula (II), the compounds of formula (IV) are particularly preferred:

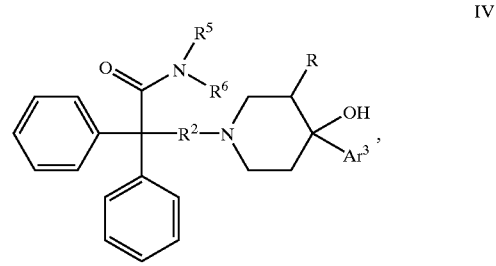

IV in which $Ar^3$ is phenyl that is unsubstituted or preferably substituted with halo or halo lower alkyl, preferably 4-halo. More preferred are those compounds in which $R^2$ is —$(CH_2)_2$—.

In other embodiments, the compounds of formula (I) are those having formula (V) [see, e.g., U.S. Pat. No. 4,990,521] or N-oxides thereof and other pharmaceutically acceptable derivatives:

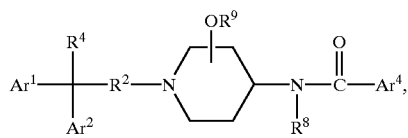

V in which:
- $Ar^1$ and $Ar^2$ are each independently selected from an aryl ring system, preferably a 6- to 10-membered aryl ring system, and a heteroaryl ring system, preferably a 5- to 10-membered heteroaryl ring system, containing 1 or more, preferably 1 to 3, heteroatoms, such as oxygen, sulfur or nitrogen atoms, where the aryl and heteroaryl ring systems are each optionally substituted with 1 or more, preferably 1 to 3 aryl group substituents, and is preferably phenyl or pyridyl optionally substituted with halo, halo alkyl, preferably halo lower alkyl, particularly trifluoromethyl, hydroxy, alkyl, alkyloxy, aminosulfonyl, alkylcarbonyl, nitro, amino, aminocarbonyl, phenylcarbonyl which is optionally substituted with 1 or more, preferably 1 to three, substituents selected from halo, halo lower alkyl and alkyl, or thienyl which is optionally substituted with 1 or more, preferably 1 to 3, substituents selected from halo, haloalkyl or alkyl, in which the alkyl groups are straight or branched chain and preferably are lower alkyl containing from 1–6 carbons, more preferably 1–3 carbons;
- $Ar^4$ is a heteroaryl ring system, preferably a 5- to 10-membered heteroaryl ring system, containing 1 or more, preferably 1 to 3, heteroatoms, such as oxygen, nitrogen and sulfur atoms, preferably thienyl, furanyl, pyridinyl, thiazolyl or imidazolyl, each of which is unsubstituted or substituted with 1 or more, preferably 1 to 3, aryl group substituents, preferably halo or halo lower alkyl, or $Ar^4$ is a radical of formula:

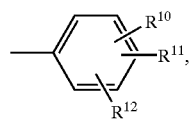

in which $R^{10}$, $R^{11}$ and $R^{12}$ are each independently selected from hydrogen, alkyl, alkyoxy, halide, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, $C_{3-6}$alkynyloxy, arylalkyloxy, aryloxy, alkyl, in which each group is unsubstituted or substituted with up to 4 aryl group subsitutents, preferably halo atoms, and the alkyl groups are straight or branched chains that are preferably lower alkyl ($C_{1-6}$) and more preferably $C_{1-3}$;
- $R^2$ is alkylene, where the alkylene group is a straight or branched chain, preferably is lower alkylene containing from 1 to 6, preferably 1–3 carbons and more preferably is —(CH$_2$)$_2$— or —CH$_2$CH(CH$_3$)—;
- $R^9$ is selected from hydrogen, alkyl, arylalkyl, alkylcarbonyl, aminoalkyl, alkylaminoalkyl, dialkylaminoalkyl, in which the alkyl groups are straight or branched chains and preferably contain 1–6 carbons, more preferably 1–3 carbons in the chain:
- $R^4$ is:

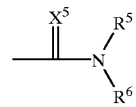

where:
- $X^5$ is as previously defined;
- $R^5$ and $R^6$ are either:
  (i) independently selected from hydrogen, aryl, alkyl that is a straight or branched chain containing preferably 1–6 carbons, more preferably 1–3 carbons, alkenyl that is straight or branched chain, preferably containing 2–6 carbons and 1 double bond, and is more preferably 2-propenyl, aryl, preferably phenyl or arylalkyl, preferably phenylmethyl; or
  (ii) $R^5$ and $R^6$, together with the nitrogen atom to which each is attached, form a 4- to 7-, preferably 5- or 6-, membered heterocyclic ring containing one or two heteroatoms selected from O, S and N, preferably O or N, that is preferably a pyrrolidinyl, piperidinyl, alkylpiperidinyl, morpholinyl, preferably 4-morpholinyl or di($C_1$–$C_6$ alkyl) morpholinyl, more preferably 2,6-di($C_1$–$C_6$ alkyl)-4-morpholinyl, radical;
- $R^8$ is hydrogen or alkyl that is a straight or branched chain, preferably containing from 1 to 6, more preferably 1 to 3, carbons or alkylcarbonyl, preferably lower alkylcarbonyl, such as —C(=O)CH$_2$CH$_3$—.

Preferred among these compounds are those in which the substituents in the 3- and 4-positions on the piperidine ring have the trans configuration. More preferred are those in which $Ar^4$ is phenyl; $R^{10}$ is aryl, loweralkyloxy, $C_{3-6}$alkenyloxy, $C_{3-6}$alkynyloxy, or $C_{1-5}$ alkyl substituted with 1 to 4 halo atoms, and $R^{11}$ and $R^{12}$ are each independently selected from hydrogen, lower alkyl, lower alkyoxy, halo, halo alkyl, hydroxy, cyano, nitro, amino, mono and di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio and mercapto in which each group is unsubstituted or substituted with up to 4 halo atoms, and the alkyl groups are straight or branched chains that are preferably lower alkyl ($C_{1-6}$) and more preferably $C_{1-3}$; $R^5$ and $R^6$ are independently selected from hydrogen, $C_{1-4}$alkyl, phenylmethyl and 2-propenyl.

In more preferred compounds $R^{10}$ is trifluoromethyl substituted on the meta positions, and $R^{11}$ and $R^{12}$ are each independently hydrogen, methyl, methoxy, halo, hydroxy, nitro, amino, trifluoromethyl, phenylmethoxy, phenyloxy, and propenyloxy. Preferred compounds include trans-3-hydroxy-N,N,γ-trimethyl-α,α-diphenyl-4-[[3-(trifluoromethyl)-benzoyl]amino]-1-(piperidinebutanamide.

In other embodiments, the compounds of formula (I) are those having formula (VI) [see, e.g., U.S. Pat. No. 4,194,045] or N-oxides thereof and other pharmaceutically acceptable derivatives:

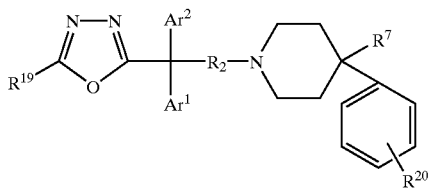

where:
- $Ar^1$ and $Ar^2$ are each independently selected from an aryl ring system, preferably a 6- to 10-membered aryl ring system, and a heteroaryl ring system, preferably a 5- to 10-membered heteroaryl ring system, containing 1 or more, preferably 1 to 3, heteroatoms, such as oxygen, nitrogen and sulfur atoms, where the aryl and heteroaryl ring systems are each optionally substituted with 1 or more, preferably 1 to 3, aryl group substituents, and are preferably phenyl, alkyl substituted phenyl, halo-substituted phenyl, or pyridyl, in which the alkyl groups are straight or branched chains and preferably are lower alkyl containing from 1 to 6 carbons, more preferably 1 to 3 carbons;
- $R^2$ is alkylene, in which the alkylene group is a straight or branched chain, preferably lower alkylene containing from 1 to 6, more preferably 1 to 3 carbons, or is alkenylene containing 2–4 carbons, preferably propenylene or ethenylene, and more preferably —$(CH_2)_2$— or —$CH_2CH(CH_3)$—, and most preferably —$(CH_2)_2$—;
- $R^7$ is —$R^{14}OR^{13}$ in which $R^{13}$ is hydrogen or lower alkyl, preferably containing 1–4 carbons, or is an alkanoyl containing 2 to 5 carbons, preferably 2 or 3, carbon atoms, and $R^{14}$ is lower alkylene or lower alkenyl, preferably methylene or ethylene; and
- $R^{19}$ is hydrogen or lower alkyl, preferably containing 1–4 carbons; and
- $R^{20}$ is hydrogen, halo, haloalkyl, preferably trifluoromethyl, or lower alkyl, preferably containing 1–4 carbons.

Preferred among the compounds of formula (VI) are compounds in which $R^{13}$ is hydrogen or lower alkyl or alkanoyl having 2–5 carbon atoms; $R^{14}$ is methylene or ethylene; $R^{19}$ is hydrogen or methyl; $R^{20}$ is hydrogen, halogen or methyl; $R^2$ is —$(CH_2)_2$—; and $Ar^1$ and $Ar^2$ are phenyl. Such preferred compounds include, for example, 5-[1,1-diphenyl-3-(4-phenyl-4-methanolpiperidino)propyl]-2-methyl-1,3,4-oxadiazole. More preferrred among the compounds of formula VI, are compounds having the formula:

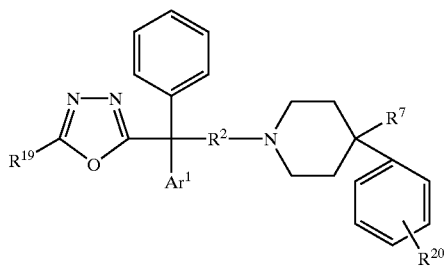

VI

In other embodiments, the compounds of formula (I) are those having formula (VII) [see, e.g., U.S. Pat. No. 3,996, 214] or N-oxides thereof and other pharmaceutically acceptable derivatives:

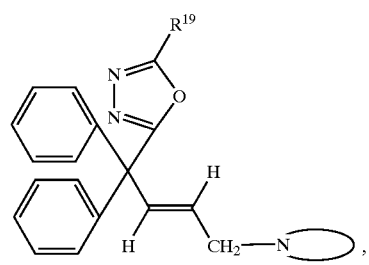

VII where:
- $R^{19}$ is lower alkyl, preferably containing from 1–3 carbon atoms; the configuration of the double bond is trans; and

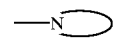

is a tertiary amine selected from azabicycloalkyls containing from 6 to 9 carbon atoms with at least 5 atoms in each ring, where each ring is preferably pyrrolidino, piperidino or hexamethylenimino, and where the tertiary amine is preferably 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6-yl, 3-azabicyclo[3.2.2]non-3-yl, 8-azabicyclo[4.3.0]non-8-yl, 2-azabicyclo[3.2.2]non-2-yl, 2-azabicyclo[3.3.1]non-2-yl, 3-azabicyclo[3.3.1]non-3-yl, 2-azabicyclo[4.3.0]non-2-yl, 7-azabicyclo[4.3.0]non-7-yl, 8-azabicyclo[4.3.1]dec-8-yl, 2-azabicyclo[4.4.0]dec-2-yl, and 7-azabicyclo[4.2.2]dec-7-yl, and is more preferably:

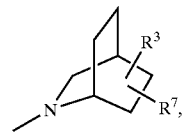

where $R^3$ and $R^7$ are as previously defined.

Preferred compounds include, for example, 5-[1,1-diphenyl-4-(2-azabicyclo[2.2.2]oct-2-yl)but-2-trans-en-1-yl]-2-methyl-1,3,4-oxadiazole.

In other embodiments, the compounds of formula (I) are those having formula (VIII) [see, e.g., U.S. Pat. No. 4,012, 393] or N-oxides thereof and other pharmaceutically acceptable derivatives:

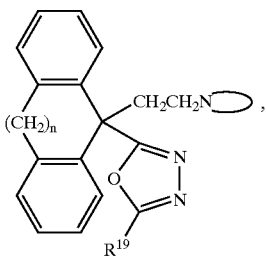

VIII where:

$R^{19}$ is lower alkyl, preferably containing from 1–3 carbon atoms, preferably methyl, n is an integer from 1 to 3, preferably 2 or 3; and

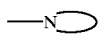

is a tertiary amine selected from azabicycloalkyls containing from 6 to 9 carbon atoms with at least 5 atoms in each ring, where each ring is preferably pyrrolidino, piperidino or hexamethylenimino, and where the tertiary amine is preferably 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6-yl, 3-azabicyclo[3.2.2]non-3-yl, 8-azabicyclo[4.3.0]-non-8-yl, 2-azabicyclo[3.2.2]non-2-yl, 2-azabicyclo[3.3.1]non-2-yl, 3-azabicyclo[3.3.1]non-3-yl, 2-azabicyclo[4.3.0]non-2-yl, 7-azabicyclo[4.3.0]non-7-yl, 8-azabicyclo[4.3.1]dec-8-yl, 2-azabicyclo[4.4.0]-dec -2-yl, and 7-azabicyclo[4.2.2]dec-7-yl, and is more preferably:

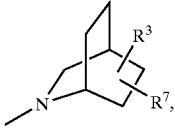

where $R^3$ and $R^7$ are as previously defined.

Preferred compounds include, for example, 2-{5-[2-(2-azabicyclo[2.2.2]oct-2-yl)ethyl]-10.11-dihydro-5H-dibenzo[a,d]cyclohepten -5-yl}-5-methyl-1,3,4-oxadiazole; and 2-{12-[2-(2-azabicyclo[2.2.2]oct-2-yl)ethyl}-5,6,7,12-tetrahydrodibenzo[a,d]cycloocten-12-yl}-5-methyl-1,3,4-oxadiazole.

In other embodiments, the compounds of formula (I) are those having formula (IX) [see, e.g., U.S. Pat. No. 4,013,668] or N-oxides thereof and other pharmaceutically acceptable derivatives:

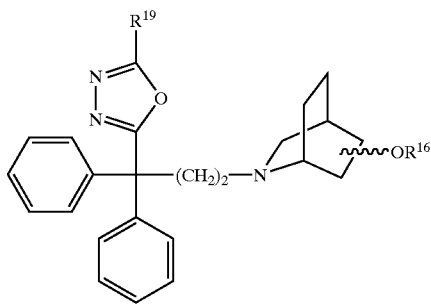

in which $R^{19}$ is lower alkyl; $R^{18}$ is hydrogen or lower alkanoyl containing 2 to 7, preferably 2 or 3, carbon atoms, or preferably $R^{18}$ is hydrogen or acetyl, and is attached at the 5 or 6 position in either the endo or exo configuration.

Preferred among the compounds of formula (IX) are: 5-[1,1-diphenyl-3-(exo-5-hydroxy-2-azabicyclo[2.2.2]oct-2-yl)-propyl]2-methyl-1,3,4-oxadiazole; 5-[1,1-diphenyl-3-(exo-5-acetoxy-2-azabicyclo[2.2.2]oct-2-yl)-propyl]-2-methyl-1,3,4-oxadiazole; 5-[1,1-(diphenyl-3-(endo-5-acetoxy-2-azabicyclo[2.2.2]oct-2-yl)-propyl]-2-methyl-1,3,4-oxadiazole; 5-[1,1-diphenyl-3-(endo-5-hydroxy-2-azabicyclo[2.2.2]oct-2-yl)-propyl]-2-methyl-1,3,4-oxadiazole; 5-[1,1-diphenyl-3-(endo-6-acetoxy-2-azabicyclo[2.2.2]oct-2-yl)-propyl]-2-methyl-1,3,4-oxadiazole; 5-[1,1-diphernyl-3-(endo-6-hydroxy-2-azabicyclo[2.2.2]oct-2-yl)-propyl]-2-methyl-1,3,4-oxadiazole; 5-[1,1-diphenyl-3-(exo-6-acetoxy-2-azabicyclo[2.2.2]oct-2-yl)-propyl]-2-methyl-1,3,4-oxadiazole; and 5-[1,1-diphenyl3-(exo-6-hydroxy-2-azabicyclo[2.2.2]oct-2-yl)-propyl]-2-methyl-1,3,4-oxadiazole.

In other embodiments, the compounds of formula (I) are those having formula (X) [see, e.g., U.S. Pat. No. 4,069,223] or N-oxides thereof and other pharmaceutically acceptable derivatives:

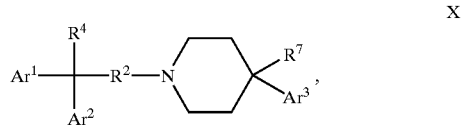

X in which:

$Ar^1$, $Ar^2$, and $Ar^3$ are each independently selected from an aryl ring system, preferably a 6 to 10-membered aryl ring system, more preferably phenyl, optionally substituted with 1 or more, preferably 1 to 3, more preferably 1 or 2, aryl group substituents, preferably halo, lower alkyl or halo lower alkyl;

$R^2$ is alkylene, in which the alkylene group is a straight or branched chain, preferably is lower alkylene containing from 1 to 6, preferably 1–3 carbons, or is alkenylene containing 2–4 carbons, preferably 2 or 3 carbons, and is more preferably is —$(CH_2)_2$— or —$CH_2CH(CH_3)$—, and most preferably —$(CH_2)_2$—;

$R^4$ is an aryl ring system, preferably a 6 to 10-membered aryl ring system, or a heteroaryl ring system, preferably a 5 to 10-membered heteroaryl ring system, containing 1 or more, preferably 1 to 3, heteroatoms, such as oxygen, nitrogen and sulfur atoms, preferably phenyl or pyridyl, optionally substituted with 1 or more, preferably 1 to 3, aryl group substituents, preferably halo, halo lower alkyl or lower alkyl; and $R^7$ is $C(O)OR^{17}$ in which $R^{17}$ is hydrogen or lower alkyl, —$R^{14}OR^{13}$ or $CH_2NR^{15}R^{16}$ in which $R^{15}$ is hydrogen, lower alkyl or lower alkanoyl and $R^{16}$ is hydrogen or lower alkyl. In more preferred embodiments of the compounds of formula (X), $Ar^1$, $Ar^2$ and $Ar^3$ are each phenyl and $R^4$ is phenyl or pyridyl.

Included among the preferred compounds of these compounds of formula (X) are, for example, 4-amino-methyl-4-phenyl-1-(3,3,3-triphenylpropyl)piperidine and N-{[4-phenyl-1-(3,3,3-triphenylpropyl)piperidine-4-yl[methyl] acetamide.

In other embodiments, the compounds are those of formula (X) [see, e.g., U.S. Pat. No. 4,066,654] in which $Ar^1$, $Ar^2$ and $Ar^3$ are each independently selected from among phenyl that is unsubstituted or substituted with up to three aryl group substituents, preferably at one or two positions with halo, lower alkyl or halo lower alkyl, preferably containing 1 to 4 carbons; $R^2$ is alkyl, where the alkylene group is a straight or branched chain, preferably is lower alkylene containing from 1 to 6, preferably 1–3 carbons, or is alkenylene, preferably a branched chain, containing 2–4 carbons, preferably alkenylene containing 3 or 4 carbons, and more preferably is —$(CH_2)_2$— or —$CH_2CH(CH_3)$—, and most preferably —$(CH_2)_2$—; $R^4$ is phenyl or pyridyl, each of which is unsubstituted or is substituted with 1 or more, preferably 1 to 3, aryl group substituents, such as halo or lower alkyl, preferably containing 1 to 4 carbons; $R^7$ is $C(O)OR^{17}$ in which $R^{17}$ is hydrogen, alkyl containing from 1 to 7 carbons or alkenyl having 3 to 7 carbon atoms, aryl or heteroaryl, particularly pyridyl, phenyl, tolyl, ethylphenyl, butylphenyl, halophenyl, alkenyl containing 3 to 7 carbons and having formula —$C_nH_{(2n-1)}$, where n is an integer from 3 to 7, or is an alkali metal or alkaline earth metal salt, such as sodium, potassium, calcium, and ammonium. In preferred embodiments, $Ar^1$ and $Ar^2$ are phenyl and $R^4$ is phenyl or 2-, 3- or 4-pyridyl.

Among the preferred of these compounds of formula (X) are, for example, 1-(3,3,3-triphenylpropyl)-4-phenyl-4-piperidinecarboxylic acid and the hydrochloride salt thereof; ethyl 1-(3,3,3-triphenylpropyl)-4-phenyl-4-piperidinecarboxylate; potassium 1-(3,3,3-triphenylpropyl)-4-phenyl-4-piperidinecarboxylate; sodium 1-(3,3,3-triphenylpropyl)-4-phenyl-4-piperidinecarboxylate; 1-[3,3-diphenyl-3-(2-pyridyl)propyl]4-phenyl-4-piperidine carboxylic acid hydrochloride; sodium 1-[3,3-diphenyl-3-(2-pyridyl)propyl]-4-phenyl-4-piperidinecarboxylate; ethyl 1-[3,3-diphenyl-3-(2-pyridyl)propyl]-4-phenyl-4-piperidinecarboxylate; potassium 1-[3,3-diphenyl-3-(2-pyridyl)propyl]-4-phenyl-4-piperidinecarboxylate.

In other embodiments, the compounds are those of formula (X) [see, e.g., U.S. Pat. No. 4,072,686] in which $Ar^1$, $Ar^2$ and $Ar^3$ are each independently selected from among phenyl that is unsubstituted or substituted with up to three aryl group substituents, which are preferably halo, lower alkyl or halo lower alkyl, preferably containing 1 to 4 carbons; $R^2$ is alkylene, where the alkylene group is a straight or branched chain, preferably is lower alkylene containing from 1 to 6, preferably 1–3 carbons, or is alkenylene containing 2–4 carbons, preferably alkenylene containing 3 or 4 carbons, and is more preferably —$(CH_2)_2$— or —$CH_2CH(CH_3)$—, and most preferably —$(CH_2)_2$—; $R^4$ is phenyl or pyridyl, each of which is unsubstituted or is substituted with up to three aryl group substituents, preferably halo or lower alkyl, where the alkyl preferably contains 1 to 4 carbons; $R^7$ is —$R^{14}OR^{13}$ in which $R^{13}$ is hydrogen or lower alkyl, preferably containing 1–4 carbons, or is an alkanoyl containing 2 to 5, preferably 2 or 3, carbon atoms, and $R^{14}$ is lower alkylene containing 1 to 4 carbons, and is preferably methylene or ethylene, or is lower alkenylene containing 2 to 4 carbons, having formula —$C_nH_{2n-1}$— where n is an integer from 1 to 4, containing preferably 3 or 4 carbons. In preferred embodiments, $Ar^1$ and $Ar^2$ are phenyl and $R^4$ is phenyl or 2-, 3- or 4-pyridyl.

Among the preferred of these compounds of formula (X) are, for example, 1-(3,3,3-triphenylpropyl)-4-phenyl-4-piperidinemethanol; 1-[3,3-diphenyl-3-(2-pyridyl)propyl]-4-phenyl-4-piperidinemethanol; 1-(3,3,3-triphenylpropyl)-4-phenyl-4-acetoxymethyl-piperidine; 1-(3,3,3-triphenylpropyl)-4-phenyl-4-methoxymethyl-piperidine; 1-(3,3,3-triphenylpropyl)-4-(4-chlorophenyl)-4-piperidinemethanol; 1-[3-p-chlorophenyl-3,3-diphenylpropyl]-4-(phenyl)-4-piperidinemethanol; 1-[3-(p-tolyl)-3,3-diphenylpropyl]-4-(phenyl)-4-piperidinemethanol; 1-[3-(p-bromophenyl)-3,3-diphenylpropyl]-4-(phenyl)-4-piperidinemethanol; 1-[3,3-diphenyl-3-(4-pyridyl)-propyl]-4-phenyl-4-piperidinemethanol; 1-[3,3-diphenyl-3-(3-pyridyl)propyl]-4-phenyl-4-piperidinemethanol; 1-(3,3,3-triphenylpropyl)-4-phenyl-4-hexoxymethyl-piperidine; 1-(3,3,3-triphenylpropyl)-4-(p-tolyl)-4-piperidinemethanol; 1-(3,3,3-triphenylpropyl)-4-(p-trifluoromethylphenyl)-4-piperidinemethanol; 1-(4,4,4-triphenylbutyl)-4-(phenyl)-4-piperidinemethanol; 1-(3,3,3-triphenylpropyl)-4-phenyl-4-methoxyethylpiperidine; 1-[3,3-diphenyl-3-(2-pyridyl)propyl]-4-phenyl-4-methoxyethylpiperidine; 1-(3,3,3-triphenylpropyl)-4-phenyl-4-piperidinemethanol; 1-[3,3-diphenyl-3-(2-pyridyl)propyl]-4-phenyl-4-piperidinemethanol; and acid salts thereof.

In other embodiments, the compounds of formula (I) are those having formula (XI) [see, e.g., U.S. Pat. No. 4,116,963] or N-oxides thereof and other pharmaceutically acceptable derivatives thereof:

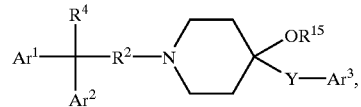

XI where:

$Ar^1$, $Ar^2$ and $Ar^3$ are each independently selected from an aryl ring system, preferably a 6- to 10-membered aryl ring system, most preferably phenyl that is unsubstituted or substituted with 1 or more, preferably 1 to 3, aryl group substituents, preferably selected from halo, halo lower alkyl or lower alkyl, preferably containing 1 to 4 carbons; $R^2$ is alkylene, where the alkylene group is a straight or branched chain, preferably is lower alkylene containing from 1 to 6, preferably 1–3 carbons, or is alkenylene containing 2–4 carbons, preferably alkenylene containing 2 to 4, preferably 3 or 4 carbons, and more preferably is —$(CH_2)_2$— or —$CH_2CH(CH_3)$—, and most preferably is —$(CH_2)_2$—; $R^4$ is an aryl ring system, preferably a 6- to 10-membered aryl ring system, most preferably phenyl, or a heteroaryl ring system, preferably a 5- to 10-membered heteroaryl ring system, containing 1 or more, preferably 1 to 3, heteroatoms, such as oxygen, nitrogen and sulfur atoms, most preferably pyridylphenyl that is unsubstituted or is substituted with 1 or more, preferably 1 to 3, aryl group group substituents, preferably selected from halo, halo lower alkyl or lower alkyl, preferably containing 1 to 4 carbons; $R^{15}$ is hydrogen, alkyl, containing 1 to 12 carbons, preferably lower alkyl, or alkanoyl containing 2 to 12 carbons, preferably lower alkanoyl; and Y is alkylene having 1 to 3 carbons, and is preferably —$CH_2$—.

Among the preferred compounds of formula (XI) are, for example, 1-(3,3,3-triphenylpropyl)4-hydroxy-4-benzylpiperidine and 1-(3,3,3-triphenylpropyl)-4-hydroxy-4-benzylpiperidine; hydrochloride; 1-(3,3,3-triphenylpropyl)-4-hydroxy-4-p-chlorobenzylpiperidine; 1-(3,3,3-triphenylpropyl)-4-hydroxy-4-p-methylbenzylpiperidine; and 1-[3,3-diphenyl-3-(2-pyridyl)propyl]-4-benzyl-4-hydroxypiperidine.

In other embodiments, the compounds are amidinoureas [see, U.S. Pat. Nos. 4,326,075, 4,203,920, 4,115,564, 4,060, 635 and 4,025,652] or are 2-[(aminophenyl and amidophenyl)amino]-1-azacycloalkanes [see, U.S. Pat. No. 4,533,739] that have formula XII or pharmaceutically acceptable derivatives, including the non-toxic acid addition salts thereof:

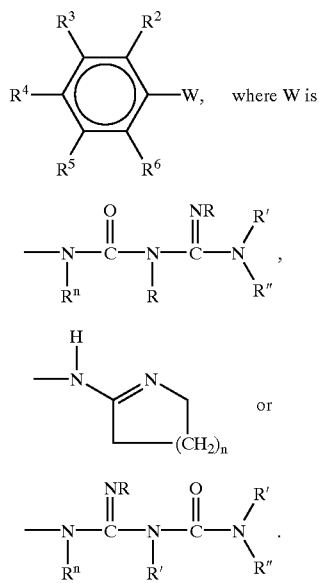

In the compounds of formula (XII), W is XII(a), XII(b) or XII(c).

(i) When, W is XII(a) or XII(c), then $R^2$, $R^3$, $R^4$, $R^5$ and $R^6$, which are the same or different, are each independently selected from: hydrogen, halo, lower alkyl, halo lower alkyl, nitro, lower alkoxy, hydroxy, aryl lower alkoxy, acyloxy, cyano, halo lower alkoxy or lower alkyl sulfonyl; R is hydrogen or lower alkyl; R' and R" are hydrogen, alkyl, cycloalkyl or aralkyl, or R' and R" together form a 5–7 atom ring that includes 0 to 2 hetero atoms selected from N, O or S; and $R^n$ is hydrogen or lower alkyl, provided that at least one of R, R' and R" is other than hydrogen, and the non-toxic acid addition salts thereof.

When W is XII(a) or XII(c) preferred compounds are those in which: $R^2$, $R^3$, $R^4$, $R^5$ and $R^6$ are hydrogen, halo, lower alkyl, halo lower alkyl, nitro, hydroxy or lower alkoxy; and R and $R^n$ are hydrogen or lower alkyl and R' and R" are hydrogen or alkyl; provided R, R' and R" are not all hydrogen at the same time.

More preferred compounds, when W is XII(a) include those where: $R^2$ is hydrogen or lower alkyl; $R^3$ and $R^5$ are hydrogen, hydroxy or lower alkoxy; $R^4$ is hydrogen, lower alkyl, hydroxy, lower alkoxy or halo, $R^6$ is hydrogen, lower alkyl, nitro, alkoxy or halo; R and $R^n$ are hydrogen or lower alkyl; and R' and R" are hydrogen or alkyl; provided R, R' and R" are not all hydrogen at the same time.

More preferred compounds, when W is XII(c), include those where: $R^2$, $R^3$, $R^4$, $R^5$ and $R^6$ are hydrogen, chloro, bromo, fluoro, methyl, ethyl, trifluoromethyl, nitro, methoxy or hydroxy; R and $R^n$ are hydrogen or lower alkyl; and R' and R" are hydrogen or alkyl; provided R, R' and R" are not all hydrogen at the same time.

The most preferred compounds, when W is XII(a), are those where: $R^2$ is hydrogen, methyl or ethyl; $R^3$ is hydrogen, hydroxy or methoxy; $R^4$ is hydrogen, methyl, ethyl, hydroxy, methoxy, chloro or bromo; $R^5$ is hydrogen, hydroxy or methoxy; $R^6$ is hydrogen, methyl, ethyl, nitro, methoxy, ethoxy, chloro, bromo or fluoro; R and $R^n$ are hydrogen, methyl or ethyl; and R' and R" are hydrogen, methyl, ethyl, propyl, i-propyl, butyl, i-butyl, sec-butyl, t-butyl, pentyl, hexyl or heptyl; provided R, R' and R" are not all hydrogen at the same time. The most preferred compounds, when W is XII(c), include those where: $R^2$ and $R^6$ are lower alkyl or lower alkoxy; and $R^3$, $R^4$ and $R^5$ are halo, halo lower alkyl, lower alkoxy or hydroxy.

Other preferred compounds, when W is XII(a) include those in which the compounds have a $R^2$, $R^6$-di-lower alkyl substitution; $R^2$-lower alkyl substitution; $R^2$, $R^6$-lower alkyl, alkoxy substitution; $R^2$, $R^6$-lower alkyl, halo substitution; $R^2$, $R^6$-alkyl, nitro substitution; $R^2$, $R^4$, $R^6$-tri-lower alkyl substitution, or $R^2$, $R^4$, $R^6$-lower alkyl, di-halo substitution. Other preferred compounds have an $R^3$, $R^4$-hydroxy or alkoxy substitution; a $R^3$, $R^4$, $R^5$-hydroxy or alkoxy substitution; $R^2$, $R^5$-di-halo substitution or $R^2$, $R^6$-di-halo substitution.

Other preferred compounds, when W is XII(a) include those that in which R, R' and R" are hydrogen or lower alkyl substitution, provided that all are not hydrogen at the same time; or R and R' are hydrogen or lower alkyl and R" is an alkyl group from 3 to 7 carbon atoms.

Other preferred compounds, when W is XII(c), include those in which the compounds have $R^3$, $R^4$-dihalo substitution; $R^3$, $R^4$ and/or $R^3$, $R^4$ and $R^5$ alkoxy or hydroxy substitution; $R^2$, $R^6$-dilower alkyl substitution; or $R^2$, $R^6$-lower alkyl, alkoxy substitution. Other preferred compounds have an R, R' and R" hydrogen or lower alkyl substitution, provided all are not hydrogen at the same time; or R and R' are hydrogen or lower alkyl and R" is alkyl containing from 3 to 7 carbon atoms.

When W is XII(a), preferred compounds include, but are not limited to: 1-amidino-3-(2-methyl-6-chlorophenyl)urea; 1-amidino-3-(2-chloro-4-methylphenyl)urea; 1-amidino-3-(2-methyl-6-bromophenyl)urea; 1-amidino-3-(2-chloro-5-bromophenyl)urea; 1-amidino-3-(2,5-dichlorophenyl)-urea; 1-amidino-3-(2-methyl-6-ethylphenyl)urea; 1-amidino-3-(2-ethyl-6-trifluoromethylphenyl)urea; 1-amidino-3-(3,4-dimethoxyphenyl)urea; 1-amidino-3-(3,4,5-trimethoxyphenyl)urea; 1-amidino-3-(3,4,5-tribenzyloxyphenyl)urea; 1-amidino-3-(2,4-dimethyl-6-nitrophenyl)urea; 1-amidino-3-(2-ethylphenyl)urea; 1-amidino-3-(2,4-dimethyl-6-methoxyphenyl)urea; and 1-amidino-3-(2-methyl-4-methoxy-6-chlorophenyl)urea.

When W is XII(c), preferred compounds include, but are not limited to: m-chlorophenylamidinourea; p-chlorophenylamidinourea; 3,4-dichlorophenylamidinourea; m-bromophenylamidinourea; p-bromophenylamidinourea; 3,4-dibromophenylamidinourea; 3-chloro-4-bromophenylamidinourea; 3-bromo-4-chlorophenylamidinourea; 3-chloro-4-fluorophenylamidinourea; 3-bromo-4-fluorophenylamidinourea; 3-fluoro-4-chlorophenylamidinourea; 2,6-dimethylphenylamidinourea; 2,6-diethylphenylamidinourea; 2-methyl-6-ethylphenylamidinourea; 2-methyl-6-methoxyphenylamidinourea; 2-methyl-6-ethoxyphenylamidinourea; 2-ethyl-6-methoxyphenylamidinourea; 2-ethyl-6-ethoxyphenylamidinourea; 3,4-dimethoxyphenylamidinourea; 3,4-dihydroxyphenylamidinourea; 3,4,5-trimethoxyphenylamidinourea; and 3,4,5-trihydroxyphenylamidinourea.

(ii) In the compounds of formula (XII) or the pharmacologically acceptable salts thereof, when W is XII(b), when n is 1 to 3, preferably 1;

$R^2$, $R^6$ and $R^3$, which are independently selected and are the same or different, are selected from among: (a) hydrogen; (b) alkyl or 1 to 6 carbon atoms, inclusive; or (c) halogen; with the proviso that $R^2$ and $R^6$ are not hydrogen at the same time; and one of R⁴ and R⁵ is hydrogen, alkyl of 1 to 6 carbon atoms, inclusive, or halogen and the other is of the formula: —NR⁸R⁷ in which R⁸ and R⁷, which are the same or different, are selected from among: (a) hydrogen; (b) alkyl of 1 to 6 carbon atoms, inclusive; (c) alkoxycarbonyl of 2 to 7 carbon atoms, inclusive; (d) aryloxycarbonyl of 6 to 12 carbon atoms inclusive; (e) alkylcarbonyl of 2 to 7 carbon atoms inclusive; (f) arylcarbonyl of 6 to 12 carbon atoms, inclusive; (g) hydroxyalkoxycarbonyl of 3 to 7 carbon atoms, inclusive; (h) R⁸ and R⁷ are taken together to form (1) —(CH₂)ₚ—; where p is 4 or 5; (2) —(CH₂)ₘCO—, where m is 3 or 4; (i) haloalkylcarbonyl of 2 to 7 carbon atoms, inclusive; where n is an integer of from 1 to 3, inclusive.

Preferred among the compounds of formula (XII) in which W is XII(b) are: 2-[(2-methyl-3-aminophenyl)amino]-1-pyrroline, dihydrochloride; 2-[(2-methyl-3-acetamidophenyl)amino]-1-(pyrroline, hydrochloride; and 2-[(2-methyl-3-(ethoxycarbonylamino)phenyl-)amino]-1-pyrroline, hydrochloride.

Also among the compounds of formula (I) of interest herein are the 2-substituted-1-azabicyclo[2,2,2]octanes [see, U.S. Pat. No. 4,125,531] of formula XIII:

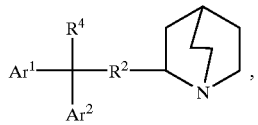

where:

R² is lower alkylene, preferably containing 1 to 3 carbons;

Ar¹ and Ar² are each independently selected from an aryl ring system, preferably a 6- to 10-membered aryl ring system, and a heteroaryl ring system, preferably a 5- to 10-membered heteroaryl ring system, containing 1 or more, preferably 1 to 3, heteroatoms, such as oxygen, sulfur or nitrogen atoms, where the aryl and heteroaryl ring systems are each optionally substituted with 1 or more, preferably 1 to 3 aryl group substituents, and each is preferably phenyl or pyridyl optionally substituted with halo, halo alkyl, preferably halo lower alkyl, particularly trifluoromethyl, hydroxy, alkyl, alkyloxy, aminosulfonyl, alkylcarbonyl, nitro, amino, aminocarbonyl, phenylcarbonyl that is optionally substituted with 1 or more, preferably 1 to 3, substituents selected from halo, halo lower alkyl and alkyl, or thienyl that is optionally substituted with 1 or more, preferably 1 to 3, substituents selected from halo, haloalkyl and alkyl, in which the alkyl groups are straight or branched chains and preferably are lower alkyl containing from 1–6 carbons, more preferably 1–3; and R⁴ is selected from alkyl containing from 1 to 8 carbons, preferably 1 to 6, more preferably 1 to 3 carbons, or is alkenyl containing 3 to 6 carbon atoms, or is cycloalkyl containing from 3 to 6 carbons, or is cycloalkyl alkyl in which the cycloalkyl contains 3 to 6 carbons and the alkyl contains 1 to 3 carbons, or is a cycloalkenyl containing 4 to 7 carbons. Preferred among compounds of formula XIII are 2-(2,2-diphenylpentyl)-1-azabicylo[2.2.2]octane, 2-(2,2-diphenylhexyl)-1-(azabicylo[2.2.2]octane, 2-(2,2-diphenylpropyl)-1-azabicylo[2.2.2]octane, 2-(2,2-diphenyloctyl)-1-(azabicylo[2.2.2]octane and 2-(2,2-diphenylheptyl)-1-azabicylo[2.2.2]octane.

Other compounds of interest for use in the methods of preventing or treating hyperalgesia provided herein include certain phenylacetamide derivatives [see, U.S. Pat. No. 5,242,944], including, but not limited to N-{(3,4-dimethylphenyl)propyl}-4-(2-aminoethoxy)-3-methoxyphenylacetamide, N-{(3,4-dimethylphenyl)propyl}-4-(2-aminoethoxy)-3-hydroxy-phenylacetamide, N-{(3,4-dimethylphenyl)propyl}-4-(2-aminoethoxy)-3-aminophenylacetamide, N-{(3-methylphenyl)propyl}-4-(2-aminoethoxy)-3-methoxy-phenylacetamide, N-{(3-methylphenyl)propyl}-4-(2-aminoethoxy)-3-hydroxyphenylacetamide and N-{(3-dimethylphenyl)propyl}-4-(2-aminoethoxy)-3-aminophenylacetamide and other such compounds.

Also of interest are 3-hydroxy-7-oxomorphinans and 3-hydroxy-7-oxoisomorphinans [see, U.S. Pat. No. 4,277,605] including, but not limited to: 3-hydroxy-7-oxomorphinan and 3-hydroxy-7-oxoisomorphinans including d,l-3-hydroxy-7-oxo-N-methylmorphinan, l-3-hydroxy-7-oxo-N-methylmorphinan, d,l-3-hydroxy-7-oxomorphinan, l-3-hydroxy-7-oxomorphinan, d,l-3-hydroxy-7-oxo-N-methylisomorphinan, l-3-hydroxy-7-oxo-N-methylisomorphinan, d,l-3-hydroxy-7-oxoisomorphinan l-3-hydroxy-7-oxoisomorphinan and quaternary ammonium salts thereof, and other such compounds.

Among other opioid compounds for use herein are enkephalin analogs, such as metkephamid H-L-Tyr-D-Ala-Gly-L-Phe-N(Me)Met-NH₂; see, e.g., U.S. Pat. No. 4,430,327; Burkhart et al. (1982) *Peptides* 3:869–871; Frederickson et al. (1991) *Science* 211:603–605], [D-Thr²,Δ³-Pro⁵]-enkephalinamide, and other such analogs that have been designed not to pass through the blood-brain barrier or to exhibit minimal CNS effects relative to anti-diarrheal activity, such as synthetic opioid peptides, including H-Tyr-D-Nva-Phe-Orn-NH₂, H-Tyr-D-Nle-Phe-Orn-NH₂, H-Tyr-D-Arg-Phe-A₂bu-NH₂, H-Tyr-D-Arg-Phe-Lys-NH₂, and H-Lys-Tyr-D-Arg-Phe-Lys-NH₂[ see, U.S. Pat. No. 5,312,899; see, also Gesellchen et al. (1981) *Pept.: Synth., Struct., Funct., Proc. Am. Pept. Symp.*, 7th,; Rich et al. (Eds), Pierce Chem. Co., Rockford, Ill., pp. 621–62] that do not cross the blood brain barrier.

Of all of the above compounds, those of formulae (I) are presently preferred. Those of formulae (II)–(IV) are more preferred and of those the following compounds or N-oxides or pharmaceutically active acid addition salts thereof are particularly preferred: 1-[4-(4-hydroxy-4-phenyl-1-piperidino)-2,2-diphenylbutyryl]piperidine; 4-{4-[4-hydroxy-4-(3-trifluoromethylphenyl)-1-piperidino]-2,2-diphenylbutyryl}morpholine; 1-{4-[4-hydroxy-4-(3-trifluoromethylphenyl)-1-piperidino]-2,2-diphenylbutyl}piperidine; 4-(p-chlorophenyl)-4-hydroxy-N-N-,γ-trimethyl-α,α-diphenyl-1-(piperidine-1-butyramide; 4-(p-chlorophenyl)-4-hydroxy-N-N-dimethyl-α,α-diphenyl-1-(piperidine-1-(butyramide(loperamide); 4-(3,4-dichlorophenyl)-N,N-diethyl-4-hydroxy-α,α-diphenyl-1-piperidine-1-butyramide; 4-(3,4-dichlorophenyl)-4-hydroxy-N,N-dimethyl-α,α-diphenyl-1-(piperidine-1-(butyramide; 4-(4-chloro-3-trifluoromethylphenyl)-4-hydroxy-N,N-dimethyl-α,α-diphenyl-1-piperidine-1-butyramide; 4-(p-fluorophenyl)-4-hydroxy-N-N,γ-trimethyl-α,α-diphenyl-1-(piperidine-1-(butyramide; 4-(p-bromophenyl)-4-hydroxy-N-N-dimethyl-α,α-diphenyl-1-(piperidine-1-(butyramide; 1-{4-[4-(3,4-dichlorophenyl)-4-hydroxypiperidino]-2,2-diphenylbutyryl}pyrrolidine; and 4-(p-chlorophenyl)-N-ethyl-4-hydroxy-N-methyl-α,α-diphenyl-1-piperidine-1-(butyramide.

Diphenoxylate may be used in the methods and compositions herein. More preferably, difenoxin [1-(3-cyano-3,3-diphenylpropyl)-4-phenyl-4-piperidinecarboxylic acid] is used.

Of the compounds provided herein, loperamide, [4-(p-chlorophenyl) -4-hydroxy-N-N-dimethyl-α,α-diphenyl-1-piperidinebutyramide] and the salts, hydrates, N-oxides, and metabolites (preferably glucuronides) thereof, particularly the hydrochloride salts, are presently most preferred. The structure of loperamide is as follows:

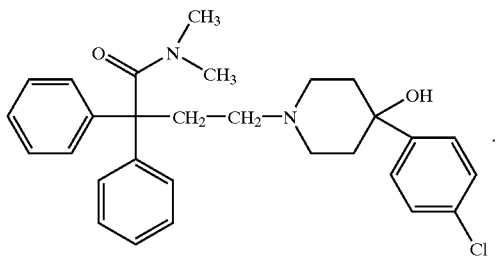

Also preferred are the N-oxides of loperamide (see, e.g., U.S. Pat. No. 4,824,853) having the formula:

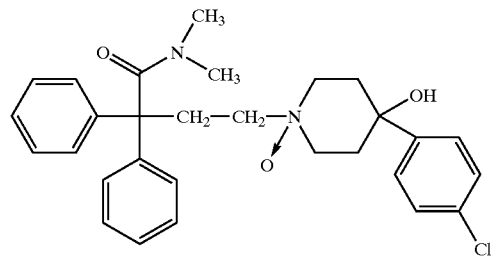

or other derivatives thereof.

Loperamide and its derivatives and analogs and the compounds described above [including those of formulae I–XIII, the other disclosed compounds and any compound that has the requisite hyperalgesic activity and lack of CNS activity as defined herein] will serve as topical or local peripheral anti-hyperalgesics that, by virtue of their inability or substantial inability to cross the blood-brain barrier, are safe and without abuse potential. This finding with respect to loperamide [see, e.g., Jaffe et al. (1980) Clin. Pharmacol. Ther. 80:812–819] has been verified by its use over-the-counter for over 10 years as an anti-diarrheal medication.

Other particularly preferred compounds include loperamide analogs, particularly compounds of formula (II) above, that have similar activity to loperamide [see, e.g., U.S. Pat. Nos. 3,714,159 and 3,884,916, which set forth data regarding CNS activity (as measured in the tail withdrawal assay) and B/A ratios for the compounds] or better activity [higher B/A ratio than loperamide].

B. Identification of Compounds for Use as Peripheral Anti-hyperalgesics

In general the Randall-Selitto methods, described below, and the Exemplified methods are preferred for assessing peripheral anti-hyperalgesic activities of tested compounds. Most preferred among the methods for assessing anti-hyperalgesic activity are those described in Niemegeers et al. (1974) Drug Res. 24:1633–1636.

1. Assessment of Ratio [C] of the $ED_{50}$ Value [A] in a Test for Anti-diarrheal Activity, Such as the Castor Oil Test, to the $ED_{50}$ Value [B] in a Test of CNS Effects, Such as the Tail Withdrawal Test The agents intended for use in the methods and compositions can be identified by their activity as anti-diarrheals, and their lack of CNS effects. In particular, the selected compound exhibits anti-hyperalgesic activity in any of the standard models, discussed or exemplified below, and, preferably, either (a) the ratio of these activities [B/A], as measured in standard assays, is substantially greater or equal to [at least equal to, more preferably at least about 2-fold greater] than the ratio of such activities for diphenoxylate; or (b) the activity of the compound in an assay that measures CNS activity is substantially less [at least two-fold, preferably 3-fold or more] than diphenoxylate.

2. Assessment of Anti-hyperalgesic Activity

The agents for use herein may be identified using standard assays that assess the anti-hyperalgesic properties. The anti-hyperalgesic properties of a particular agent may be evaluated using the clinically relevant models of hyperalgesia, particularly animal models of tissue inflammation [see, e.g., Ferreira et al. (1979) Prostaglandins 73:191–200; Abbott et al. (1988) Eur. J. Pharmacol. 152:92–100; Levine et al. (1989) Neuroscience 32:571–575; Stein et al. (1989) J. Pharmacol. Exp. Ther. 248:1269–1275; Porreca et al. (1984) J. Pharmacol. Exp. Ther. 230:341–348; Stein et al. (1993) Anesth. Analg. 76:182–191]. For example, the intraplantar injection of agents, such as prostaglandins into hindpaws of rats produces a localized inflammatory response which exhibits symptoms of hyperalgesia. In this model the latency of response by the animal to superimposed stimuli, such as pressure exerted on inflamed tissue is measured. Alternatively, the amount of pressure required to evoke a behavior response is measured.

In other models, the intraperitoneal administration of irritants, such as acetic acid, prostaglandins, carrageenan, killed mycobacteria, formalin or bradykinin, produces an inflammatory reaction in which hyperalgesia is evidenced by writhing; behavioral alterations, such as the number of abdominal constrictions [writhing], following application of the irritant are measured.

Any suitable in vitro or in vivo test (for purposes herein in vivo tests are preferred) known to those of skill in this art may be used to assess systemic opioid activity. The rat hot plate assay and the rat tail withdrawal assay are typical of such assays.

(a) Inflamed Knee Joint Hyperalgesia Model and Blood Pressure Response to Compression of the Inflamed Knee Joint Inflammation in a joint is often associated with hyperalgesia [pain during normal flexion and extension and during the application of gentle innocuous pressure] and/or persistent pain [resting pain; Schaible et al. (1993) Pain 55:5–54]. During the course of knee-joint inflammation, a cascade of events has been shown to occur, which includes: (i) synthesis and release of inflammatory mediators in the joint, (ii) release of neuropeptides from afferent fibers in the joint cavity, and (iii) increased primary afferent outflow from group II, III, IV sensory fibers [Schaible et al. (1993) Pain 55:5–54. An important result of this cascade is that there is an augmentation in the response of small, lightly myelinated and unmyelinated afferent to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension [Schaible et al. (1985) J. Neurophysiol. 54:1109–1122] and signs of a pain-associated autonomic reaction [Sata et al. (1984) Neurosci. Lett. 52:55–60].

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, indicating the presence of hyperalgesia. According to electrophysiological studies, in the course of the development of this acute arthritis, C and Aδ units normally responding only to extreme joint distortion become activated by slight movement [Schaible et al. (1985) *J. Neurophysiol.* 54:1109–1122]. Spinal neurons with knee joint receptive fields in the deep dorsal horn of the spinal cord show clear development of hyperexcitability with the acute inflammation in the joint [Neugebauer et al. (1993) *J. Neurosci.* 70:1365–1377]. This sensitization of group IIII and IV fibers was observed within 2–3 hours after injection of kaolin and carrageenan into the knee joint, a time course that closely matches the time course of the development of hyperalgesia in the rat knee joint compression model.

These observations indicate that spinal cord neurons and joint primary afferent fibers became sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure [BP] changes might also be evoked reflexively by afferent neural activity from receptors located in the skeletal muscle [Williamson et al. (1994) *J. Physiol.* 475:351–357]. This response is dependent on the changes in intramuscular pressure and the quantity of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and Aδ units was observed in the rat gastrocnemius muscle by infiltration with carrageenan [Handwerker et al (1991) *Pain and inflammation, Proceeding of the VIth World Congress on Pain*, Bond et al. eds, Elsevier Science Publishers BV, pp. 59–70]. Based on these considerations, it appears that compression of the inflamed knee joint yields a noxious stimulus and this in turn activates a sympathetic response resulting in an increase in BP.

As described in the Examples below, local inflammation of the knee results in a state where otherwise innocuous stimuli results in a prominent autonomic response, including increased blood pressure [BP] and heart rate [see, e.g., Sata et al.(1984) *Neurosci. Lett.* 52:55–60]. Alternatively, neural outflow from the inflamed knee is recorded [see, e.g., Neugebauer et al. (1993) *J. Neurosci.* 70:1365–1377].

An in vitro test that measures spontaneous discharge in injured skin by topical application may also be used. [see, e.g., Andreev et al. (1994) *Neurosci.* 58:793–798].

(b) Guinea Pig Ileum Assay (in vitro)

Compounds are tested for opioid activity in the isolated guinea pig ileum [see, e.g, Kosterlitz et al. (1968) *Br. J. Pharmacol.* 33:266–276 with modifications set forth in James et al. (1987) *PharmacolExp. Ther.* 240:138–144; see, e.g., U.S. Pat. No. 5,387,688]. The terminal ileum is removed from male Hartley guinea pigs after sacrifice by cervical dislocation. The isolated ileum is washed and placed in Krebs-Henseleit buffer [(millimolar): NaCl, 118.1; KCl, 4.15; $CaCl_2$, 2.5; $MgSO_4$ 1.2; $KH_2PO_4$, 1.23; $NAHCO_3$, 25.5 and glucose, 11.1] oxygenated with a 95% oxygen and 5% carbon dioxide mixture and maintained at 37° C. The washed ileum is cut into segments (about 2.0–2.5 cm) and mounted on platinum ring electrodes. The ileal segments are then placed in 10 ml temperature-controlled tissue baths containing oxygenated Krebs-Henseleit buffer.

The ileal segments are stimulated at 0.1 Hertz, 0.5 milliseconds duration at a supramaximal voltage to induce contractions. Opioid activity in the test compounds is manifested as inhibition of electrically evoked contractions. A non-cumulative concentration-effect curve for each test compound is performed to assess the ability of the compound to inhibit contraction in the guinea pig ileum.

After the concentration-effect curve is completed, naloxone is added to the tissue baths to determine if the compound-induced inhibition of contraction is reversed. Antagonism of the inhibition by naloxone confirms that the inhibitory effects of the compounds are mediated through opioid receptors. Assay results are expressed as $IC_{50}$ values [the concentration producing fifty percent of the maximal response].

(c) Randall-Selitto Test

Numerous variations and exemplifications of this assay are known to those of skill in this art [see, Randall et al. (1957) *Arch. Int. Pharmacodyn.* 111:409–419; see, also, e.g., U.S. Pat. Nos. 5,434,292, 5,369,131, 5,345,943, 5,242, 944, 5,109,135, see Examples, below].

The pain threshold is measured in this method as the amount of pressure in mm Hg required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Air pressure from an air line is admitted through a needle valve to a syringe into a pressure gauge which is connected by a T-tube. The syringe is mounted with a plunger downward, to which is connected a short bullet-shaped wooden peg. The pressure is applied through the wooden tip to the plantar surface of the rat's foot at a specified rate of mm Hg per second. The end point is said to have been reached when the rat starts struggling.

Typically, rats, such as albino rats (120–170 g) of the Charles River Sprague-Dawley strain, or other laboratory strain are used. Hyperalgesia [inflammation] is produced by the injection of 0.1 ml of a 20% suspension of Brewer's yeast into the plantar surface of the rat's hind foot. Thresholds can be determined using a modified apparatus described in Winter and Flataker [(1965) *J. Pharm. Exp. Ther.* 148:373]. The pain threshold is measured as the pressure in mm Hg required to induce the desired response [a sharp audible squeak and/or struggle] when pressure is applied to the foot. Air pressure from an air line [or other source, such as a vice] is admitted through a needle valve to a 20 ml glass syringe and to a pressure gauge. Pressure is applied to the foot of the rat at a selected rate. The agent compound to be tested is administered typically 2 hours after the yeast injection and threshold response is determined. These results are compared with the results obtained from controls, typically a yeast-treated, saline control group. Analgesic activity was determined in terms of the percentage of inhibition of response:

Inhibition (%)=Threshold of the treated group−Threshold of the control group/Threshold of the control group×100

(d) Tail-pinch or Tail Clip Test in Rats with Hyperalgesia Induced by Freund's Adjuvant Desiccated *Mycobacterium butyricum* [such as that obtainable from Difco Laboratories, Detroit, Mich.] is ground in a mortar, suspended in liquid paraffin, sterilized in an autoclave, and injected (0.5 mg in 0.1 ml, s.c.) in the distal region of the tail of a rat, such as a Sprague-Dawley rat weighing 120 g to 170. Within a few hours of injection, animals that are so-treated exhibit hypersensitivity [hyperalgesia] to pressure placed on the tail and can be used, typically in 18 to 24 hours after injection as models to test the effectiveness of compounds in alleviating the hyperalgesia [see, e.g., U.S. Pat. No. 5,242,944]. The hypersensitivity of the tail can be examined by applying gentle pressure (using one's fingers) to the injected area. This gentle squeeze or "tail pinch" elicited a "squeak" from the animal. Five such stimuli are typically given at 4-second intervals. If the animal emits no more than one squeak in five trials, it is recorded as not having hyperalgesia and given a rating of 0. If more than one squeak is emitted, the animal is recorded as having hyperalgesia and is assigned a rating of 1. This test is administered before and after administration of a test compound to ascertain whether the compound has any activity in relieving the hyperalgesia. This activity can be quantitated dividing the total rating by the number of animals tested [and if a percentage is desired, multiplying by 100] and comparing this number before and about two hours after administration of the test compound.

(e) Thermal Methods—Tail Withdrawal Assay

Typically thermal models are used to assess analgesia. They, however, can be used to assess hyperalgesia, if inflamed tissues are used. In addition, if the test is administered repeatedly resulting in inflammation, the measured response includes a hyperalgesic component.

The simplest form of these methods is the hot plate technique originally described by Woolfe and McDonalds [see, Woolfe et al. (1944) *J. Pharmacol. Exptl. Therap.* 80:300]. Originally, this method used a zinc plate with a lamp placed underneath. In a later modification it uses an electric lamp as the source of heat and a copper plate for the conduction of heat [Eddy et al. (1953) *J. Pharmacol Exptl. Therap.* 107:385]. The first sign of discomfort is usually expressed as an attempt to sit up and lick the forepaws by the experimental animal. This is taken to be an indication of a threshold under the predetermined conditions. Dancing and jumping about by an undrugged animal is taken as an indication of unbearable pain; whereas drugged animals more commonly withdraw the hind paws and keep them close to their abdomen.

In the wire technique, heat is applied from a wire coiled inside an asbestos plate. The animal's tail is placed in a channel made in the plate [Davis et al. (1946) *J. Pharmacol.* 1:255]. Yet another thermal method uses light from a headlamp focused on the tip of the tail of an animal [D'Amour et al. (1941) *J. Pharmacol. Exptl. Therap.* 72:74]. This method measures the time between the application of the heat and the flick of the tail and has therefore been called the "tail flick" method. Another thermal method uses a light bulb focused on the loin of an animal which is protected by a plexiglass shield having a port and a shutter positioned between a lens and the animal. When the shutter is opened the timer starts and when the animal reacts the shutter is closed and the timer stopped [Ercoli et al. (1945) *J. Pharmacol. Exptl. Therap.* 84:301]. This method applies an incident light the strength of which can be varied by means of a rheostat.

The preferred tail withdrawal method for use herein is the rat tail withdrawal reflex model [modified from D'Amour et al. (1941) *Pharmacol. Exp. Ther.* 72:74–79; see, e.g.,Gamse (1982) *Naunyn-Schmiedeberg's Arch. Pharmacol.* 320:205–216; U.S. Pat. Nos. 5,387,688; 3,714,159; and 5,112,596]. Male Sprague-Dawley rats are anesthetized and implanted with femoral vein cannulae and allowed to recover overnight. After recovery, the test compounds are administered intravenously through the cannula and effects of tail withdrawal latency are measured.

Tail withdrawal latency is measured as the time to tail movement by the rat after exposure of the tail to a radiant heat source. The heat source is calibrated to produce a temperature of 62° C. after 15 seconds. Tail withdrawal latency in control animals [the absence of an opioid drug] is six to eight seconds. Test compounds demonstrating opioid activity prolong tail withdrawal latency beyond that seen in the absence of drugs. A maximal latency cut-off of fifteen seconds is imposed to prevent tissue damage. The assay is verified with known opioids as standards. Results of these studies are expressed as $ED_{50}$ concentration values, calculated as the dose producing a tail withdrawal latency equal to half the difference between the maximum latency (15 seconds) and the baseline latency (six to eight seconds). $ED_{50}$ values typically are expressed as milligrams of compound/kilogram of body weight. Duration of action is defined as the time (in minutes) necessary for the tail withdrawal response to return to baseline values after being elevated in response to drug administration. Duration of action is measured at the lowest dose producing a fifteen second (maximum) tail withdrawal latency.

(f) Other Mechanical Methods [See the Randall-Selitto] Method Described above]

These methods, other than the Randall-Selitto method, are generally used for the primary screening of analgesics. Surgical blades adapted in various manners are used in the most primitive of these methods to produce a pain reaction. The blade is applied with a graded forceps and the amount of pressure necessary to elicit pain is expressed as the number of steps required in order to produce a squeak in the experimental animal. The pressure exercised by the blades of the forceps has also been measured by placing a dynamometer between the handles of the forceps. Artery clamps or clips have also been used instead of forceps. In humans, mechanical pressure has been applied over bone structures or by eliciting visceral pain such as in the enteric canal or in the esophagus by introducing and inflating balloons therein. The amount of pressure required to produce pain can be measured by means of a manometer but the subject itself is the one to report the degree of pain.

3. Tests for Anti-diarrheal Activity (a) Castor Oil Test in Rats [see, e.g., Niemegeers et al. (1972) *Arzneim Forsch* 22:516–518; U.S. Pat. Nos. 4,867, 979; 4,990,521; 4,824,853]

Rats are fasted overnight. Each animal is treated intravenously with the desired dose of the compound to be tested. One hour thereafter, the animal receives 1 ml of castor oil orally. Each animal should be kept in an individual cage and about 2 hours after the castor oil treatment, each animal is assessed for the presence or absence of diarrhea. The $ED_{50}$ value is determined as that dose in mg/kg body weight at which no diarrhea is present in 50% of the tested animals.

For example, young female Wistar rats (230–250 g body weight) are fasted overnight and in the morning each animal is treated orally with a dose level of the compound to be tested. One hour thereafter, the animal receives 1 ml of castor oil orally. Each animal is kept in an individual cage. At different selected time intervals (e.g., 1, 2, 3, 4, 6 and 8 hrs) after the castor oil treatment, the presence or absence of diarrhea is noted. In more than 95% of 500 control animals, severe diarrhea is observed 1 hour after treatment with castor oil. Using this all-or-none criterion, a significant positive effect occurs with the tested compound if no diarrhea is observed 1 hour after the castor oil treatment. A minimum of 5 dose levels are used per drug, each dose level being given to 10 rats on ten different days. The $ED_{50}$ value, i.e., the dose level at which such effect is observed in 50% of the animals, for the compounds, such as the compounds of formula (II), generally ranges from about 0.01 to about 10 mg/kg.

(b) Castor Oil Test in Mice [See, e.g., U.S. Pat. No. 4,326,075

Groups of mice are orally dosed with test compound and one-half hour later all mice are given 0.3 ml of castor oil. Three hours after castor oil administration, all of the mice are checked for diarrhea and the dose of testing compound which protected 50% of the mice from diarrhea is the $ED_{50}$ dose.

(c) Ricinus Oil Test [See, e.g., U.S. Pat. No. 4,990,521]

Rats, such as female Wistar rats or other laboratory strains, are fasted overnight. Each animal is treated orally with a dose level of the test compound. One hour thereafter, the animal is given an amount, typically 1 ml, of ricinus oil orally. Each animal is kept in an individual cage and 1 hour after the ricinus oil treatment, the presence or absence of diarrhea is noted. The $ED_{50}$ value is determined as that dose in mg/kg body weight at which no diarrhea is present in 50% of the treated animals.

(d) Antagonism of $PGE_2$-induced Diarrhea in Mice

Anti-diarrheal activity can be determined by assessing the effects of a compound as an antagonist of $PGE_2$-induced diarrhea in mice [see, e.g., Dajani et al. 1 975) *European Jour. Pharmacol.* 34:105–113; and Dajani et al. (1977) *J. Pharmacol. Exp. Ther.* 203:512–526; see, e.g., U.S. Pat. No. 4,870,084]. This method reliably elicits diarrhea in otherwise untreated mice within 15 minutes. Animals that are pretreated with the test agent in which no diarrhea occurs are considered protected by the test agent. The constipating effects of test agents are measured as an "all or none" response, and diarrhea is defined as watery unformed stools, very different from normal fecal matter, which has well-formed boluses, and is firm and relatively dry.

Standard laboratory mice, such as albino mice of the Charles River CD-1 strain, are used. They are typically kept in group cages. The weight range of the animals when tested is between 20–25 g. Pelleted rat chow is available ad libitum until 18 hours prior to testing, at which time food is withdrawn. Animals are weighed and marked for identification. Five animals are normally used in each drug treatment group and compared with controls. Mice weighing 20–25 g are housed in group cages, and fasted overnight prior to testing. Water is available. Animals are challenged with $PGE_2$ [0.32 mg/kg i.p. in 5% ETOH] one hour after test drug treatment, and immediately placed individually, for example, in transparent acrylic boxes. A disposable cardboard sheet on the bottom of the box is checked for diarrhea on an all or nothing basis at the end of 15 minutes.

As discussed in detail above, the identification of suitable antihyperalgesic compounds for use in the present methods and compositions involve comparing the B/A ratio of test compounds to the B/A ratio of a standard compound (diphenoxylate). As would be apparent to one skilled in the art, to best assure accuracy in the comparison of the B/A ratio for a test compound to the B/A ratio for diphenoxylate, the test compound and diphenoxylate should be assessed under substantially the same conditions.

C. Formulation of Compositions for in vivo Use and Methods of Use

Effective concentrations of one or more of antihyperalgesic compounds or pharmaceutically acceptable derivatives thereof are mixed with a suitable pharmaceutical carrier or vehicle for topical or local administration. Compounds are included in an amount effective for reducing the hyperalgesic state for which treatment is contemplated. The concentration of active compound in the composition will depend on absorption, inactivation, excretion rates of the active compound, the dosage schedule, and amount administered as well as other factors known to those of skill in the art. Generally, the dosages are higher, typically at least about 5 to 10 fold, than the amount delivered when administered orally or rectally for diarrhea or when administered as for treatment of respiratory disorders, and, if necessary may be empirically determined.

Pharmaceutical carriers or vehicles suitable for administration of the compounds and for the methods provided herein include any such carriers known to those skilled in the art to be suitable for the particular mode of administration. In addition, the compounds may be formulated as the sole pharmaceutically active ingredient in the composition or may be combined with other active ingredients.

Typically a therapeutically effective dosage is formulated to contain a concentration [by weight] of at least about 0.1% up to about 50% or more, and all combinations and subcombinations of ranges therein. Preferably, the compositions are formulated to contain the active compound or compound (s) in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30% being more preferred. In even more preferred embodiments, the compositions contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 1 6, 1 5, 14, 13, 12, 11 or 10% being still more preferred. In yet more preferred embodiments, the compositions contain from greater than about 1% for example, about 2%, to less than about 10%, for example about 9 or 8%, with concentrations of greater than about 2%, for example, about 3 or 4%, to less than about 8%, for example, about 7 or 6% being still more preferred. In certain particularly preferred embodiments, the active agent is present in a concentration of about 5%. In all embodiments, amounts may be adjusted to compensenate for differences in amounts of active ingredients actually delivered to the treated tissue.

The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The compound may be suspended in micronized or other suitable form or may be derivatized to produce a more soluble active product or to produce a prodrug, or where the compound is a prodrug, to use the active form. The form of the resulting mixture depends upon a number of factors, including the intended mode of administration and the solubility of the compound in the selected carrier or vehicle. The effective concentration is sufficient for ameliorating the hyperalgesic condition and may be empirically determined.

Compounds are typically included at concentrations 0.001% [by weight] or greater than 1% up to 50% or higher [for purposes herein the concentrations are set forth with reference to loperamide; for other compounds the concentrations may be greater or lesser depending upon their relative potency as anti-hyperalgesics compared to loperamide]. The concentration is generally greater than the concentration for systemic administration of the compound as an anti-diarrheal. Preferable concentrations [by weight] are in the range of 0.01% to about 25%, more preferably 1% to 25%, yet more preferably greater than about 1% to about 10%, and most preferably greater than 1% up to about 5%. Aqueous suspensions and compositions contain 1% or more.

The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, or any other formulation suitable for topical or local administration.

The intended route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection. The compositions provided herein may be applied topically or locally to various areas in the body of a patient. As noted above, topical application is intended to refer to application to the tissue of an accessible body surface, such as, for example, the skin (the outer integument or covering) and the mucosa (the mucous-producing, secreting and/or containing surfaces). Thus, as used herein, topical application refers to applications that provide no or substantially no systemic delivery and/or systemic administration of the active compounds in the present compositions. Exemplary mucosal surfaces include the mucosal surfaces of the eyes, mouth (such as the lips, tongue, gums, cheeks, sublingual and roof of the mouth), larynx, esophagus, bronchial, nasal passages, vagina and rectum/anus; in some embodiments, preferably the mouth, larynx, esophagus, vagina and rectum/anus; in other embodiments, preferably the eyes, larynx, esophagus, bronchial, nasal passages, vagina and rectum/anus; and in still other embodiments, preferably the vagina and rectum/anus. As noted above, local application herein refers to application to a discrete internal area of the body, such as, for example, a joint, soft tissue area (such as muscle, tendon, ligaments, intraocular or other fleshy internal areas), or other internal area of the body. Thus, as used herein, local application refers to applications which provide substantially no systemic delivery and/or systemic administration of the active agents in the present compositions. Also, local application is intended to refer to applications to discrete areas of the body, that is, other than the various large body cavities (such as, for example, the peritoneal and/or pleural cavities).

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect [i.e., prevention or amelioration of hyperalgesia] in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an anti-hyperalgesic effective amount of one or more the compounds selected as described herein, preferably one of those of the above-defined formula (I), in an effective concentration range [by weight], between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1%, more preferably 2%.

To formulate a composition, the weight fraction of compound is dissolved, suspended, dispersed, or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Generally speaking, the characteristics of a composition for topical and/or local administration may be tailored for the particular condition being treated, as well as the particular surface and/or location of the body to which the compositions are being administered, by the selection of suitable vehicle or vehicles. The selection of a suitable vehicle may be achieved by one of ordinary skill in the art without undue experimentation, in light of the disclosure herein.

Generally speaking, the compositions provided herein are preferably formulated to possess certain desirable and beneficial characteristics. In this connection, the compositions preferably provide a desirable efficacy.

With respect to topical and/or local administration of the present compositions [as these terms are defined herein], desirable efficacy may involve, for example, penetration of the active ingredient, such as the compounds of formula (I), into the skin and/or tissue to substantially reach the hyperalgesic site to provide desirable anti-hyperalgesic pain relief. The efficacy of the present compositions may be about the same as that achieved, for example, with central opiate analgesics. But, as discussed in detail herein, the efficacy achieved with the present compositions is preferably obtained without the undesirable effects that are typically associated with central opiates including, for example, respiratory depression, sedation and constipation.

The compositions described herein are also preferably non-irrating and/or non-sensitizing to the skin or other tissues proximate to the site(s) of administration. In addition, the compositions provided herein also preferably provide a sustained delivery of active ingredient to provide antihyperalgesic efficacy over a period of time, including extended periods of time, preferably for at least about 6 hours, more preferably at least about 12 hours, and even more preferably at least about 24 hours (or about a day). These compositions are preferably compatible with other topical and/or local treatments that a patient may receive at or about the same time that the compositions are administered to the patient according to the methods described herein. Such additional topical or local treatments include, for example, topical treatments that may be used in connection with patients suffering from second and/or third degree burns. In addition, the present compositions are preferably physiologically compatible, that is, the present compositions are preferably substantially isotonic and/or possess about a neutral pH. The compositions described herein are preferably easily administered topically and/or locally. Specifically, the compositions are preferably substantially fluid to provide ease of administration, but also remain at the site of application without run off. The compositions are also desirably water washable for ease of cleanup and removal from skin and/or tissue (when desired). Other desirable and beneficial characteristics of the compositions described herein, in addition to those described above, would be apparent to one skilled in the art, once armed with the present disclosure.

Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, moisterizers, including lactic acid, ammonium lactate and urea, skin penetration enhancers, coloring agents, fragrances, emulsifiers, thickening agents, and solvents.

In connection with certain preferred embodiments herein that involve aqueous vehicles, the vehicles also preferably contain a salt of phosphoric acid ($H_3PO_4$). Such salts of phosphoric acid include monobasic salts ($MH_2PO_4$), dibasic salts ($M_2HPO_4$) and tribasic salts ($M_3PO_4$), where M is a metallic element, for example, an alkali metal, such as sodium (Na) or potassium (K), or an alkaline earth metal, such as magnesium (Mg) or calcium (Ca). Preferably, the compositions contain at least two of the monobasic, dibasic and tribasic salts of phosphoric acid. More preferably, the compositions contain a monobasic and dibasic salt of phosphoric acid. The concentration of the salt or salts of phosphoric acid employed in the compositions may vary and depends, for example, on the particular salts selected, the other components of the compositions, the form of the composition (for example, emulsion, suspension, cream and/or lotion), and the intended use, including topical or local use.

In preferred embodiments which involve compositions that contain monobasic and dibasic salts of phosphoric acid, the compositions preferably contain from greater than 0 to about 10 wt. % (based on the total weight of the composition) of a monobasic salt of phosphoric acid, with from greater than 0 to about 5 wt. % being more preferred. Even more preferably, the compositions contain from about 0.1 to about 0.5 wt. % of a monobasic salt of phosphoric acid, with about 0.2 wt. % being still more preferred. Also in preferred embodiments, the compositions contain from greater than 0 to about 10 wt. % (based on the total weight of the composition) of a dibasic salt of phosphoric acid, with from about 0.1 to about 5 wt. % being more preferred. Even more preferably, the compositions contain from about 1 to about 2 wt. % of a dibasic salt of phosphoric acid, with about 1.3 wt. % still more preferred.

As noted above, the compositions may also contain a tribasic salt of phosphoric acid. In these embodiments, the compositions preferably contain from greater than 0 to about 10 wt. % (based on the total weight of the composition) of a tribasic salt of phosphoric acid, with from greater than 0 to about 5 wt. % being more preferred. More preferably, the compositions contain from about 0.1 to about 1 wt. % of a tribasic salt of phosphoric acid, with about 0.6 wt. % even more preferred.

Also in certain preferred embodiments, including embodiments that involve aqueous vehicles, the compositions may also contain a glycol, that is, a compound containing two or more hydroxy groups. A glycol which is particularly preferred for use in the compositions is propylene glycol. In these preferred embodiments, the glycol is preferably included in the compositions in a concentration of from greater than 0 to about 5 wt. %, based on the total weight of the composition. More preferably, the compositions contain from about 0.1 to less than about 5 wt. % of a glycol, with from about 0.5 to about 2 wt. % being even more preferred. Still more preferably, the compositions contain about 1 wt. % of a glycol.

Other formulation variations may also be employed, as desired, as described below and elsewhere herein.

For local internal administration, such as intra-articular administration, the compounds are preferably formulated as a solution or a suspension in an aqueous-based medium, such as isotonically buffered saline or are combined with a biocompatible support or bioadhesive intended for internal administration.

1. Lotions

The lotions, which, for example, may be in the form of a a suspension, dispersion or emulsion, preferably contain an effective concentration of one or more of the compounds. The effective concentration is preferably effective to deliver an anti-hyperalgesic amount, typically at a concentration of between about 0.1–50% [by weight] or more of one or more of the compounds provided herein. The lotions also contain [by weight] from 1% to 50%, preferably from 3% to 15%, of an emollient and the balance water, a suitable buffer, a $C_2$ or $C_3$ alcohol, or a mixture of water or the buffer and the alcohol. Any emollients known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include. but are not limited to, castor oil, safflower oil, cotton seed oil, corn oil, olive oil, cod liver oil, almond oil, avocado oil, palm oil, sesame oil, and soybean oil.

(d) Acetoglyceride esters, such as acetylated monoglycerides.

(e) Ethoxylated glycerides, such as ethoxylated glyceryl monstearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids.

(i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly(ethylene oxide) homopolymers [M.W. 100,000–5,000,000], polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), $C_{15}$–$C_{18}$ vicinal glycol and polyoxypropylene derivatives of trimethylolpropane.

(n) polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain [by weight] from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers includ, but are not limited to, the fatty acid soaps, e.g. sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound, such as loperamide, is dissolved, suspended or otherwise uniformly dispersed in the mixture.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams are formulated to contain concentration effective to deliver an anti-hyperalgesic effective amount of the compound to the treated tissue, typically at between about 0.1%, preferably at greater than 1% up to and greater than 50%, preferably between about 3% and 50%, more preferably between about 5% and 15% of one or more the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included is in the composition at a level from 3% to 50%, preferably from 5% to 20%.

3. Solutions and Suspensions for Topical and Local Administration

The solutions are formulated to contain an amount of one or more compounds effective to deliver a an anti-hyperalgesic amount, typically at a concentration [by weight] of between about 0.1–50%, preferably at least more than 1%, more preferably more than 2%, of one or more of the compounds provided herein. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol, and mixtures thereof. Such solvent systems can also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and alkyl parabens such as methyl parabens; antioxidants, such as ascorbic acid and sodium bisulfite; chelating agents, such as ethylenediaminetetraacetic acid [EDTA]; buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or, may be formulated as an aerosol or foam and applied to the skin as a spray-on. The aerosol compositions typically contain [by weight] from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspensions may also be topically applied to the eyes and mucosa. Solutions, particularly those intended for ophthalmic use, may be formulated as 0.01%–10% isotonic solutions, pH about 5–7, with appropriate salts, and preferably containing one or more of the compounds herein at a concentration of about 0.1%, preferably greater than 1%, up to 50% or more. Suitable ophthalmic solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium, β-hydroxybutyrate and 5–5.5 mM glucose.

The active materials can also be mixed with other active materials, that do not impair the desired action, or with materials that supplement the desired action, including viscoelastic materials, such as hyaluronic acid, which is sold under the trademark HEALON [solution of a high molecular weight (MW of about 3 millions) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803], VISCOAT [fluorine-containing (meth)acrylates, such as, 1H,1H,2H,2H-heptadecafluorodecylmethacrylate; see, e.g., U.S. Pat. Nos. 5,278,126, 5,273,751 and 5,214,080; commercially available from Alcon Surgical, Inc.], ORCOLON [see, e.g., U.S. Pat. No. 5,273,056; commercially available from Optical Radiation Corporation], methylcellulose, methyl hyaluronate, polyacrylamide and polymethacrylamide [see, e.g., U.S. Pat. No. 5,273,751]. The viscoelastic materials are present generally in amounts ranging from about 0.5 to 5.0%, preferably 1 to 3% by weight of the conjugate material and serve to coat and protect the treated tissues. The compositions may also include a dye, such as methylene blue or other inert dye, so that the composition can be seen when injected into the eye or contacted with the surgical site during surgery.

4. Gels

Gel compositions can be formulated by simply admixing a suitable thickening agent to the previously described solution or suspension compositions. Examples of suitable thickening agents have been previously described with respect to the lotions.

The gelled compositions contain an effective amount of one or more an anti-hyperalgesic amount, typically at a concentration of between about 0.1–50% by weight or more of one or more of the compounds provided herein.; from 5% to 75%, preferably from 10% to 50%, of an organic solvent as previously described; from 0.5% to 20%, preferably from 1% to 10% of the thickening agent; the balance being water or other aqueous or non-aqueous carrier, such as, for example, an organic liquid, or a mixture of carriers.

5. Solids

Compositions of solid forms may be formulated as stick-type compositions intended for application to the lips or other parts of the body. Such compositions contain an effective amount of one or more of the compounds provided herein. The amount is typically an amount effective to deliver an anti-hyperyperalgesic amount, typically at a concentration of between about 0.1–50% or more of one or more of the compounds provided herein. The solids also contain from about 40% to 98%, preferably from about 50% to 90%, of the previously described emollients. This composition can further contain from 1% to 20%, preferably from 5% to 15%, of a suitable thickening agent, and, if desired or needed, emulsifiers and water or buffers. Thickening agents previously described with respect to lotions are suitably employed in the compositions in solid form.

Other ingredients, such as preservatives, including alkyl parabens such as methyl paraben and ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

6. Additional Ingredients

Other active ingredients, include, but are not limited to antibiotics, antivirals, antifungals, anti-inflammatories, including steroidal and non-sterodial anti-inflammatories, vasoconstrictors such as epinephrine, anesthetics and mixtures thereof. Such additional ingredient include any of the following, further including salts thereof:

a. Antibacterial Agents

Aminoglycosides, such as Amikacin, Apramycin, Arbekacin, Bambermycins, Butirosin, Dibekacin, Dihdrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid, and Tobramycin;

Amphenicols, such as Azidamfenicol, Chloramphenicol, Chloramphenicol Palmitate, Chloramphenicol Pantothenate, Florfenicol, Thiamphenicol;

Ansamycins, such as Rifamide, Rifabutin, Rifampin, Rifamycin, and Rifaximin;

β-Lactams;

Carbapenems, such as Imipenem;

Cephalosporins, such as 1-Carba (dethia) Cephalosporin, Cefaclor, Cefactor, Cefadroxil, Cefamandole, Cefatrizine, Cefazedone, Cefazolin, Cefixime, Cefmenoxime, Cefmetazole, Cefodizime, Cefonicid, Cefoperazone, Ceforanide, Cefotaxime, Cefotetan, Cefotiam, Cefoxitin, Cefpimizole, Cefpirimide, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonam;

Oxacephems such as Flomoxef and Moxolactam;

Penicillins such as Amidinocillin, Amdinocillin Pivoxil, Amoxicillin, Ampicillan, Apalcillin, Aspoxicillin, Azidocillan, Aziocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Meziocillin, Nafcillin, Oxacillin, Penamecillin, Penethamate Hydriodide, penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Dirithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Apicycline, Aztreonam, Chlortetracycline, Clomocycline, Colistimethate, Demeclocycline, Doxycycline, Elindamycin, lindamycin, Guamecycline, Linccomycin, Loracarbef, Lymecycline, Meclocycline, Methacycline, Minocycline, Novobiocin, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$-Formyl-sulfisomidine, $N^4$-β-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethane-sulfonic Acid Triethanolamine Salt, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid,p-Sulfanilylbenzylamine, p,p'-Sulfonyldianiline-N,N' digalactoside, Sulfoxone and Thiazolsulfone;

Others such as Benzoyl Peroxide, Clofoctol, Hexedine, Magainins, Methenamine, Methenamine Anhydromethylene-citrate, Methenamine Hippurate, Methenamine Mandelate, Methenamine Sulfosalicylate, Nitroxoline, Silver Nitrate, Squalamine, and Xibornol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole Nitrate, Sulconazole and Tioconazole;

Triazoles such as Fluconazole, Itraconazole, Terconazole

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-inflammatory Agents

Corticosteriods such as Alclometasone, Betamethasone, Clobetasol, Clocortrolone, Desonide, Desoximetasone, Dexamethasone, Diflorasone, Fluocinolone, Fluocinonide, Flurandrenolide, Fluticasone, Floromethalone, Halcinonide, Halobetasol, Hydrocortisone, Loteprednol, Mometasone, Prednicarbate, Prednisone, and Triamcinolone;

Aminoarylcarboxylic Acid Derivatives such as Etofenamate, Meclofenamic Acid, Mefanamic Acid, Niflumic Acid;

Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Naproxin, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine.

Arylpropionic Acid Derivatives such as Bucloxic Acid, Carprofen, Fenoprofen, Flunoxaprofen, Ibuprofen, Ibuproxam, Oxaprozin, Phenylalkanoic Acid derivatives such as Flurbiprofen, Piketoprofen, Pirprofen, Pranoprofen, Protizinic Acid and Tiaprofenic Acid;

Pyranocarboxylic acids such as Etodolac;

Pyrazoles such as Mepirizole;

Pyrazolones such as Clofezone, Feprazone, Mofebutazone, Oxyphinbutazone, Phenylbutazone, Phenyl Pyrazolidininones, Suxibuzone and Thiazolinobutazone;

Salicylic Acid Derivatives such as Aspirin, Bromosaligenin, Diflusinal, Fendosal, Glycol Salicylate, Mesalamine, 1-Naphthyl Salicylate, Magnesium Salicylate, Olsalazine and Salicylamide, Salsalate, and Sulfasalazine;

Thiazinecarboxamides such as Droxicam, Isoxicam and Piroxicam

Others such as ε-Acetamidocaproic Acid, Acetaminophen, S-Adenosylmethionine, 3-Amino-4-hydroxybutyric Acid, Amixetrine, Bendazac, Bucolome, Carbazones, Cromolyn, Difenpiramide, Ditazol, Hydroxychloroquine, Indomethacin, Ketoprofen and its active metabolite 6-methoxy-2-naphthylacetic acid; Guaiazulene, Heterocylic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4, 6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bornyl Chloride, Calcium lodate, Iodine,Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Napthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxquinoline and Sulfate; and others, such as Boric Acid, Chloroazodin, m-Cresyl Acetate, Cupric Sulfate and Ichthammol.

h. Antivirals

Purines/Pyrimidinones, such as 2-Acetyl-pyridine 5-((2-pyridylamino)thiocarbonyl) Thiocarbonohydrazone, Acyclovir, Dideoxyadenosine, Dideoxycytidine, Dideoxyinosine, Edoxudine, Famiciclovir, Floxuridine, Ganciclovir, Idoxuridine, MADU, pyridinone, Trifluridine, Valacyclovir, Vidrarbine and Zidovudine;

Others such as Acetylleucine Monoethanolamine, Acridinamine, Alkylisooxazoles, Amantadine, Amidinomycin, Cuminaldehyde Thiosemicarbzone, Foscarnet Sodium, Interferon α-N3, Kethoxal, Lysozyme, Methisazone, Moroxydine, Podophyllotoxin, Ribavirin, Rimantadine, Stallimycin, Statolon, Thymosins, Tromantadine and Xenazoic Acid.

i. Antihistamines

Antihistamines such as chlorcycliaine, and doxepin j. Vasoconstrictors

Vasoconstrictors, preferably such as the α-agonists, including but not limited to, epinephrine, norepinephrine, pseudoephedrine, phenylephrine, oxymetazoline, propylhexedrine, naphazoline, tetrahydrolozine, xylometazonline, ethylnorepinephrine, methoxamine, phenylhexedrine, mephentermine, metaraminol, dopamine, dipivefrin, norphedrine and ciraxzoline may be advantageously used in the compositions and methods herein. Use of such should aid in reducing systemic delivery of the active antihyperalgesic agent.

k. Local Anesthetics

Dyclonine, lidocaine and prilocaine, singly or in admixture; Benzocaine, Tretracaine, Bupiracaine, Mepivacine and Etidocaine.

Exemplary compositions are set forth in the Examples herein. It is understood that suitable combinations of any of the above additional ingredients with the compounds provided herein are also contemplated.

D. Combinations and Kits

The compounds or compositions containing the compounds may also be coated on bandages, mixed with bioadhesives or included in dressings. Thus, combinations of bandages, bioadhesives, dressings and other such materials and the compositions formulated as described herein are provided. Kits containing these combinations, which may also include compositions containing the above listed agents, are also provided.

E. Articles of Manufacture

The compounds and compositions provided herein may be packaged as articles of manufacture containing packaging material, one or more of the compounds provided herein, which is effective for ameliorating peripheral hyperalgesia, within the packaging material, and a label that indicates that the compound, N-oxide, acid, salt or other derivative thereof is used for treating and/or preventing hyperalgesic conditions.

F. Indications and Methods of Treatment

The compositions and methods herein are intended for the preventions and treatment of hyperalgesia association with numerous inflamatory conditions and injuries. The compositions and methods provided herein may be used to treat a variety of hyperalgesic conditions associated with burns, including, but not limited to, thermal, radiation, chemical, sun and wind burns, abrasions, including, for example, corneal abrasions, bruises, contusions, frostbite, rashes, including, for example, allergic, heat and contact dermatitis, such as, for example, poison ivy and diaper rashes, acne, insect bites/stings, skin ulcers, including, but not limited to, diabetic and decubitus ulcers, mucositis, inflammation, for example, periodontal inflammation, orthodontic inflammation, inflammatory conjunctivitis, hemorrhoids and venereal inflammations, gingivitis, bronchitis, laryngitis, sore throat, shingles, fungal irritation, for example, athlete's foot and jock itch, fever blisters, boils, plantar's warts or vaginal lesions, including, for example, mycotic and sexually transmitted vaginal lesions. Hyperalgesic conditions associated with skin surfaces include burns, including but not limited to, thermal, radiation, chemical, sun and wind burns, abrasions such as, for example, corneal abrasions, bruises, contusions, frostbite, rashes including allergic, heat, contact dermatitis (for example, poison ivy) and diaper rashes), acne, insect bites/stings and skin ulcers (including diabetic and decubitus ulcers). Hyperalgesic conditions of the mouth, larynx and bronchium include mucositis, post-tooth extraction, periodontal inflammation, gingivitis, orthodontic inflammation, bronchitis, laryngitis and sore throat. Hyperalgesic conditions of the eyes include corneal abrasions, post-radial keratectomy and inflammatory conjunctivitis. Hyperalgesic conditions of the rectum/anus include hemorrhoids and venereal inflammations. Hyperalgesic conditions associated with infectious agents include shingles, fungal irritations (including athlete's foot and jock itch), fever blisters, boils, plantar's warts and vaginal lesions (including lesions associated with mycosis and sexually transmitted diseases). Hyperalgesic conditions may also be associated with recovery following surgery, such as recovery following lumpectomy, episiotomy, laparoscopy, arthroscopy, radial keratectomy and tooth extraction.

Compositions for use with human skin and muscosa preferably may be applied at least once per day or, if necessary to achieve the desired result, more often, to the areas of the skin for which treatment is sought. It is understood that the precise treatment regimen depends upon the individual treated and may be ascertained empirically depending upon the formulation and, particularly, the age of the treated individual. Any regimen is acceptable as long as the desired anti-hyperalgesic effects are achieved without substantial deleterious or sustained undesirable side effects.

The methods for treating human skin are practiced by applying to the skin, preferably at least daily, a composition suitable for human skin treatment or treatment of mucosal membranes and other body surface tissues, including the vagina, rectum, mouth, eyes and other such tissues. The compositions may be injected into joints or other inflamed areas.

Compositions may be combined with bandages, bioadhesives and other dressings and applied to the body in combination therewith.

G. Preparation of Compounds Useful as Peripheral Anti-hyperalgesics

Compounds useful as peripheral anti-hyperalgesics in the methods and compositions provided herein may be prepared using standard organic synthetic techniques that which would be apparent to one of skill in the art in light of the present disclosure. Compounds of formula (I), and especially compounds where M is

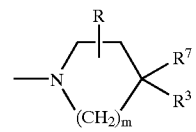

in which m is 2, R is hydrogen, $Ar^1$ and $Ar^2$ are phenyl, $R^4$ is —C(=O)—$NR^5R^6$, $R^2$ is substituted or unsubstituted alkylene of about 2 carbons, $R^3$ is Ar and $R^7$ is hydroxy (which are referred to hereinafter as compounds of formula (IA)), may be prepared, for example, by using methodology exemplified in the following exemplary reaction Schemes I and II.

Scheme I

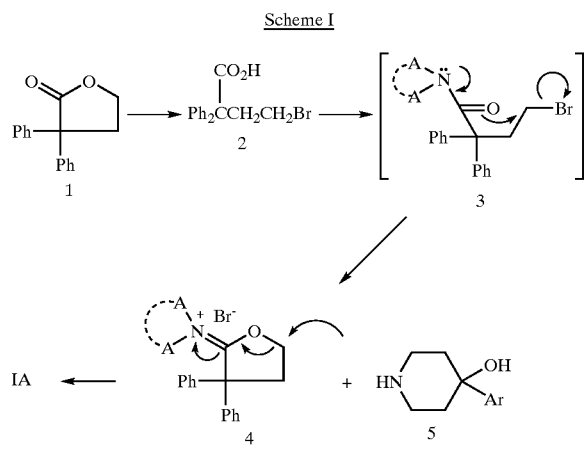

Scheme II

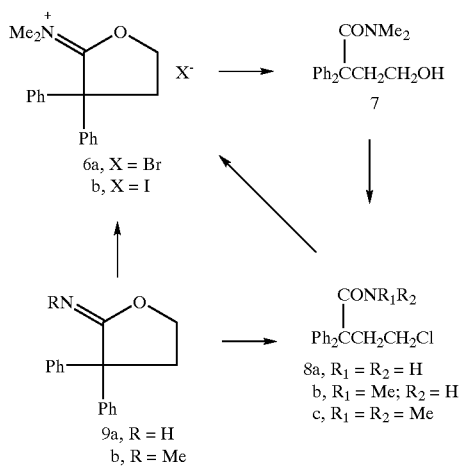

Scheme III

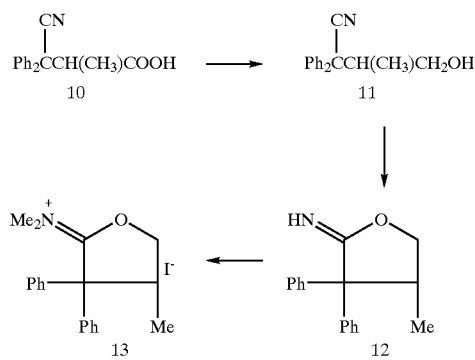

Treatment of 3-cyano-3,3-diphenylisobutyric acid (10) with $SOCl_2$, followed by reduction of the intermediate acid chloride with $NaBH_4$ in DMF, affords the corresponding alcohol (11). Acid cyclization of (11) provides tetrahydro-4-methyl-3,3-diphenyl-2-furanimine (12). Alkylation of (12), followed by quaternization, yields ammonium iodide (13). Allylation of the N,N-disubstituted 2,2-diphenylacetamide (14) with $NaNH_2$ in xylene affords the corresponding 2,2-diphenyl-4-pentenamide (15). Cyclization of (15) with HBr in AcOH provides the 5-methyl substituted ammonium bromide (16).

Methods for preparing compounds employed in the methods and compositions provided herein, including the compounds of formula (I), and especially the compounds of formula (IA), are known [see, e.g., Stokbroekx et al. (1973) J. Med. Chem. 16:782–786; see also, e.g., U.S. Pat. Nos. 3,714,159 and 3,884,916]. Other methods for preparing compounds that may be employed in the methods and compositions provided herein would be apparent to one skilled in the art in light of instant disclosure.

The following examples are included for illustrative purposes only and are not intended to limit the scope of the invention.

With particular reference to Scheme I, the synthesis of the compounds of formula (IA) may involve ring opening of 2,2-diphenyl-4-hydroxybutyric acid γ-lactone (1) with HBr in AcOH to afford 4-bromo-2,2-diphenylbutyric acid (2). Subsequent treatment of (2) with $SOCl_2$ and reaction of the intermediate acid chloride with a secondary amine yields the corresponding tetrahydro-3,3-diphenyl-2-furylidene ammonium salt (4). The compound of formula (3) rearranges to (4) spontaneously under the reaction conditions. The structure of the ammonium salt (4) may be evident from spectral data and from its reactivity. Compound (4) reacts extremely fast with 4-aryl-4-piperidinols (5) to provide the compounds of formula (IA).

With particular reference to Scheme II, treatment of dimethyl(tetrahydro-3,3-diphenyl-2-furylidene)ammonium bromide (6a) with aqueous base affords 4-hydroxy-N,N-dimethyl-2,2-diphenylbutyramide (7). Compound (7) may be converted with $SOCl_2$ to the compound (8c). Upon warming in an inert solvent, compound (8c) rearranges slowly to the corresponding ammonium salt (4). Reaction of compound (8c) with compound (5) affords the compounds of formula (IA).

Primary and secondary butyramide compounds of formula (IA) may be prepared by a substitution reaction of compounds (8a) and (8b) with a 4-aryl-4-piperidinol of formula (5). Compounds (8a) and (8b) may be synthesized by ring opening of the corresponding 3,3-diphenyl-2-iminotetrahydrofuran (9a) and (9b) with HCl. Quaternization of (9b) with MeI affords ammonium iodide (6b) and alkylation of (9a) with $LiNH_2$ and MeI yields the monomethylated compound (9b).

The β- and γ-methyl-substituted compounds of formula (IA) may be prepared by condensation of the substituted (tetrahydro-3,3-diphenyl-2-furylidene)ammonium salts (13) and (16) with the 4-aryl-4-piperidinol compounds of formula (5). The synthesis of compounds (12) and (16) is outlined in the following exemplary reaction Schemes III and IV.

EXAMPLE 1
Peripherally-mediated Antinociceptive Effects Observed During Inflammation Appear to be Mediated by μ and κ Opioids A. Materials and Methods This study was performed with approval from the Institutional Animal Care and Use Committee of the University of California, San Diego.

1. Preparation

To induce inflammation, each rat [male Sprague-Dawley, 300–340 g] was anesthetized in a Plexiglas acrylic plastic induction chamber with 2% halothane in oxygen-enriched room air. During halothane anesthesia, 0.2 ml of a mixture of 4% kaolin and 4% carrageenan [Sigma Chemical Co.] was slowly injected into the right knee joint cavity through the patellar ligament using a 21 gauge needle. After induction of the inflammation, the rat was allowed to recover from anesthesia. Three and one-half hours after induction of the inflammation, the rat was anesthetized again with halothane [2.0%] in a 50% $O_2$/air mixture delivered through a face mask. The tail artery was cannulated for monitoring BP. When surgical preparation was completed, halothane anesthesia was continued at 1.0% inspired halothane. BP was recorded continuously [Grass model 7 polygraph]. Body temperature [rectal] was monitored and maintained at 37° C. by a servo-controlled heating blanket. For intrathecal [IT]

injection, rats were prepared with chronic lumbar intrathecal catheters [Yaksh et al. (1976) *Physiol. Behav.* 17:1031–1036]. After 5–7 days, they were entered into the study.

To produce a reliable compression of the knee joint, a pediatric blood pressure cuff was placed around the inflamed knee. For stimulation, the cuff was rapidly elevated to 200 mm Hg by a syringe pump. Each inflation was sustained for 2 minutes. Typically, testing was carried out at −5 minutes, and 15, 30, 60, 90 and 120 minutes.

2. Measure of Joint Volume and Circumference

To assure a standard state of inflammation, at three and one-half hours after kaolin and carrageenan injection, the volume and circumference of the inflamed and non-inflamed knee joint were measured. Volume was assessed by displacement of fluid after the hindquarter of the rat was immersed to the groin. Circumference was measured by a flexible cord placed around the knee joint at the level of the knee joint flexure. After the first 85 rats, it was found that the inflammation was sufficiently reliable so that further screening in this fashion was not required.

3. Drug Delivery

The route of drug injection was intramuscularly [IM] into the left hamstring muscle, intrathecally [IT] through the chronic catheter, or intra-articularly [IA] into the right knee joint using a 30 gauge needle. It was also found that simple IA injection of saline [vehicle] into the already inflamed knee joint at 4 hours would result in an additional facilitated response. Thus, to compare the potency of the IT and IM routes of delivery with the IA route, all IT and IM treatments employed a concurrent IA injection of saline, in addition to the IT or IM injection. IT and IM vehicle injection had no effect upon the response and, thus, it was not necessary to give parallel IT or IM vehicle injection with IA drugs. The volume of all IM and IA drug injections was 0.2 ml, except for IM injection of U50488H 10 mg, which was in 0.6 ml. All IT administered drugs were injected in a volume of 10 $\mu$l followed by 10 $\mu$l of physiologic saline to clear the catheter.

4. Drugs

The drugs used for injection were:

mu [$\mu$] agonists: morphine sulfate [MW: 334; Merck, Sharpe and Dohme, West Point, Pa.]; Sufentanil citrate, [MW: 571 Janssen Pharmaceutical, Belgium];

kappa [$\kappa$] agonists: PD117302 [(+/−)trans-N-methyl-N[2-(1-pyrrolidinyl)-cyclohexyl-]benzo-[b]-thiophene-4-acetamide] [MW—412; Parke Davis] and U50488H (trans-3,4-dichloro-N-methyl-N-[2-(1-pyrrolidinyl)-cyclohexyl]-benzeneacetamide) [MW: 465; Upjohn, Kalamazoo, Mich.]; Spiradoline mesylate [MW: 522; Research Biochemicals Inc.];

delta [$\delta$] agonists: DADL [D-ala$^2$D-leu$^5$-enkephalin; MW: 556; courtesy Dr. Murray Goodman, UCSD]; DPDPE: [D-Pen$^2$, D-Pen$^5$]enkephalin [MW: 646, courtesy Dr. Victor Hruby, University of Arizona Health Science Center, Tucson, Ariz.]; and naloxone HCl [MW=364; Endo Labs, Garden City, N.J.].

5. Naloxone Antagonism

To define the potency of naloxone to reverse the effects of IA morphine and U50488H, rats received an injection of naloxone [intraperitoneal injection, mg/kg] given at −10 minutes before IA morphine [1 mg] IA U50488H [1 mg]. This time interval was based on preliminary observations. If the naloxone dose completely reversed the effects of the agonist, it was scored as an antagonism. In sequential rats, the naloxone dose was increased or decreased by a factor of 3 [approximately one-half log unit: 0.01, 0.03, 0.1, 0.3, 1.0, 3.0 or 10.0 mg/kg] if the preceding naloxone dose was either ineffective or effective [e.g., the Dixon up-down method] for potency determination [Dixon, W J (1965) *Am. Stat. Ass. J.* 60:67–978].

6. Statistics:

BP was evaluated as the mean BP: [(systolic BP-diastolic BP)/3+diastolic BP]. The response to a compression stimulus was expressed as $\Delta$ mean BP [(maximum mean blood pressure response observed during knee joing compression)−(mean blood pressure response observed immediately prior to knee joint compression)]. For dose response analysis, data are presented as the %$\Delta$BP [maximum $\Delta$ mean BP measured after drug)/maximum $\Delta$ mean BP measured before drug)]×100. Statistical comparisons were carried out using a Student's t-test, paired or unpaired as required. For statistical analysis and graphical presentation, BP dose response curves were generated using the maximum reduction in the evoked response [% $\Delta$BP] observed within 60 minutes after drug injection. These dose response data were analyzed by calculation of a least-squares linear regression. ED$_{50}$ and slopes with 95% confidence interval [CI] were calculated [Tallarida et al.(1986) *Manual of Pharmacologic Calculations with Computer Programs,* 2nd ed., New York, Springer-Verlag].

B. Results

1. General Observations

In all experiments, the injection of kaolin and carrageenan induced inflammation, with swelling and edematous deformation of the joint. The volume of the right injected hindlimb was measured in the first 85 rats and found to be 6.6±0.1 versus 14.6±0.5 ml, respectively, before and after kaolin and carrageenan injection [n=85; $\Delta$=+1.8±0.1 ml, p<0.01, paired t-test]. Injection of saline alone resulted in a small, but not statistically significant, increase in the circumference of the injected knee joint. The left, uninjected knee, was not different from the right knee prior to kaolin and carrageenan and did not change during the study [p>0.10, paired t-test data, not shown]. Prior to blood pressure response testing, it was observed that all rats displayed a tendency to keep the injected limb from weight bearing. Unstimulated rats [n=193], maintained in an anesthetic state with inspired 1.0% halothane, displayed a stable resting BP [121±6 mm Hg]. Inflation of the cuff on the inflamed knee joint resulted in a reliable stimulation-dependent increase in BP during the 2 minute interval of inflation [$\Delta$=14.6±0.2 mmHg]. With knee joint compression, the time course of the increasing BP evoked by compression was uniform, reaching the maximum response approximately 20–30 seconds after the onset of stimulation. The BP changes persisted throughout 2 minutes of stimulation and gradually returned to the control level within 1–2 minutes after the end of the stimulus.

In the absence of drug treatment, the response to compression was stable over the 2 hour interval of testing.

2. Intrathecal Opioid Agonists

The IT administration of $\mu$, $\delta$ and $\kappa$ agonists at the doses employed had no statistically significant effect upon resting blood pressure, but resulted in an early blockade of the cuff-evoked increase in BP. The antinociceptive effects were dose dependent. The order of drug activity on the cuff-evoked BP responses was sufentanil>PD117302>spiradoline, morphine>DADL, DPDPE>U-50,488H >naloxone=0.

3. Intramuscular Opioid Agonist-cardiovascular Response

To determine if the IA effects could be similarly achieved by a "systemic" route of delivery, the intramuscular [IM] administration of these agents was also examined. IM $\mu$ opioid agonists resulted in a blockade of the compression-evoked increase in BP. The ordering of activity was sufentanil>PD117302, Spiradoline, morphine>DADL, DPDPE>U-50,488H=naloxone=0.

4. Naloxone Antagonism

The effects of IM naloxone on the depressive effects of IA morphine [1 mg] and IA U50488H were determined. Naloxone alone was without effect upon a compression-evoked change in BP. To determine if the effects of naloxone were local, within the articular space, naloxone [30 μg] was co-administered with morphine in 4 rats. This injection was adequate to attenuate the anti-hyperalgesic effects of morphine otherwise observed at 30 minutes after agonist injection.

C. Discussion

1. Spinal Opioid Agonists and Antinociception

The compression evoked increase in BP was effectively blocked by the intrathecal delivery of morphine, sufentanil [μ] and DPDPE and DADL [δ], PD117304, spiradoline and U50488 [κ]. Spinally delivered opioid μ and δ agonists have been shown to depress the behavioral and electrophysiological responses evoked by noxious stimulation. In contrast, κ agonists frequently appear to have modest effects in behavioral models of acute nociception [such as the tail flick or hot plate models], but typically appear to be more efficacious in models of protracted pain [typically induced by inflammatory stimuli as in the present model]. Given the lack of significant changes in resting blood pressure with the spinal agent, it appears that these agents are blocking the response by a blockade of small afferent input generated by the compression of the inflamed knee.

2. Intra-articular Opioid Agonists and Antinociception

The experiments demonstrated that IA administered μ and κ, but not δ, preferring agonists result in a dose dependent blockade of the hyperalgesia produced by the inflammation of the knee. Importantly, as defined by the dose response curves, the effects produced by injection at the site is more robust and potent than when the respective agent is delivered intramuscularly. This observation indicates that the effect of IA μ and κ agonists appear to be mediated by a local action at the site of injection. This local action is further supported by the observation that local naloxone was able at a very low dose to attenuate the effects of IA morphine. The local dose required to induce this blockade considerably exceeds that dose required after spinal delivery. This difference in potency by the two "local" routes may reflect the accessibility of the joint to the drug. Alternately, the high dose may reflect upon the fact that a high level of occupancy is required to block the transduction.

Antagonism of the effect of IA morphine and U50488H is consistent with the known lower affinity of naloxone for the κ receptor than for the μ receptor and indicates that both classes of receptors appear to be involved in this action. The failure of DPDPE and DADL to induce a comparable action may be due to the absence of delta receptors at this site or to a difference in bio-availability.

EXAMPLE 2

The Effects of Intra-articular Loperamide were Compared with Those of Morphine Delivered into the Inflamed Knee Joints of Rats A. Model In joint inflammation, the peripheral nerve innervating inflamed tissue evokes an exagerated behavior response to otherwise innocuous stimuli (i.e. a state of hyperalgesia). This scenario has been well-documented in the knee joint. It has been shown that inflammation of the knee joint results in, among other responses, signs of a pain-associated autonomic reaction, including increased BP.

B. Methods

1. Induction of Inflammation

Male rats [Sprague-Dawley, 300–340 g] were anesthetized with 2% halothane in oxygen-enriched room air. To induce inflammation, during halothane anesthesia 0.2 ml of a mixture of 4% kaolin and 4% carrageenan [Sigma Chemical Co.] was injected into the right knee joint cavity through the patellar ligament using a 21 gauge needle. This induces an experimental arthritis and model of hyperalgesia.

After induction of the inflammation, the rat was allowed to recover from anesthesia. Three and half hours after induction of the inflammation, the rat was anesthetized again with halothane [2.0%] in oxygen-enriched air. The tail artery was cannulated for monitoring BP. When surgical preparation was completed, halothane anesthesia was continued at 1.0% inspired halothane. BP was recorded continuously [Grass model 7 polygraph]. Body temperature [rectal] was monitored and maintained at 37° C. by a servo-controlled heating blanket. To produce a reliable compression of the knee joint, a pediatric blood pressure cuff was placed around the inflamed knee. For stimulation, the cuff was rapidly elevated to 22 mm Hg by a syringe pump. Each inflation was sustained for 2 minutes. It has been demonstrated that such compression results in a reliable stimulus dependent hypertension [Δ≈13 mm Hg].

2. Drugs and Drug Delivery

Drugs were delivered either intramuscularly [IM] into the left hamstring muscle, or intra-articularly [IA] into the right knee joint using a 30 gauge needle. The volume of all IM and IA drug injections was 0.2 ml. Drugs used for injection were: morphine sulfate [Merck, Sharpe and Dohme, West point, Pa.], and loperamide HCl [Research Biochemicals, Natick, Mass.]. All drugs were dissolved in dimethylsulfoxide [DMS, spectral grade] and diluted with 5% methylcellulose [Sigma]. Naloxone HCl [Dupont] was prepared in saline for intraperitoneal [IP] delivery.

C. Results

The following reflects experiments targeted to define i) the effect of the IM versus IA loperamide and morphine in blocking the compression evoked change in blood pressure in the inflamed knee joint, and ii) the supraspinal effects.

1. Effects upon Resting and Compression Evoked Blood Pressure

The IA administration of morphine [3 mg], and loperamide [0.3 mg] had no effect upon resting blood pressure. IA morphine and IA loperamide, however, resulted in a dose dependent blockage of the cuff-evoked increase in BP [Table below]. In contrast to the effects of IA injection, the injection of the same doses in the contralateral leg had minimal suppressive effect upon the compression evoked response. The effects of IA loperamide were reversed by pretreatment with naloxone. IA morphine is similarly reversed in this model [data not shown].

TABLE

Summary of effect of intro-articular (IA) and intramuscular (IM) loperamide or morphine on the resting blood pressure and the pressure change evoked by compression of the inflamed knee joint.

| | Resting BP (mm Hg) | | Compression evoked BP (ΔPost Drug/ |
|---|---|---|---|
| | Pre Drug | Post Drug | %ΔPre Drug) × 100* |
| IA Vehicle (control) | | | |
| Rat 1 | 121 | 113 | 110 |
| Rat 2 | 110 | 121 | 98 |
| Rat 3 | 109 | 109 | 89 |
| Rat 4 | 89 | 91 | 114 |
| x̄ ± SE | 107 ± 13 | 109 ± 13 | 103 ± 11 |

TABLE-continued

Summary of effect of intro-articular (IA) and intramuscular (IM) loperamide or morphine on the resting blood pressure and the pressure change evoked by compression of the inflamed knee joint.

| | Resting BP (mm Hg) | | Compression evoked BP (ΔPost Drug/ |
|---|---|---|---|
| | Pre Drug | Post Drug | %ΔPre Drug) × 100* |
| IA Morphine† | | | |
| Rat 5 | 86 | 91 | 3 |
| Rat 6 | 112 | 102 | 12 |
| Rat 7 | 92 | 105 | 15 |
| Rat 8 | 86 | 92 | 7 |
| $\bar{x} \pm$ SE | 94 ± 12 | 98 ± 7 | 9 ± 5 |
| IA Loperamide† | | | |
| Rat 9 | 69 | 73 | 18 |
| Rat 10 | 103 | 109 | 21 |
| Rat 11 | 115 | 109 | 26 |
| Rat 12 | 102 | 115 | 29 |
| $\bar{x} \pm$ SE | 97 ± 19 | 102 ± 19 | 24 ± 5 |
| IM Morphine† | | | |
| Rat 13 | 115 | 119 | 63 |
| Rat 14 | 93 | 103 | 79 |
| Rat 15 | 89 | 111 | 58 |
| Rat 16 | 101 | 89 | 67 |
| $\bar{x} \pm$ SE | 100 ± 11 | 106 ± 13 | 67 ± 9 |
| IM Loperamide†† | | | |
| Rat 17 | 112 | 119 | 110 |
| Rat 18 | 128 | 106 | 101 |
| Rat 19 | 121 | 112 | 89 |
| Rat 20 | 105 | 100 | 91 |
| $\bar{x} \pm$ SE | 117 ± 10 | 109 ± 8 | 98 ± 10 |
| IA Loperamide + Naloxone††† | | | |
| Rat 21 | 89 | 110 | 115 |
| Rat 22 | 93 | 121 | 121 |
| Rat 23 | 119 | 123 | 118 |
| Rat 24 | 107 | 110 | 92 |
| $\bar{x} \pm$ SE | 102 ± 14 | 116 ± 7 | 112 ± 13 |

*%ΔPost Drug: Percent change in blood pressure evoked by knee joint compression [(Post knee joint compression − pre knee joint precompression) × 100] measured after delivery
% ΔPre Drug: Percent change in blood pressure evoked by knee joint compression before drug delivery [(Post knee joint compression − pre knee joint compression) × 100] measured before drug delivery.
†3 mg
††0.3 mg
†††(1 mg/kg, IP)

2. Side Effects of IM Loperamide and Morphine

Separate groups of unanesthetized rats were injected with IM morphine [3 mg] and/or loperamide [0.5 mg]. The time the animal would stand poised in front of a 4 cm high bar was measured and defined as catalepsy. As shown in the Table below, morphine, but not loperamide treated rats, were significantly more cataleptic. Loperamide animals showed no sign of catalepsy.

TABLE

Incidence of catalepsy after IM Loperamide and Morphine

| | Time to Dismount from Bar (sec) | |
|---|---|---|
| | Before Drug | After Drug Treatment (15 min) |
| IM Morphine (3 mg) | | |
| Rat A | 1 | 29 |
| Rat B | 2 | 52 |
| Rat C | 1 | 37 |
| Rat D | 1 | 31 |
| $\bar{x} \pm$ SE | 1 ± 1 | 37 ± 11 |
| IM Loperamide (0.5 mg) | | |
| Rat E | 1 | 1 |
| Rat F | 1 | 1 |
| Rat G | 1 | 3 |
| Rat H | 1 | 2 |
| $\bar{x} \pm$ SE | 1 ± 0 | 2 ± 1 |

D. Conclusions

These data indicate the following:

i) Loperamide and morphine given into the inflamed knee joint will reduce the pain response evoked by knee joint compression.

ii) The effects are mediated by a local action as the same injection into the contralateral leg had no effect [e.g., the effects were not mediated by drug levels that were achieved by parenteral delivery].

iii) The effects of loperamide even at the maximal systemic concentration [achieved by the IM injection in the unanesthetized rat] was without effects on centrally mediated behavior [catalepsy].

iv) The effects of loperamide at this dose were reversed by the opiate receptor antagonist naloxone suggesting that loperamide was acting via an opiate receptor.

EXAMPLE 3

Preparation of Petrolatum Based Water-washable Ointment

A petrolatum based water-washable ointment is prepared by melting inert ingredients together, adding loperamide hydrochloride and mixing well until the resulting ointment congeals.

| | Weight (%) |
|---|---|
| Loperamide hydrochloride | 0.5 |
| Lanolin alcohol | 0.1 |
| Emulsifying wax NF | 7.5 |
| Peg-20 corn glycerides | 5.0 |
| Petrolatum | 86.0 |

EXAMPLE 4

Preparation of Oil-in-water Creams

A. An oil-in-water cream is prepared from components (1) by heating water, propylene glycol, and Tween 20 [polysorbate 20] to 70–80° C., and then dissolving methylparaben and loperamide hydrochloride. The ingredients in (2) are then melted together at 70–80° C., and mixture (1) is added to mixture (2). The resulting composition is mixed until the cream congeals.

|  | Weight (%) |
| --- | --- |
| (1) | |
| Loperamide hydrochloride | 1.75 |
| Propylene glycol | 38.5 |
| Methyl paraben | 0.30 |
| Tween 20 (Polysorbate) | 3.50 |
| Water | 29.95 |
| (2) | |
| White petrolatum | 18.20 |
| Stearyl alcohol | 5.00 |
| Isopropyl myristate | 2.50 |
| Liposorb S (sorbitan stearate) | 1.20 |
| Liposorb S 20 (polysorbate 60) | 3.10 |

B. Alternatively, oil-in-water creams are prepared by heating water, propylene glycol and polyethylene glycol 400 to 70–80° C. and adding a mixture of white petrolatum, stearyl alcohol and surfactant [also mixed at 70–80° C.]. Then loperamide hydrochloride in benzyl alcohol is added and finally hydroxyethyl cellulose [optional] is added and the pH is adjusted to 7.5 with an appropriate buffer.

|  | Weight % |
| --- | --- |
| (1) | |
| Loperamide hydrochloride | 5.0 |
| Benzyl alcohol | 2.0 |
| Propylene glycol | 5.0 |
| Polyethylene glycol 400 | 5.0 |
| White Petrolatum | 10.0 |
| Stearyl alcohol | 5.0 |
| Hydroxyethyl cellulose | — |
| Surfactant* | 5.0 |
| Water | qs 100 |
| Buffer to pH | 7.5 |
| (2) | |
| Loperamide hydrochloride | 5.0 |
| Benzyl alcohol | 2.0 |
| Propylene glycol | 5.0 |
| Polyethylene glycol 400 | 5.0 |
| White Petrolatum | 10.0 |
| Stearyl alcohol | 5.0 |
| Hydroxyethyl cellulose | — |
| Surfactant* | 5.0 |
| Water | qs 100 |
| Buffer to adjust pH | 7.5 |

*Surfactant may be selected from, but not limited to, the following three systems: Steareth 2 plus steareth 21, or sorbitan monooleate plus polyoxyl 40 stearate, or poloxamer.

EXAMPLE 5
Prepararation of Water Washable Gels

A water-washable gel is prepared by adding Transcutol [diethylene glycol monoethyl ether] to propylene glycol, then dissolving the parabens and loperamide hydrochloride. Then water and Natrosol are added and mixed well until the mixture gels.

|  | Weight % |
| --- | --- |
| Loperamide hydrochloride | 4.00 |
| Propylene glycol | 55.00 |
| Transcutol (diethylene glycol monoethyl ether) | 5.00 |
| Natrosol 250 HHX (hydroxyethyl cellulose) | 2.00 |
| Methyl paraben | 0.18 |
| Propyl paraben | 0.02 |
| Water | 33.80 |

EXAMPLE 6
Preparation of Aqueous Gels

Aqueous gels are prepared by mixing loperamide hydrochloride, benzyl alcohol [and optionally propylene glycol and polyethylene glycol 400 as indicated in the ingredients list], adding to buffered water, and then adding hydroxyethyl cellulose with stirring until the mixture gels.

|  | Weight % |
| --- | --- |
| A. | |
| Loperamide hydrochloride | 5.0 |
| Benzyl alcohol | 2.0 |
| Propylene glycol | — |
| Polyethylene glycol 400 | — |
| Hydroxyethyl cellulose | 1.5 |
| Water | qs 100 |
| Buffer to pH | 6.5 |
| B. | |
| Loperamide hydrochloride | 5.0 |
| Benzyl alcohol | 2.0 |
| Propylene glycol | — |
| Polyethylene glycol 400 | — |
| Hydroxyethyl cellulose | 1.5 |
| Water | qs 100 |
| Buffer to pH | 7.5 |
| C. | |
| Loperamide hydrochloride | 5.0 |
| Benzyl alcohol | 2.0 |
| Propylene glycol | — |
| Polyethylene glycol 400 | — |
| Hydroxyethyl cellulose | 1.5 |
| Water | qs 100 |
| Buffer to pH | 8.5 |
| D. | |
| Loperamide hydrochloride | 5.0 |
| Benzyl alcohol | 2.0 |
| Propylene glycol | 5.0 |
| Polyethylene glycol 400 | — |
| Hydroxyethyl cellulose | 1.5 |
| Water | qs 100 |
| Buffer to pH | 7.5 |
| E. | |
| Loperamide hydrochloride | 5.0 |
| Benzyl alcohol | 2.0 |
| Propylene glycol | 5.0 |
| Polyethylene glycol 400 | 5.0 |
| Hydroxyethyl cellulose | 1.5 |
| Water | qs 100 |
| Buffer to pH | 7.5 |

EXAMPLE 7
Preparation of Polyethylene Glycol Water-washable Ointments

Polyethylene glycol water-washable ointments are prepared by mixing loperamide hydrochloride in benzyl alcohol and propylene glycol, adding polyethylene glycol 400 and 3350 and adjusting to pH 7.5 with buffer.

Example 7A

|  | Weight % |
|---|---|
| Loperamide hydrochloride | 5.0 |
| Benzyl alcohol | 5.0 |
| Propylene glycol | 5.0 |
| Polyethylene glycol 3350 | 40.0 |
| Polyethylene glycol 400 | qs 100 |
| Buffer to pH | 7.5 |

Example 7B

|  | Weight % |
|---|---|
| Loperamide hydrochloride | 2.5 |
| Benzyl alcohol | 5.0 |
| Propylene glycol | 5.0 |
| Polyethylene glycol 3350 | 40.0 |
| Polyethylene glycol 400 | qs 100 |
| Buffer to pH | 7.5 |

Example 7C

|  | Weight % |
|---|---|
| Loperamide hydrochloride | 1.0 |
| Benzyl alcohol | 5.0 |
| Propylene glycol | 5.0 |
| Polyethylene glycol 3350 | 40.0 |
| Polyethylene glycol 400 | qs 100 |
| Buffer to pH | 7.5 |

Example 7D

| INGREDIENTS | 7D1 | 7D2 | 7D3 | 7D4 | 7D5 |
|---|---|---|---|---|---|
| White Petroleum, USP | — | — | — | 85.00 | 86.00 |
| Mineral Oil, USP | — | — | — | 10.00 | — |
| Benzyl Alcohol, NF | 10.00 | 5.00 | 2.00 | — | 3.00 |
| Propylene Glycol, USP | 20.00 | 15.00 | 15.00 | — | 5.00 |
| PEG 400, NF | 35.00 | 47.50 | 52.00 | — | — |
| PEG 3350, USP | 30.00 | 30.00 | 30.00 | — | — |
| Loperamide hydrochloride (Micronized) | — | — | — | 5.00 | — |
| Loperamide hydrochloride (non-micronized) | 5.00 | 2.5 | 1.0 | — | 1.00 |
| Glycerol Monostearate, NF | — | — | — | — | 5.00 |

Example 7E

| INGREDIENTS | 7E1 | 7E2 | 7E3 | 7E4 |
|---|---|---|---|---|
| Petrolatum, USP | 86.00 | 18.20 | 30.75 | — |
| Stearyl Alcohol, USP | — | 5.00 | 9.25 | — |
| Isopropyl Myristate | — | 2.50 | 4.00 | — |
| Sorbitan Stearate | — | 1.20 | — | — |
| Polysorbate 60 | — | 3.10 | — | — |
| Liposorb L | — | — | 10.20 | — |
| Tween 20 | — | — | 1.80 | — |
| Distilled Water | — | 25.80 | 14.60 | 33.80 |
| Propylparaben, USP | — | — | — | 0.02 |
| Natrosol 250 HHX | — | — | — | 2.00 |
| Transcutol | — | — | 15.00 | 5.00 |
| Propylene Glycol, USP | — | 38.50 | 12.50 | 55.00 |
| Methylparaben, USP | — | 0.30 | 0.30 | 0.18 |
| Polysorbate 20 | — | 3.50 | — | — |
| Lanolin Alcohol, USP | 1.00 | — | — | — |
| Emulsifying Wax, NF | 7.50 | — | — | — |
| PEG 20 Corn Glycerides | 5.00 | — | — | — |
| Loperamide hydrochloride (Non-Micronized) | — | 1.75 | 1.50 | 4.00 |
| Loperamide hydrochloride (Micronized) | 0.50 | — | — | — |
| Triethanolamine | — | 0.15 | 0.10 | — |

Example 7F

| INGREDIENTS | 7F1 | 7F2 | 7F3 | 7F4 | 7F5 | 7F6 | 7F7 |
|---|---|---|---|---|---|---|---|
| Stearyl Alcohol, NF | 5.00 | 5.00 | 5.00 | 5.00 | 5.00 | 5.00 | 5.00 |
| White Petrolatum, USP | 10.00 | 10.00 | 10.00 | 10.00 | 10.00 | 10.00 | 10.00 |
| Polyoxyethylene 21 Stearyl Ether | 1.00 | 1.00 | 1.00 | 1.00 | 1.00 | 1.00 | 1.00 |
| Polyoxyethylene 2 Stearyl Ether | 1.20 | 1.20 | 1.20 | 1.20 | 1.20 | 1.20 | 1.20 |
| Purified Water, Part I USP | 54.75 | 54.60 | 54.60 | 64.80 | 69.30 | 68.80 | 67.30 |
| Sodium Phosphate Monobasic, USP | 0.85 | 0.36 | 0.50 | — | — | — | — |
| Sodium Phosphate Dibasic, ACS | 0.20 | 0.74 | — | — | — | — | — |
| Sodium Phosphate Tribasic, ACS | — | — | 0.60 | — | — | — | — |
| Propylene Glycol, USP | 5.00 | 5.00 | 5.00 | 5.00 | 5.00 | 5.00 | 5.00 |
| Benzyl Alcohol, NF | 2.00 | 2.00 | 2.00 | 2.00 | 2.00 | 2.00 | 2.00 |
| Hydroxyethyl Cellulose 250 HHX | 1.00 | 1.00 | 1.00 | 1.00 | 1.00 | 1.00 | 1.00 |
| Polyethylene Glycol 400, NF | 5.00 | 5.00 | 5.00 | 5.00 | 5.00 | 5.00 | 5.00 |
| Loperamide hydrochloride (Micronized) | 5.00 | 5.00 | 5.00 | 5.00 | 0.50 | 1.00 | 2.50 |
| Purified Water II USP | 5.00 | 5.00 | 5.00 | — | — | — | — |
| Sodium Hydroxide, 10% Solution, NF | 4.00 | 4.10 | 4.10 | — | — | — | — |
| pH | ~6 | ~7 | ~8 | — | — | — | — |

Example 7G

| INGREDIENTS | 7G1 | 7G2 | 7G3 | 7G4 | 7G5 | 7G6 |
|---|---|---|---|---|---|---|
| Stearyl Alcohol, NF | 5.00 | 5.00 | — | 5.00 | 5.00 | — |
| White Petrolatum, USP | 10.00 | 10.00 | — | 10.00 | 10.00 | — |
| Polyoxyethylene 21 Stearyl Ether | 1.00 | 1.00 | — | 1.00 | 1.00 | — |
| Polyoxyethylene 2 Stearyl Ether | 1.20 | 1.20 | — | 1.20 | 1.20 | — |
| Purified Water, Part I USP | 54.60 | 60.55 | 38.00 | 51.20 | 44.70 | 36.95 |
| Sodium Phosphate Monobasic, USP | 0.50 | 0.50 | — | — | 0.50 | 0.85 |
| Sodium Phosphate Dibasic, USP | — | — | — | — | — | 0.20 |
| Sodium Phosphate Tribasic, USP | 0.60 | 0.60 | — | — | 0.60 | — |
| Borax | — | — | — | 0.50 | — | — |
| 0.1 M HCl | — | — | — | 4.00 | — | — |
| Propylene Glycol, USP | 5.00 | 5.00 | 45.00 | 5.00 | 5.00 | 45.00 |
| Benzyl Alcohol, NF | 2.00 | 2.00 | 10.00 | 2.00 | 2.00 | 10.00 |
| Hydroxyethyl Cellulose 250 HHX | 1.00 | 1.00 | 2.00 | 1.00 | 0.50 | 2.00 |
| Transcutol | — | — | — | — | 10.00 | — |
| Polyethylene Glycol 400, NF | 5.00 | 5.00 | — | 5.00 | 5.00 | — |
| Loperamide hydrochloride (Micronized) | 5.00 | 1.75 | — | 5.00 | 5.00 | — |
| Loperamide hydrochloride (Non-Micronized) | — | — | 5.00 | — | — | 5.00 |
| Purified Water, Part II USP | 5.00 | 5.00 | — | 5.00 | 5.50 | — |
| Sodium Hydroxide, 10% Solution, NF | 4.10 | 1.40 | — | 4.10 | 4.00 | — |
| pH (neat) | 8.20 | 8.13 | 4.33 | 9.27 | 7.98 | 6.02 |

Example 7H

| INGREDIENTS | 7H1 | 7H2 | 7H3 |
|---|---|---|---|
| Loperamide hydrochloride (Non-Micronized) | 1.75 | 3.00 | 1.75 |
| Propylene Glycol, USP | 38.50 | 38.50 | 38.50 |
| Methylparaben, NF | 0.30 | 0.30 | 0.30 |
| Polysorbate 20 | 3.50 | 3.50 | 3.50 |
| Purified Water | 25.80 | 24.55 | 15.00 |
| Petrolatum, USP | 18.20 | 18.20 | 18.20 |
| Stearyl Alcohol, NF | 5.00 | 5.00 | 5.00 |
| Isopropyl Myristate | 2.50 | 2.50 | 2.50 |
| Sorbitan Stearate | 1.20 | 1.20 | 1.20 |
| Polysorbate 60 | 3.10 | 3.10 | 3.10 |
| Purified Water | — | — | 6.85 |
| Sodium Phosphate Monobasic, ACS | — | — | 0.50 |
| Sodium Phosphate Tribasic, ACS | — | — | 0.60 |
| Triethanolamine 50% | 0.15 | 0.15 | — |
| Triethanolamine | — | — | 3.00 |
| pH(neat) | 5.45 | 5.45 | 8.10 |

Example 7I

| INGREDIENTS | 7I1 | 7I2 | 7I3 | 7I4 | 7I5 |
|---|---|---|---|---|---|
| Stearyl Alcohol, NF | — | 5.00 | 5.00 | 5.00 | 5.00 |
| White Petrolatum, USP | — | 10.00 | 10.00 | 10.00 | 10.00 |
| Polyoxyethylene 21 Stearyl Ether | — | 1.00 | 1.00 | 1.00 | 1.00 |
| Polyoxyethylene 2 Stearyl Ether | — | 1.20 | 1.20 | 1.20 | 1.20 |
| Purified Water, Part I USP | 38.50 | 66.80 | 65.00 | 59.60 | 59.50 |
| Sodium Phosphate Monobasic, USP | — | 0.50 | 0.50 | 0.50 | 0.20 |
| Sodium Phosphate Dibasic, USP | — | — | — | — | 0.90 |
| Sodium Phosphate Tribasic, USP | — | 0.60 | 0.60 | 0.60 | — |
| Propylene Glycol, USP | 45.00 | 5.00 | 5.00 | 5.00 | 5.00 |
| Benzyl Alcohol, NF | 10.00 | 2.00 | 2.00 | 2.00 | 2.00 |
| Hydroxyethyl Cellulose 250 HHX | 2.00 | 1.00 | 1.00 | 1.00 | 1.00 |
| Polyethylene Glycol 400, NF | — | 5.00 | 5.00 | 5.00 | 5.00 |
| Loperamide hydrochloride (Micronized) | — | 1.00 | 2.00 | 5.00 | 5.00 |
| Loperamide hydrochloride (Non-Micronized) | 4.5 | — | — | — | — |
| Sodium Hydroxide, 10% Solution, NF | — | 0.90 | 1.70 | 4.10 | 4.20 |
| pH (neat) | 4.16 | 8.55 | 8.53 | 8.69 | 7.45 |

Example 7J

| INGREDIENTS | 7J1 | 7J2 | 7J3 | 7J4 | 7J5 |
|---|---|---|---|---|---|
| Glyceryl Monostearate, NF | — | — | 5.0 | — | — |
| Stearyl Alcohol, NF | 5.0 | 5.0 | — | 5.0 | 5.0 |
| White Petrolatum, USP | 10.0 | 10.0 | 85.0 | 10.0 | 10.0 |
| Polyoxyethylene 21 Stearyl Ether (HLB ~ 15) | 1.0 | 1.0 | — | 1.0 | 1.0 |
| Polyoxyethylene 2 Stearyl Ether (HLB ~ 5) | 1.2 | 1.2 | — | 1.2 | 1.2 |
| Purified Water, USP | 59.56 | 59.2 | — | 68.12 | 64.2 |
| Sodium Phosphate Monobasic, NF | — | 0.2 | — | 0.2 | 0.2 |
| Sodium Phosphate Dibasic (Anhydrous), USP | 0.5 | 1.3 | — | 1.3 | 1.3 |
| Sodium Phosphate Tribasic, USP | 0.64 | — | — | — | — |
| Propylene Glycol, USP | 5.0 | 5.0 | 5.0 | 5.0 | 1.0 |
| 10% Sodium Hydroxide, NF | 4.1 | 4.1 | — | 0.16 | 4.1 |
| Polyethylene Glycol 400, NF | 5.0 | 5.0 | — | 5.0 | 5.0 |
| Hydroxyethyl Cellulose 250 HHX, NF | 1.0 | 1.0 | — | 1.0 | 1.0 |
| Benzyl Alcohol, NF | 2.0 | 2.0 | 3.0 | 2.0 | 1.0 |
| Loperamide hydrochloride (Micronized) | 5.0 | 5.0 | 2.0 | 0.2 | 5.0 |
| pH | 8.42 | 7.70 | — | 7.54 | 7.58 |

Example 7K

| INGREDIENTS | 7K1 | 7K2 | 7K3 | 7K4 | 7K5 | 7K6 |
|---|---|---|---|---|---|---|
| Stearyl Alcohol, NF | 5.00 | 5.00 | 5.00 | 5.00 | 5.00 | 5.00 |
| White Petrolatum, USP | 10.00 | 10.00 | 10.00 | 10.00 | 10.00 | 10.00 |
| Polyoxyethylene 21 | 1.00 | 1.00 | 1.00 | 1.00 | 1.00 | 1.00 |

-continued

| IN-GREDIENTS | 7K1 | 7K2 | 7K3 | 7K4 | 7K5 | 7K6 |
|---|---|---|---|---|---|---|
| Stearyl Ether Polyoxyethylene 2 Stearyl Ether | 1.20 | 1.20 | 1.20 | 1.20 | 1.20 | 1.20 |
| Sodium Phosphate Monobasic, USP | 0.20 | 0.20 | 0.20 | 0.20 | 0.20 | 0.20 |
| Sodium Phosphate Dibasic, USP | 1.30 | 1.30 | 1.30 | 1.30 | 1.30 | 1.30 |
| Sodium Hydroxide, NF, 10% Solution | * | * | 0.16 | * | 4.10 | * |
| Propylene Glycol, USP | 1.00 | 1.00 | 1.00 | 1.00 | 1.00 | 1.00 |
| Benzyl Alcohol, NF | 1.00 | 1.00 | 1.00 | 1.00 | 1.00 | 1.00 |
| Hydroxyethyl Cellulose 250 HHX | 1.00 | 1.00 | 1.00 | 1.00 | 1.00 | 1.00 |
| Polyethylene Glycol 400, NF | 5.00 | 5.00 | 5.00 | 5.00 | 5.00 | 5.00 |
| Loperamide hydrochloride (Micronized) | 0.008 | 0.04 | 0.20 | 1.00 | 5.00 | 20.00 |
| Purified Water, USP | ** | ** | 72.94 | ** | 64.20 | ** |
| Hydrochloric Acid, NF, 3M | — | — | — | — | — | — |
| TOTAL | 100.0 | 100.0 | 100.0 | 100.0 | 100.0 | 100.0 |

*Sodium hydroxide was added as required to adjust pH to 7.5.
**Purified water, USP, was added as required to bring total to 100.0%.

Example 7L

| INGREDIENTS | 7L1 | 7L2 | 7L3 | 7L4 | 7L5 | 7L6 | 7L7 |
|---|---|---|---|---|---|---|---|
| Glyceryl Monostearate, NF | — | — | — | — | — | 5.0 | — |
| Stearyl Alcohol, USP | — | 5.0 | 5.0 | 5.0 | 5.0 | — | 5.0 |
| White Petrolatum, USP | — | 10.0 | 10.0 | 10.0 | 10.0 | 87.0 | 10.0 |
| Polyoxyethylene 21 Stearyl Ether (HLB ~15) | — | 1.0 | 1.0 | 1.0 | 1.0 | — | 1.0 |
| Polyoxyethylene 2 Stearyl Ether (HLB ~5) | — | 1.2 | 1.2 | 1.2 | 1.2 | — | 1.2 |
| Purified Water, USP | 40.0 | 59.85 | 60.66 | 60.80 | 60.50 | — | 65.50 |
| Sodium Phosphate Monobasic, USP | — | 0.5 | 0.5 | 0.5 | 0.2 | — | 0.2 |
| Sodium Phosphate Dibasic (Anhydrous), USP | — | — | — | — | 1.3 | — | 1.3 |
| Sodium Phosphate Tribasic, USP | — | 0.65 | 0.64 | 0.6 | — | — | — |
| Propylene Glycol, USP | 46.80 | 5.0 | 5.0 | 5.0 | 5.0 | 5.0 | 1.0 |
| 10% Sodium Hydroxide, NF | — | 4.7 | 4.3 | 4.1 | 4.1 | — | 4.1 |
| Polyethylene Glycol 400, NF | — | 5.0 | 5.0 | 5.0 | 5.0 | — | 5.0 |
| 3M Hydrochloric Acid | — | 4.1 | 3.8 | 3.8 | 3.7 | — | 3.7 |
| 0.05 M Hydrochloric Acid | 0.7 | — | — | — | — | — | — |
| Hydroxyethyl Cellulose 250 HHX, NF | 2.1 | 1.0 | 1.0 | 1.0 | 1.0 | — | 1.0 |
| Benzyl Alcohol, NF | 10.4 | 2.0 | 2.0 | 2.0 | 2.0 | 3.0 | 1.0 |
| pH | 4.24 | 8.98 | 8.54 | 7.96 | 7.65 | — | 7.59 |

Example 7M

This example is directed to the preparation of the compositions described in Examples 7J5 and 7L.

i. Into a vessel were weighed purified water, sodium phosphate monobasic and sodium phosphate dibasic. To this mixture were added propylene glycol and sodium hydroxide. The resulting mixture was mixed with a high speed propeller mixer until a clear solution was obtained. With continuous mixing, hydroxyethyl cellulose was added. Mixing was continued until a gel was formed.

ii. Into a separate vessel were weighed stearyl alcohol, white petrolatum and polyoxyethylene stearyl ether. The mixtures from Steps i and ii were each heated to approximately 70° C.

iii. While mixing, the mixture from Step ii was added to the mixture from Step A. The resulting mixture was homogenized for approximately 10 minutes. With continuous mixing, benzyl alcohol was added, and the resulting mixture was homogenized for approximately 5 minutes.

iv. Into a separate container was weighed polyethylene glycol 400 and loperamide. This mixture was mixed until a smooth paste was achieved. With continuous mixing using a Silverson mixer, the mixture rom Step iii was added to the loperamide/PEG mixture. The resulting mixture was mixed for approximately 10 minutes. Water bath cooling, during which time Silverson mixing and side scraping were performed, provided the compositions of Examples 7J5 and 7L.

EXAMPLE 8

Yeast-Induced Inflammation

A Randall-Selitto assay [see, Randall et al. (1957) *Arch. Int. Pharmacodyn.* 111:409–419] was performed to determine the effect of loperamide upon the pain threshold of the yeast-injected left hind paw of male Sprague-Dawley rats.

Each rat was injected with 100 $\mu$l of a 20% yeast solution into the plantar surface of the left hind paw. Four hours later loperamide was administered at 10, 50 or 250 $\mu$g/100 $\mu$l/rat in a vehicle of 10% DMSO [n=10/dose group]. Control rats were treated with 10% DMSO alone [n=20]. The pain thresholds of the inflamed and non-inflamed paws were measured by application of a pressure stimulus to the paw and the paw pressure threshold in gram [g] was recorded.

As shown in the following table, loperamide produced a dose-dependent increase in the paw pressure threshold.

| Dose, μg | Paw Pressure Threshold, g |
|---|---|
| 10 | 66 ± 15 |
| 50 | 124 ± 29 |
| 250 | 153 ± 25 |

EXAMPLE 9

This example includes a description of experiments which were conducted to measure the in vitro penetration of the five compositions prepared in Example 7J in "stripped" and intact human cadaver skin. The study determined cumulative penetration over 24 hrs and skin tissue distribution at 24 hrs.

| Example No.* | Loperamide Concentration (%) | Composition Description | Skin Type |
|---|---|---|---|
| 7J4 (5) | 0.2 | Cream | Intact |
| 7J4 (5) | 0.2 | Cream | Stripped |
| 7J5 (5) | 5.0 | Cream | Intact |
| 7J5 (5) | 5.0 | Cream | Stripped |
| 7J1 (6) | 5.0 | Cream | Intact |
| 7J1 (6) | 5.0 | Cream | Stripped |
| 7J1 (6) | 5.0 | Cream | Intact |
| 7J2 (6) | 5.0 | Cream | Stripped |
| 7J3 (5) | 2.0 | Pet. Ointment | Intact |
| 7J3 (5) | 2.0 | Pet. Ointment | Stripped |

*Number of replicates in parentheses.

$^{14}$C-Loperamide (s.a. 13.20 mCi/mmol) was provided by New England Nuclear (Billerica, Mass.).

Compositions were spiked with $^{14}$C-loperamide and mixed thoroughly with a spatula. Compositions were prepared and spiked immediately prior to application to the skin chamber. Compositions were tested for uniform specific activity by liquid scintillation counting.

Set Up

Franz static diffusion chambers were filled with a 4% BSA isotonic buffered saline solution (6–10 mL reservoir volume) and equilibrated to a temperature of 37° C. by a circulating water pump. Excised human cadaver skin (approximately 200 micron split thickness) was placed onto each chamber. The skin surface area for each chamber was approximately 1.77 cm$^2$. Five or six replicates were run for each group, as indicated in the Table above. Skin from a single human donor was used for the study.

Design of Experiment

Samples were obtained for cumulative penetration at 0, 1, 3, 6, and 24 hours. Tissue recovery was measured at 24 hours.

Composition Application

A Gilson Microman positive displacement pipet was used to apply 30 mg (16.9 mg/cm$^2$) of test formulation to each chamber.

Time Points

Samples of 1.0 mL were taken with a Gilson Pipetman at time points of 0, 1, 3, 6 and 24 hours. The samples were placed in a vial containing Ecoscint scintillation fluor. At each time point, the 1.0 mL volume was replaced with the BSA saline solution.

Washes and Gauze Swipes

To recover excess formulation from the skin surface, the skin was first washed with three 1.0 mL volumes of 2% Oleth-20 in water and retained for counting. The skin was then gently wiped with 3 separate cotton gauzes which were saved and counted.

Skin Compartment Determinations

The skin removed from the chamber was tape-stripped with cellophane tape until "glistening" (approximately 22 strips). The first two strips that removed the excess loperamide adhering to the outer surface of the stratum corneum were counted separately. These counts were included in total recovery, but excluded from stratum corneum compartment recovery. Four groups each consisting of five consecutive tape strips were placed in a scintillation vial containing Scintilene. Dermis and epidermis were separated by microwave technique and placed in vials containing ReadyProt cocktail for tissue digestion. All sample were counted in a Beckman LSC counter and corrected for quenching. Recovery in the reservoir, washes, gauze wipes, and the respective skin compartments was calculated by determining the percentage of the total scintillation counts (SC) applied that were recovered. The microgram recovery was calculated based on the specific activity (SA) of each test composition. The mean % of microgram recovery was calculated, discarding those values in each group that exceeded the mean±three standard deviations.

The overall effectiveness of the test formulations is summarized in Tables A–D, which show: the percent (Tables A and B) and micrograms (μg) (Tables C and D); combined recovery in the reservoir, dermis and epidermis (Tables A and C); and reservoir, dermis, epidermis and stratum corneum (Tables B and D). The cumulative penetration into the lower reservoir is presented as percent (Table E) and micrograms (μg) (Table F).

TABLE A

| Relative Effectiveness | Composition Example No. (Skin type) | Composition Description | Loperamide Concentration (%) | Total SC (Reservoir, Epidermis and Dermis) (%) |
|---|---|---|---|---|
| 1 | 7J3 (Stripped) | Ointment | 2.0 | 9.4 |
| 2 | 7J4 (Stripped) | Cream | 0.2 | 5.8 |
| 3 | 7J1 (Stripped) | Cream | 5.0 | 5.5 |
| 4 | 7J4 (Intact) | Cream | 0.2 | 4.4 |
| 5 | 7J2 (Stripped) | Cream | 5.0 | 4.3 |
| 6 | 7J5 (Stripped) | Cream | 5.0 | 3.6 |
| 7 | 7J5 (Intact) | Cream | 5.0 | 3.4 |
| 8 | 7J3 (Intact) | Ointment | 2.0 | 3.2 |
| 9 | 7J1 (Intact) | Cream | 5.0 | 3.0 |
| 10 | 7J2 (Intact) | Cream | 5.0 | 2.3 |

TABLE B

| Relative Effectiveness | Example No. (Skin type) | Composition Description | Loperamide Concentration (%) | Total SC (Reservoir, Epidermis, Dermis and Stratum Corneum) (%) |
|---|---|---|---|---|
| 1 | 7J3 (Stripped) | Ointment | 2.0 | 9.4 |
| 2 | 7J4 (Intact) | Cream | 0.2 | 5.9 |
| 3 | 7J4 (Stripped) | Cream | 0.2 | 5.8 |
| 4 | 7J1 (Stripped) | Cream | 5.0 | 5.5 |
| 5 | 7J3 (Intact) | Ointment | 2.0 | 4.7 |
| 6 | 7J2 (Stripped) | Cream | 5.0 | 4.3 |
| 7 | 7J5 (Intact) | Cream | 5.0 | 4.1 |

TABLE B-continued

| Relative Effectiveness | Example No. (Skin type) | Composition Description | Loperamide Concentration (%) | Total SC (Reservoir, Epidermis, Dermis and Stratum Corneum) (%) |
|---|---|---|---|---|
| 8 | 7J5 (Stripped) | Cream | 5.0 | 3.6 |
| 9 | 7J1 (Intact) | Cream | 5.0 | 3.6 |
| 10 | 7J2 (Intact) | Cream | 5.0 | 2.7 |

TABLE C

| Relative Effectiveness | Example No. (Skin type) | Composition Description | Loperamide Concentration (%) | Total 5C (Reservoir, Epidermis and Dermis) (Micrograms) |
|---|---|---|---|---|
| 1 | 7J1 Stripped | Cream | 5.0 | 82.8 |
| 2 | 7J2 Stripped | Cream | 5.0 | 65.2 |
| 3 | 7J3 Stripped | Ointment | 2.0 | 56.5 |
| 4 | 7J5 Stripped | Cream | 5.0 | 54.7 |
| 5 | 7J5 Intact | Cream | 5.0 | 50.6 |
| 6 | 7J1 Intact | Cream | 5.0 | 44.8 |
| 7 | 7J2 Intact | Cream | 5.0 | 33.8 |
| 8 | 7J3 Intact | Ointment | 2.0 | 19.3 |
| 9 | 7J4 Stripped | Cream | 0.2 | 3.5 |
| 10 | 7J4 Intact | Cream | 0.2 | 2.6 |

TABLE D

| Relative Effectiveness | Example No. (Skin type) | Composition Description | Loperamide Concentration (%) | Total SC (Reservoir, Epidermis, Dermis and Stratum Corneum) (μg) |
|---|---|---|---|---|
| 1 | 7J1 Stripped | Cream | 5.0 | 82.8 |
| 2 | 7J2 Stripped | Cream | 5.0 | 65.2 |
| 3 | 7J5 Intact | Cream | 5.0 | 61.7 |
| 4 | 7J3 Stripped | Ointment | 2.0 | 56.5 |
| 5 | 7J5 Stripped | Cream | 5.0 | 54.7 |
| 6 | 7J1 Intact | Cream | 5.0 | 53.5 |
| 7 | 7J2 Intact | Cream | 5.0 | 41.2 |
| 8 | 7J3 Intact | Ointment | 2.0 | 28.4 |
| 9 | 7J4 Intact | Cream | 0.2 | 3.5 |
| 10 | 7J4 Stripped | Cream | 0.2 | 3.5 |

TABLE E

| Composition Example No. (Skin type) | Time (hr) | | | | |
|---|---|---|---|---|---|
| | 0 | 1 | 3 | 6 | 24 |
| 7J4 (Intact) | 0.00 ± 0.00 | 0.22 ± 0.11 | 0.66 ± 0.31 | 0.85 ± 0.40 | 1.36 ± 0.61 |
| 7J4 (Stripped) | 0.00 ± 0.00 | 0.24 ± 0.21 | 0.71 ± 0.55 | 1.00 ± 0.70 | 1.90 ± 0.98 |
| 7J5 (Intact) | 0.00 ± 0.00 | 0.14 ± 0.10 | 0.42 ± 0.27 | 0.63 ± 0.44 | 1.10 ± 0.89 |
| 7J5 (Stripped) | 0.00 ± 0.00 | 0.31 ± 0.27 | 0.78 ± 0.56 | 1.04 ± 0.70 | 1.84 ± 1.17 |
| 7J1 (Intact) | 0.00 ± 0.00 | 0.15 ± 0.12 | 0.49 ± 0.33 | 0.69 ± 0.48 | 1.05 ± 0.64 |
| 7J1 (Stripped) | 0.00 ± 0.00 | 0.23 ± 0.14 | 0.90 ± 0.59 | 1.39 ± 0.98 | 2.63 ± 1.55 |
| 7J2 (Intact) | 0.00 ± 0.00 | 0.11 ± 0.06 | 0.29 ± 0.17 | 0.37 ± 0.21 | 0.69 ± 0.38 |
| 7J2 (Stripped) | 0.00 ± 0.00 | 0.33 ± 0.19 | 1.07 ± 0.89 | 1.65 ± 0.98 | 2.61 ± 1.10 |
| 7J3 (Intact) | 0.00 ± 0.00 | 0.01 ± 0.00 | 0.05 ± 0.03 | 0.12 ± 0.08 | 0.76 ± 0.42 |
| 7J3 (Stripped) | 0.00 ± 0.00 | 0.04 ± 0.01 | 0.26 ± 0.15 | 0.64 ± 0.33 | 3.18 ± 0.89 |

TABLE F

| Example No. (Skin type) | Time (hr) | | | | |
|---|---|---|---|---|---|
| | 0 | 1 | 3 | 6 | 24 |
| 7J4 (Intact) | 0.0 ± 0.0 | 0.1 ± 0.1 | 0.4 ± 0.2 | 0.5 ± 0.2 | 0.8 ± 0.4 |
| 7J4 (Stripped) | 0.0 ± 0.0 | 0.1 ± 0.1 | 0.4 ± 0.3 | 0.6 ± 0.4 | 1.1 ± 0.6 |
| 7J5 (Intact) | 0.0 ± 0.0 | 2.1 ± 1.5 | 6.3 ± 4.1 | 9.4 ± 6.6 | 16.5 ± 13.3 |
| 7J5 (Stripped) | 0.0 ± 0.0 | 4.7 ± 4.0 | 11.6 ± 8.3 | 15.6 ± 10.5 | 27.5 ± 17.5 |
| 7J1 (Intact) | 0.0 ± 0.0 | 2.2 ± 1.9 | 7.3 ± 5.0 | 10.3 ± 7.3 | 15.8 ± 9.6 |
| 7J1 (Stripped) | 0.0 ± 0.0 | 3.4 ± 2.1 | 13.4 ± 8.8 | 20.8 ± 14.7 | 39.5 ± 23.2 |
| 7J2 (Intact) | 0.0 ± 0.0 | 1.6 ± 0.8 | 4.3 ± 2.6 | 5.6 ± 3.2 | 10.4 ± 5.7 |
| 7J2 (Stripped) | 0.0 ± 0.0 | 5.0 ± 2.8 | 16.0 ± 13.3 | 24.7 ± 14.7 | 39.1 ± 16.5 |
| 7J3 (Intact) | 0.0 ± 0.0 | 0.0 ± 0.0 | 0.3 ± 0.2 | 0.7 ± 0.5 | 4.6 ± 2.5 |
| 7J3 (Stripped) | 0.0 ± 0.0 | 0.2 ± 0.1 | 1.5 ± 0.9 | 3.8 ± 2.0 | 19.1 ± 5.4 |

EXAMPLE 10

This example includes a description of in vitro studies that were conducted to evaluate the inhibition by loperamide and morphine of [$^3$H]diprenorphine binding to human mu ($\mu$) opiate receptors.

Membranes of CHO cells expressing human $\mu$ opiate receptors were incubated with [$^3$H]diprenorphine (1.0 nM) for 60 min at room temperature in the presence of increasing concentrations of agonist in 50 mM Tris-HCl, pH 7.8, containing protease inhibitors. After incubation, the mixtures were passed through GF/B filters that had been pretreated with polyethylenimine and bovine serum albumin. The filters were washed with cold Tris-HCl buffer and radioactivity was determined by scintillation spectroscopy.

Three experiments were conducted (n=3). As measured by displacement of specific [$^3$H]diprenorphine binding, loperamide has a high affinity for the human $\mu$ opiate receptor, (average $K_i$ is 3 nM); whereas, the average $K_i$ of morphine was 19 nM. Loperamide also has a lower affinity for both the human $\delta$ receptor (average $K_i$ of 48 nM) and the human $\kappa$ receptor (average $K_i$ of 1160 nM). Binding experiments with 15 nonopiate receptors confirmed that loperamide is highly selective for the $\mu$ opiate receptor. Results of one of the experiments involving the $\mu$ opitate receptor are set forth in FIG. 1.

EXAMPLE 11

Assessment of the Effect of Loperamide Administered into the Paw on Formalin-induced Nociception A. Model Administration of formalin into the paw results in a localized inflammation and in spontaneous flinching behavior. This response is indicative of pain. Flinching responses include paw lifting and paw shaking, and are characterized by a rapid vibration of the paw after drawing it under the body. The flinching response can be reliably quantitated and exhibits two peaks of activity which are indicative of acute and tonic pain. The early or acute phase lasts from 0–5 minutes post-formalin and is followed by a quiescent period lasting approximately 15 minutes. The tonic phase occurs form 20–35 minutes following formalin injection and is the interval where the number of flinching responses is maximal. This model has been characterized in several species and is sensitive to the analgesic effects of opiates administered by a variety of routes, including local administration directly into the paw.

B. Methods

1. Induction of Inflammation

Male Sprague-Dawley rats weighing 70–90 g were used. Inflammation was induced by subcutaneous injection of 50 $\mu$l of a 5% formalin solution into the dorsal surface of the right hind paw.

Flinching behavior was quantitated by counting the number of responses that occurred during the tonic phase of pain, lasting from 20–35 minutes after formalin injection. Results are expressed as the mean percent antagonism of formalin-induced flinching calculated for individual drug-treated, formalin-injected rats using the following formula:

(mean formalin response−mean saline response−individual response×100/mean formalin response−mean saline response in which the mean formalin response is the mean behavioral score of vehicle-treated and formalin-injected rats. The mean saline response is the pooled behavior score from rats injected with 50 $\mu$l of saline into the paw.

2. Drugs and Drug Delivery

Loperamide [Research Biochemicals Inc., Natick, Mass.] was administered at doses of 1, 3, 10, 30, 100 or 300 $\mu$g/50 $\mu$l of a 20% cremophor EF vehicle [BASF, Rahway, N.J.] to groups of rats [7–9 per dose group]. Injections of drug were given into the dorsal surface of the paw at 10 minutes prior to formalin injection, and were counterbalanced across treatment groups.

C. Results

As shown in the following table, when inflammation-induced tonic pain was produced by formalin injection into the paw, loperamide produced a dose-dependent antinociception, as measured by a decrease in flinching behaviors. At the highest dose of 300 $\mu$g, practically no flinching behavior was observed.

Summary of the effect of loperamide or formalin-induced inflammation

| Dose, $\mu$g | % Antagonism of Late Phase Flinching |
| --- | --- |
| 1 | 20 ± 7 |
| 3 | 53 ± 10 |
| 10 | 55 ± 15 |
| 30 | 74 ± 10 |
| 100 | 75 ± 11 |
| 300 | 97 ± 2 |

Data are the mean ± SEM

D. Conclusions

These data indicate the following:

1) Loperamide administered directly into the paw reduces the pain associated with formalin-induced inflammation.
2) The effect of loperamide is dose-dependent, with greater antinociception occurring at higher doses.

EXAMPLE 12

This example describes in vivo studies that were conducted to evaluate the antagonism by loperamide and morphine of late phase formalin-induced flinching.

Inflammation was induced in rats by subcutaneous injection of 50 $\mu$L of a 5% formalin solution into the dorsal surface of the right hind paw. Loperamide and morphine were injected s.c. into the dorsal surface of the right hind paw, hereinafter referred to as an intrapaw (i.paw) injection. Loperamide was administered at various doses in a 20% cremophor EL vehicle. Loperamide was injected i.paw at 10 min prior to formalin injection. Flinching behavior was quantitated by counting the number of flinching responses that occurred during the tonic phase of pain, lasting from 20 to 35 min, respectively, after formalin injection. Results are expressed graphically in FIG. 2 as the mean percent antagonism (% A) of formalin-induced flinching calculated for individually treated, formalin-injected rats.

Figure 2:
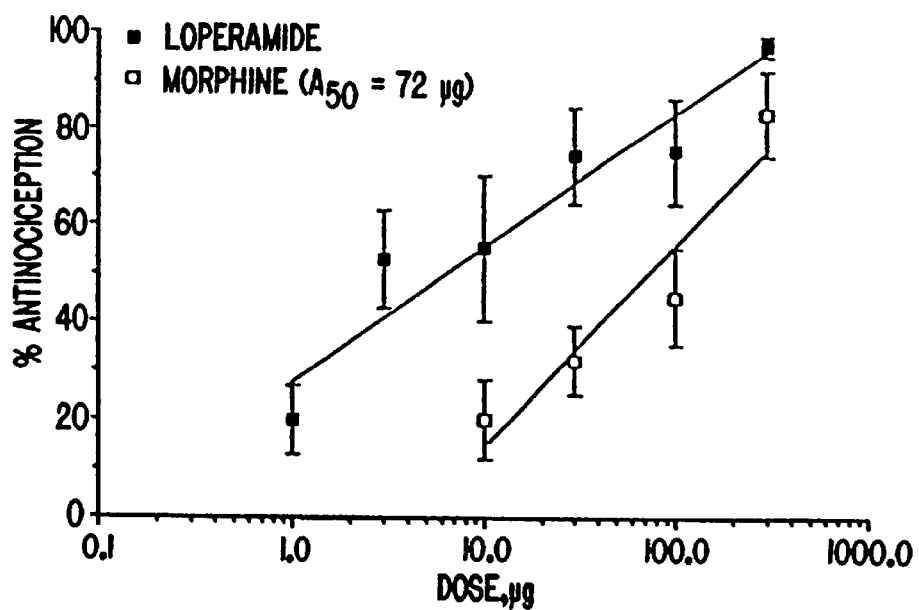
FIGS. 2 to 9 are graphical representations of in vivo pharmacological test studies described herein using compounds and methods provided herein.

When inflammation-induced tonic pain was produced by formalin injection into the paw, loperamide produced a dose-dependent antinociception in the second phase of flinching, as measured by a decrease in flinching responses, with an $A_{50}$ of 6 $\mu$g, as compared to an $A_{50}$ of 72 $\mu$g for morphine. Full efficacy was achieved at the highest dose of 300 $\mu$g, where practically no flinching behavior was observed. In FIG. 2, each data point is the mean±SEM of the average number of flinches per 5 min observation interval.

Figure 3:
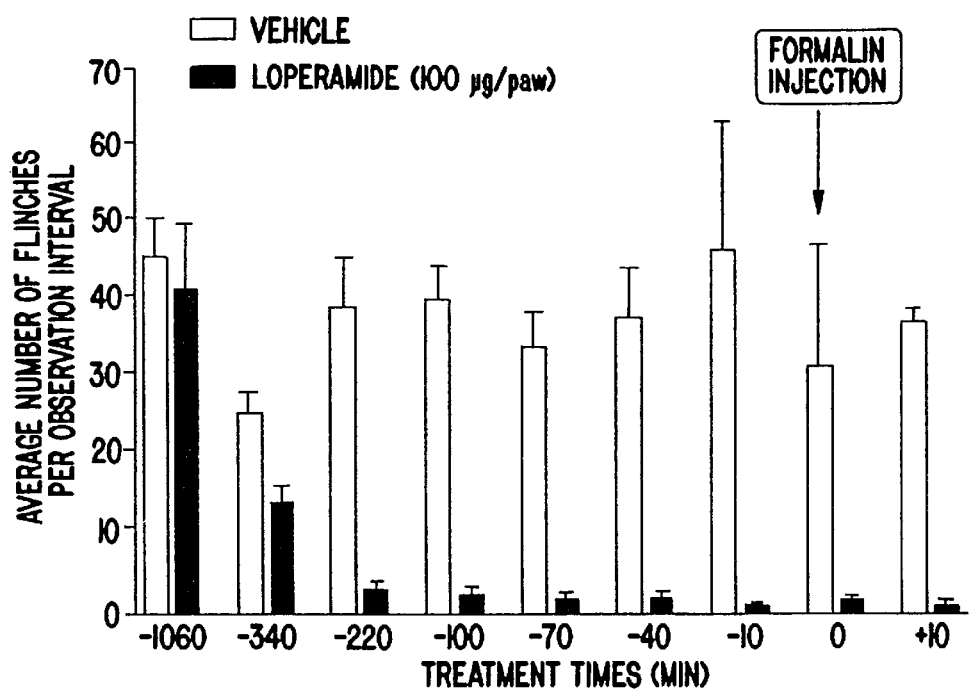

Administration of loperamide i.paw at a dose of 100 $\mu$g resulted in long-lasting antinociception (see FIG. 3). In this study, loperamide was injected at various times prior to (negative times in FIG. 3) or 10 min after i.paw injection of 50 $\mu$L of 5% formalin. The antinociception produced by loperamide was substantially immediate when administered at 10 min after formalin injection and 10 min before observation. Loperamide was efficacious when administered up to 6 hours prior to formalin injection. Also as shown in FIG. 3, control rats were injected with vehicle. Each data point is the mean±SEM of the average number of flinches per 5 min observation interval.

Figure 4:
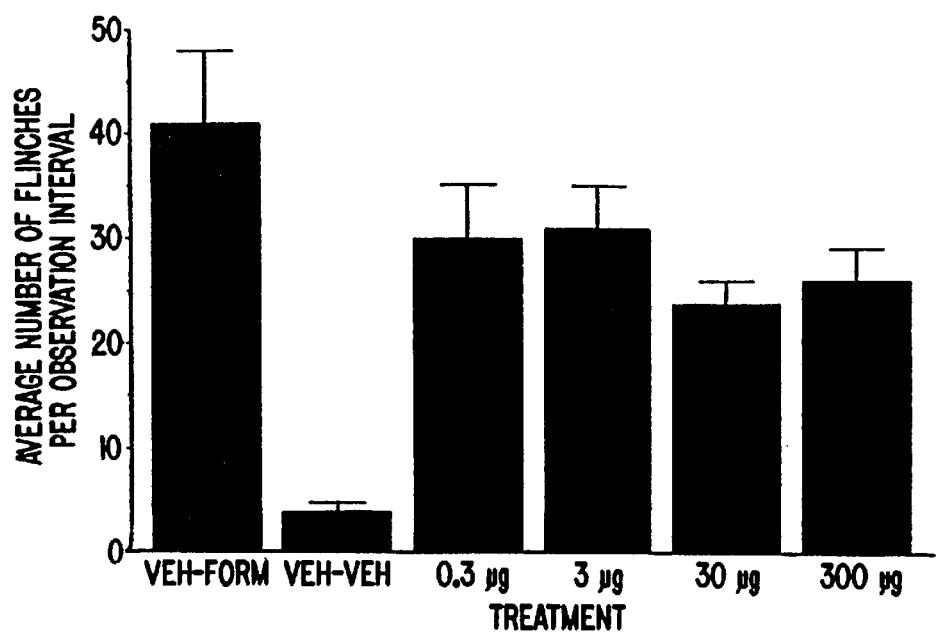

The effects of loperamide at doses of 0.3, 3, 30 and 300 $\mu$g on early phase flinching were studied to evaluate possible local anesthetic effects and to confirm the peripheral nature of the antihyperalgesia produced by the compound. This study is depicted graphically in FIG. 4. Inspection of FIG. 4 reveals that no significant effects of loperamide on early phase flinching were observed at any of the doses tested. Also shown in FIG. 4 is injection of control rats with formalin in vehicle (veh-form) and vehicle alone (veh-veh). Each data point in FIG. 4 is the mean±SEM of the average number of flinches per 5 min observation interval.

Figure 5:
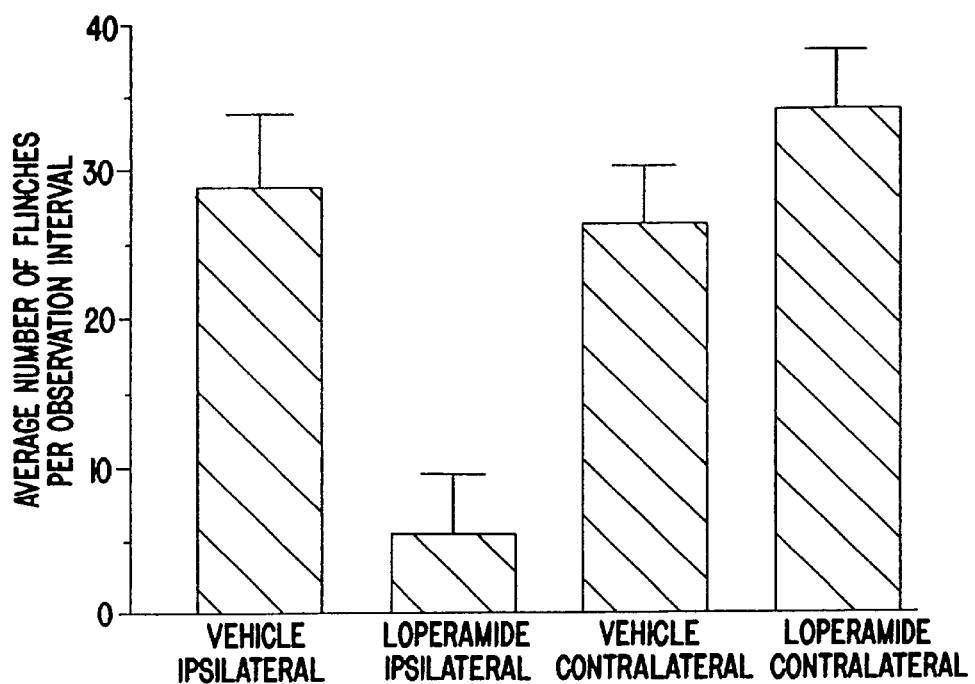

The peripheral selectivity of the antihyperalgesia produced by loperamide in the formalin assay was demonstrated also in a study in which ipsilateral injection of loperamide was performed into the same paw as formalin and contralateral injection was performed in the paw opposite to formalin. This is depicted in FIG. 5 which shows that loperamide at a dose of 100 $\mu$g i.paw exhibited antihyperalgesia activity when injected ipsilateral to formalin, but failed to produce antinociception when injected into the paw contralateral to formalin. If loperamide possessed central or systemic analgesic activity as a result of i.paw injection, antinociception would be observed also when loperamide was injected into the paw opposite to the one injected with formalin. Each data point in FIG. 5 is the mean±SEM of the average number of flinches per 5 min observation interval.

The studies which are described above and depicted graphically in FIGS. 2 to 5 demonstrate that loperamide administered directly into the paw reduces the pain associated with formalin-induced hyperalgesia. Loperamide has no action on early phase flinching and does not produce antinociception when injected into the contralateral paw, confirming the peripheral antihyperalgesic selectivity of the compound.

EXAMPLE 13

This example includes a description of Freund's complete adjuvant (FCA)-induced hyperalgesia tests.

Figure 6:
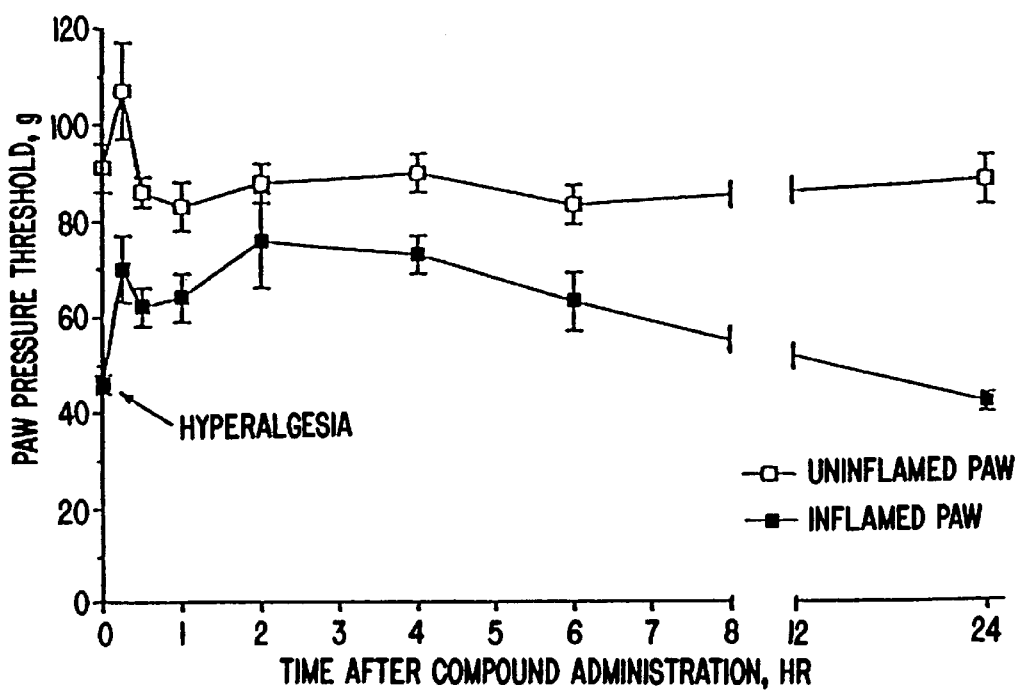
Figure 7:
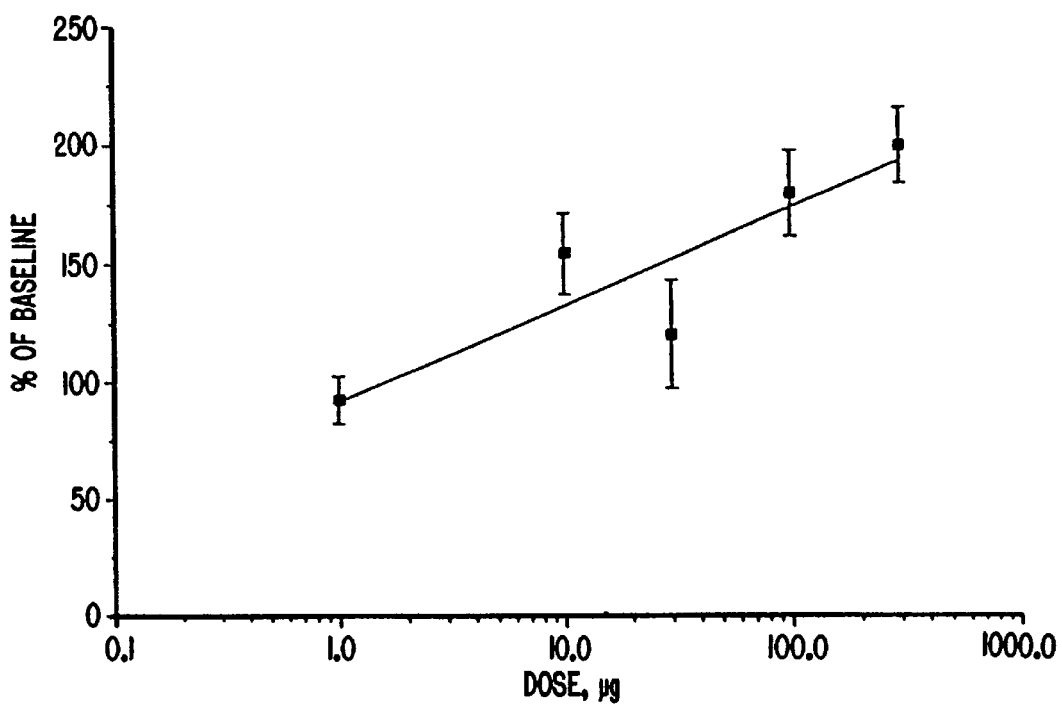

Hyperalgesia in response to inflammation was measured by determining the paw pressure threshold (PPT), measured in grams, of inflamed and non-inflamed paws of rats. Loperamide was injected intraplantar (i.pl.) 24 hours after i.pl. injection of 150 µL modified FCA, which corresponds to the time that inflammation and hyperalgesia due to FCA injection have reached a maximum. Loperamide at a dose of 100 µg produced an attenuation of the hyperalgesia induced by FCA which lasted from 15 min to 4 hours after a single injection (see FIG. 6). In FIG. 6, each data point is the mean±SEM PPT in grams at the respective time interval. Basal PPT values prior to drug administration were 46±2 g, inflamed paw, and 91±5 g uninflamed paw (n=5 to 11). The $ED_{50}$ for loperamide in this model was 20 µg when evaluated at 2 hours following injection, which is the peak time for antihyperalgesia induced by loperamide (see FIG. 7). No antinociception was observed in the uninflamed paw at up to 300 µg. With respect to the data graphed in FIG. 7, loperamide was administered at doses of 1, 10, 30, 100 and 300 µg (n=4 to 11), injected i.pl 24 hours following FCA injection. PPT in grams was measured 2 hours after drug injection. Control rats were injected with the appropriate vehicles. Data are expressed in FIG. 7 as the percent increase over basal PPT values.

In separate tests, loperamide also demonstrated antihyperalgesic activity in studies using carrageenan or yeast as the inflammatory stimulus.

EXAMPLE 14

This example includes a description of studies that demonstrate the antihyperalgesic effect of loperamide on tape stripping induced hyperalgesia.

Figure 8:
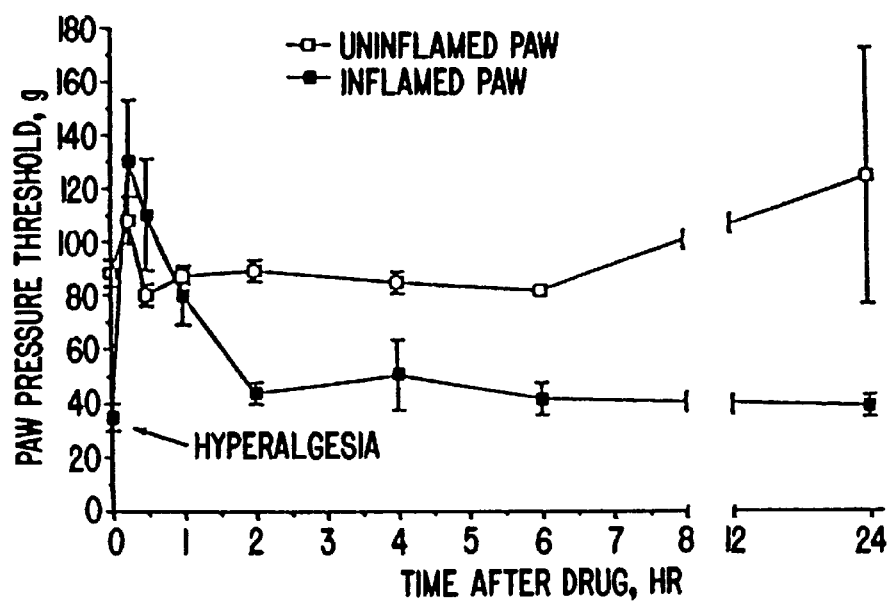

The right hind paws of anesthetized rats were treated by depilation with commercial hair remover followed by application and removal of Scotch Brand 810 tape a total of 20 times to remove the stratum corneum and to produce hyperalgesia. At 24 hours following tape stripping, hyperalgesia was quantitated by measuring paw pressure thresholds (PPT) prior to and following injection of loperamide in conscious rats. Loperamide at a dose of 100 µg was injected i.paw and PPTs were measured at various times following injection. Antinociception was observed at 15 min, 30 min, and 1 hour following injection (see FIG. 8). In FIG. 8, each data point is the mean±SEM PPT. Basal PPT values prior to loperamide administration were 35±5 g for the inflamed paw, and 88±5 g for the uninflamed paw.

Figure 9:
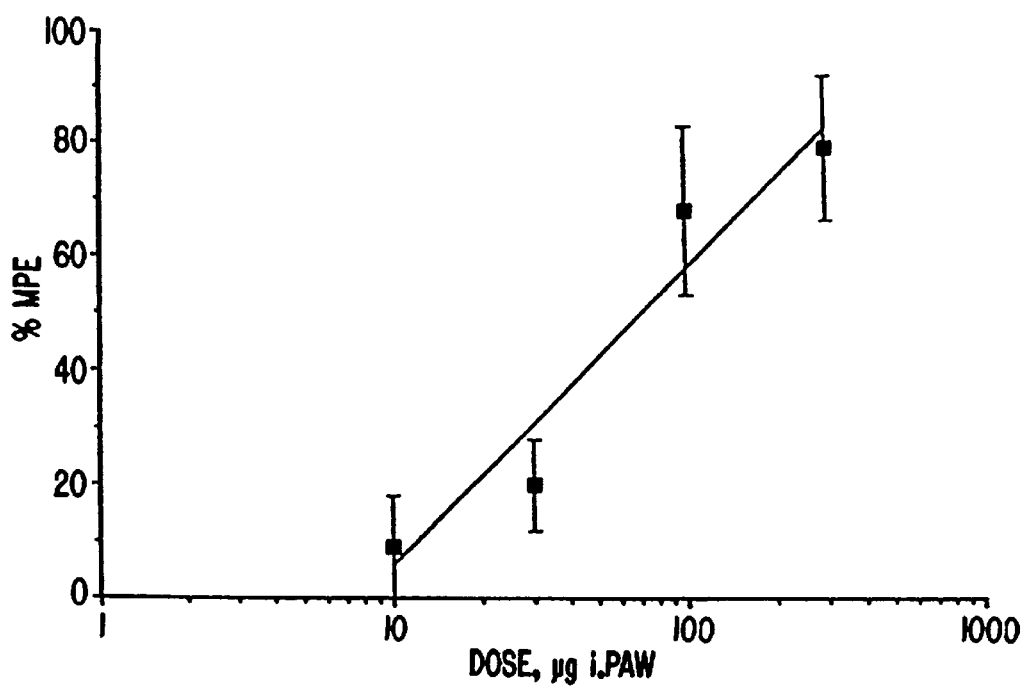

A dose response relationship for the antagonism by loperamide of the tape stripping induced is depicted in FIG. 9. Loperamide at doses of 10, 30, 100 and 300 µg were injected i.paw 24 hours following tape stripping, and PPTs were measured 15 min after each injection. Data are expressed as the mean±SEM of the % maximal possible effect (% MPE). The $ED_{50}$ for loperamide was 72 µg when measured at 15 min after intrapaw injection (see FIG. 9).

EXAMPLE 15

The procedures described in Examples 15 to 18 correspond substantially to the methods set forth in Stokbroekx et al. (1973) *J. Med. Chem.* 16:782–786 [see also e.g., U.S. Pat. No. 3,714,159].

Demonstratrations of Clinical Efficacy for the Treatment of Hyperalgesia

This example includes a description of human in vivo studies which demonstrate the antihyperalgesic activity of the compositions.

A. Treatment of Abrasions

In separate experiments, two white males, ages 54 and 52, generated an abrasion by the following procedure: a piece of 100 grit sandpaper was folded over an index finger or a small block of wood so that a rectangular surface of the sand paper approximately 50×15 mm or 130×40 mm, respectively, could be placed in contact with the skin. The subjects drew the sandpaper back and forth a total of 60 times (30 times in each direction) during a period of approximately 30 seconds over an area of skin on the inside of the forearm, approximately midway between the wrist and the elbow. Sufficient downward pressure on the sand paper was applied to produce a moderate stinging sensation throughout the process. The treatment produced a reddened abraded area, but no bleeding was observed. The stinging pain induced by the abrading process subsided within an hour or two, but was replaced after 8 to 12 hours by hyperalgesia of the abraded area which was assessed by each of the subjects running a finger lightly over the area, which continued to be red and which also appeared inflamed.

Approximately 12 hours after the abrasion was induced, the abraded area was divided into approximately two equal areas, separated by an area approximately 1 cm wide. To one area was applied approximately 0.2 grams of placebo cream and to the other area was applied approximately 0.2 grams of a 5% cream formulation of loperamide HCl. The 1 cm area separating the two equal areas of application received nothing. The applications were done "double blind" in that (1) a first individual weighed the placebo cream and the loperamide cream, coded them by letter, and gave them to a second individual who was unaware of the meaning of the letter coding; and (2) the second individual applied the creams to the subject, who was also unaware of the meaning of the letter coding.

The treated areas were separately covered with gauze bandages. This method of occlusion, in conjunction with the untreated area separating the two treated areas, effectively prevented the creams from mixing with each other. Three hours after creams were applied, the occlusive coverings were removed, excess cream was removed, and the two areas were tested for hyperalgesia by tactile and/or thermal stimulation. The subjects were able to distinguish clearly the degree of hyperalgesia in the two areas. When the code was broken, the area that had been selected as having less hyperalgesia was the area which had received the loperamide cream.

B. Treatment of Sunburn

A white, 49 year old female subject generated a controlled sunburn by the following procedure: two adhesive bandages (2 inch×3 inch) were placed on the subject's abdomen separated by a 1 inch wide area of exposed skin. The bandages were placed such that the long dimension (3 in) ran parallel to the longitudinal axis of the body. The exposed areas on the abdomen (including the 1 in wide area between the two patches) were then liberally covered with a commercial "sun block" cream and then the excess cream was removed. The effect of this application was to block exposure to sun in the entire area except for the two rectangular areas protected by the adhesive bandages. The adhesive bandages were then removed and the subject laid on her back with full exposure to the sun for approximately 2 hours.

The two areas which were not protected by the sun block developed typical sunburn-induced erythema and hyperalgesia. The hyperalgesia was quite pronounced from hour 12 onward. At hour 18, approximately 0.8 grams of placebo cream and 0.8 grams of a 5% cream formulation of loperamide HCl were applied separately to the two hyperalgesic areas. The application was performed "double blind" in that: (1) a first individual weighed the placebo and loperamide-containing creams, letter-coded them and gave them to a second individual who did not know the meaning of the codes, (2) the second individual delivered the coded samples to a third individual who also did not know the meaning of the codes. Finally, the creams were applied to the experimental subject who also did not know the meaning of the codes. The codes were not broken until 24 hours after the experiment had been completed.

Following application of the two creams, the two 2 in×3 in test sites were occluded by covering them with separate pieces of plastic wrap and sealing the edges of the plastic wrap with adhesive tape. This method of occlusion effectively prevented the creams from mixing with each other. Three hours after the creams were applied, the occlusive coverings were removed, the excess creams removed, and the two areas tested for the degree of hyperalgesia by tactile stimulation. The experimental subject was able to clearly distinguish the degrees of hyperalgesia in the two adjacent areas. When the code was broken the following day, the area that had been selected as having less hyperalgesia was determined to have been the area which received the loperamide cream.

C. Treatment of Frostbite

A male of Asian origin, age 49, generated a frost bite-like condition by the following procedure: a pellet of dry ice of approximately 10 to 15 mm of diameter was placed on the tip of each of two fingers of the right hand of the subject for approximately 30 to 35 seconds. This treatment resulted in the whitening of the skin over an area of approximately 50 mm$^2$ with stinging sensations and pain.

After approximately 18 to 20 hours, the tips of the fingers were visually red and a stinging pain was produced when light pressure was applied. To one of the fingers was applied approximately 0.1 grams of placebo cream and to the other finger was applied approximately 0.1 grams of a 5% cream formulation of loperamide HCl. The applications were done "double blind" in that: (1) a first individual weighed the placebo and loperamide-containing creams, letter-coded them and gave them to a second individual who did not know the meaning of the codes; and (2) the second person applied the creams to the subject, who also did not know the meaning of the codes.

The treatment areas were covered with bandages. After approximately 2 hours of treatment, the subject was able to distinguish clearly the degree of hyperalgesia in the two finger tips, especially when the area was subjected to light pressure. When the code was broken, the finger tip having less hyperalgesia was the one which received the loperamide cream.

EXAMPLE 16

This Example is directed to the preparation of loperamide (4-(p-chlorophenyl)-4-hydroxy-N,N-dimethyl-α,α-diphenyl-1-piperidinebutyramide hydrochloride).

A. Preparation of 4-bromo-2,2-diphenylbutyric acid

A mixture of 2,2-diphenyl-4-hydroxybutyric acid γ-lactone (600 g, 2.5 mol) and 48% HBr in AcOH (1200 ml) was stirred for 48 hrs. The precipitate was collected by filtration, washed with H$_2$O and toluene and crystallized from i-Pr$_2$O to give 4-bromo-2,2-diphenylbutyric acid (670 g, 84%), mp 135–137° C.

B. Preparation of dimethyl(tetrahydro-3,3-diphenyl-2-furylidene)ammonium bromide To a suspension of 4-bromo-2,2-diphenylbutyric acid from Step A (227 g, 0.70 mol) in CHCl$_3$ (1500 ml) was added dropwise SOCl$_2$ (160 ml). This mixture was refluxed for 4 hrs and allowed to cool, and the solvent was removed in vacuo. The crude 4-bromo-2,2-diphenylbutyroyl chloride (227 g, 93%) was used without further purification. To a solution of dimethylamine (54 g, 0.12 mol) and Na$_2$CO$_3$ (25.4 g, 0.24 mol) in H$_2$O (100 ml) was added dropwise a solution of 4-bromo-2,2-diphenylbutyroyl chloride (33.8 g, 0.1 mol) in toluene (100 ml), while the temperature was maintained between 0 and 5° C. The mixture was stirred for an additional 2 hrs and extracted with CHCl$_3$. The organic layer was dried (MgSO$_4$) and the solvent was removed in vacuo. The residue was crystallized from i-BuCOMc to give pure dimethyl-(tetrahydro-3,3-diphenyl-2-furylidene) ammonium bromide. (17.3 g, 50%): mp 181–182°: UV max (95% EtOH) 255 nm (540) and 261 (425); IR (KBr) 1675–1680 cm$^{-1}$ (C=N); NMR (CDCl$_3$) δ3.03 (s, 3), 3.50 (t, 2), 3.8 (s, 3), 4.89 (t, 2), and 7.51 ppm (s, 10).

C. Preparation of 4-(p-chlorophenyl)-4-hydroxy-N,N-dimethyl-α,α-diphenyl-1-piperidinebutyramide hydrochloride From a suspension of p-chlorophenyl-4-piperidinol (4.2 g, 0.02 mol) and Na$_2$CO$_3$ (8 g, 0.075 mol) in i-BuCOMe (250 ml), the H$_2$O was removed with the aid of a Dean-Stark trap. Then dimethyl(tetrahydro-3,3-diphenyl-2-furylidene) ammonium bromide from Step B (7.6 g, 0.022 mol) was added, and the mixture was refluxed for 2 hrs and filtered, and the solvent was removed in vacuo. The residue was dissolved into i-PrOH and neutralized with HCl gas. Crystallization from i-PrOH afforded pure 4-(p-chlorophenyl)-4-hydroxy-N,N-dimethyl-α,α-dipehnyl-1-piperidinebutyramide hydrochloride (6 g, 58%); mp 222–223° C.

EXAMPLE 17

Compounds in the following Table were prepared using the procedure described in Example 16 with the following changes: dimethylamine was replaced with methylethylamine (compound 17A); dimethylamine was replaced with pyrrolidine (compound 17B); and dimethylamine was replaced with piperidine and p-chlorophenyl-4-piperidinol was replaced with 4-phenyl-4-piperidinol (compound 17C):

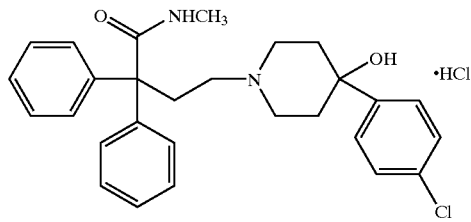

| Compounds | X | R |
|---|---|---|
| 17A | Cl | N(CH₃)(C₂H₅) |
| 17B | Cl | pyrrolidinyl |
| 17C | H | piperidinyl |

EXAMPLE 18

This example is directed to the preparation of 4-(p-chlorophenyl)-4-hydroxy-N-methyl-α,α-diphenyl-1-piperidinebutyramide hydrochloride, which has the following formula:

A. Preparation of N-(tetrahydro-3,3-diphenyl-2-furylidene) methylamine hydrobromide To a mixture of 35% aqueous methylamine (100 g, 1.13 mol) and Na₂CO₃ (106 g, 1 mol) in H₂O (1000 ml) and toluene (800 ml) was added dropwise 4-bromo-2,2-diphenylbutyroyl chloride (337.5 g, 1.13 mol) in toluene (200 ml), while the temperature was maintained between 0 and 15° C. The mixture was allowed to warm to room temperature and the precipitate was collected by filtration. The solid precipitate was then taken up into CHCl₃ the solution was dried (MgSO₄), and the solvent was removed in vacuo. The residue was crystallized from i-BuCOMe (isobutylmethylketone) to afford pure N-(tetrahydro-3,3-diphenyl-2-furylidene)methylamine hydrobromide (223 g, 67%), mp 159–161° C.

B. Preparation of 4-chloro-N-methyl-2,2-diphenylbutyramide

N-(Tetrahydro-3,3-diphenyl-2-furylidene)methylamine hydrobromide from Step A (33.2 g, 01. mol) was converted to base using standard methodology and dissolved in i-BuCOMe. This mixture was refluxed while dry HCl gas was bubbled through for 30 min. The solvent was removed in vacuo and the resulting residue was crystallized from i-Pr₂O to give pure 4-chloro-N-methyl-2,2-diphenylbutyramide (20.2 g, 70%), mp 150–152° C.

C. Preparation of 4-(p-chlorophenyl)-4-hydroxy-N-methyl-α,α-diphenyl-1-piperidinebutyramide hydrochloride A suspension of 4-chloro-N-methyl-2,2-diphenylbutyramide (1.4 g, 0.005 mol), 4-p-chlorophenyl-4-piperidinol (2.12 g, 0.01 mol), and trace Kl in i-BuCOMe (50 ml) was refluxed for 12 hrs. The reaction mixture was worked-up as described in Example 16 to provide 4-(p-chlorophenyl)-4-hydroxy-N-methyl-α,α-diphenyl-1-piperidinebutyramide hydrochloride (0.8 g, 35%), mp 236–238° C.

EXAMPLE 19

This example is directed to the preparation of the methyl p-toluenesulfonate salt of loperamide (4-(4-chlorophenyl)-4-hydroxy-N,N-dimethyl-α,α-diphenyl-1-piperidinebutanamide methyl p-toluenesulfonate).

To a suspension of the free base of loperamide (prepared from the corresponding hydrochloride salt and aqueous potassium carbonate, 0.95 g, 2 mmol) in acetone (20 mL) under a nitrogen atmosphere was added methyl p-toluenesulfonate (1.8 g, 9.94 mmol). The reaction mixture was then stirred at 25° C. for 24 hrs and heated to reflux with stirring for 48 hrs. The reaction mixture was cooled to room temperature and the solvent was removed under reduced pressure to provide a gum. The gum was triturated with 4-methyl-2-pentanone (i-BuCOMe) to furnish a white solid which was recrystallized from 4-methyl-2-pentanone to provide the loperamide methyl p-toluenesulfonate (0.75 g, 56%), mp 213–215° C.

EXAMPLE 20

This example includes a summary of comparative in vitro and in vivo studies that were conducted using compounds that may be employed in the methods and compositions provided herein and compounds of the prior art.

| | In Vitro Binding Affinities | | | In Vivo Antihyperalgesic Activity | | | | |
|---|---|---|---|---|---|---|---|---|
| | Human Opiate Receptors $K_i$, nM | | | Formalin-Induced Flinching (Late Phase) | | FCA-Induced Inflammation % | | Tape Stripping-Induced Inflammation | |
| Compound | μ | δ | κ | $ED_{50}$, μg i. paw | % Maximal Efficacy | $ED_{50}$, μg i. pl. | % Increase Over Baseline | $ED_{50}$, μg i. paw | % Maximal Efficacy |
| Ioperamide | 3.2 | 48 | 1160 | 6 | 97 | 21 | 108 | 71 | 80 |
| Example 17A | 4 | 123 | 1420 | 4.8 | 91 | — | — | — | — |

-continued

| | In Vitro Binding Affinities Human Opiate Receptors $K_i$, nM | | | In Vivo Antihyperalgesic Activity | | | | | |
|---|---|---|---|---|---|---|---|---|---|
| | | | | Formalin-Induced Flinching (Late Phase) | | FCA-Induced Inflammation % | | Tape Stripping-Induced Inflammation | |
| Compound | $\mu$ | $\delta$ | $\kappa$ | $ED_{50}$, μg i. paw | % Maximal Efficacy | $ED_{50}$, μg i. pl. | Increase Over Baseline | $ED_{50}$, μg i. paw | % Maximal Efficacy |
| Example 17B | 2.2 | 68 | 2230 | 4.9 | 86 | — | — | — | — |
| Example 17C | 2.5 | 15 | 4680 | 19 | 87 | — | — | — | — |
| Example 18 | 1.1 | 200 | >1000 | 3.2 | 88 | — | — | — | — |
| Example 19 | 43 | >10000 | >10000 | 93 | 69 | — | — | — | — |
| Deiphenoxylate | 44 | 315 | 1000 | 158 | 61 | — | — | — | — |
| Difenoxin[†] | 13 | 56 | >1000 | 33 | 90 | — | — | — | — |
| Morphine | 19 | 213 | 230 | 72 | 83 | 26 | 192 | 631 | 55 |

[†]Difenoxin is 1-(3-cyano-3,3-diphenylpropyl)-4-phenyl-4-piperidinecarboxylic acid.

Since modifications will be apparent to those of skill in this art, it is intended that this invention be limited only by the scope of the appended claims.

What is claimed is:

1. A method of preventing or treating peripheral hyperalgesia, comprising administering topically to a mammal in need of such prevention or treatment an effective amount of a composition, comprising in a vehicle formulated for topical administration, one or more compounds of the following formula (I):

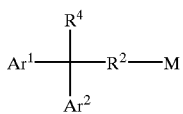

where M is: 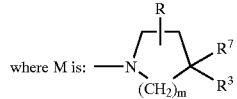

wherein:
each of $Ar^1$ and $Ar^2$ are independently selected from (i) or (ii) as follows:
(i) a 6- to 10-membered aryl ring system or a 5- to 10-membered heteroaryl ring system containing one or more heteroatoms, wherein the aryl and heteroaryl ring systems are each optionally substituted with one or more aryl group substituents, or
(ii) optionally substituted phenyl or pyridyl groups which, together with the carbon atoms to which they are attached, form a fused ring system so that the compounds of formula (I) have the formula:

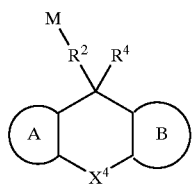

A and B independently represent fused phenyl or pyridyl rings;
$X^4$ is a direct bond, —(CH$_2$)$_n$—, —CH=CH—, —CH=CHCH$_2$—, —(CH$_2$)$_p$O(CH$_2$)$_q$—, —(CH$_2$)$_p$S(O)$_r$(CH$_2$)$_q$—, —(CH$_2$)$_p$NR$^{21}$(CH$_2$)$_q$— or

$R^{21}$ is hydrogen or lower alkyl;
m is an integer from 1 to 3;
n is an integer from 0 to 3;
each of p and q is 0 or 1, and the sum of p and q is no greater than 2;
r is 0 to 2;
$R^2$ is a direct bond, straight or branched chain alkylene of 1 to 12 carbon atoms, which is optionally substituted with one or more hydroxy groups, or alkenylene of 2 to 6 carbon atoms and one or two double bonds;
$R^3$ is selected from $Ar^3$, —Y—$Ar^3$ where Y is alkylene of 1 to 3 carbon atoms, alkenylene of 2 to 4 carbon atoms, cycloalkyl of 3 to 8 carbons, heterocycle, alkenyl, alkanoyl, alkenoyl of 3 to 10 carbons and 1 to 3 double bonds, aroyl, heteroaroyl, alkoxycarbonyl, alkenyloxycarbonyl of 3 to 10 carbons and 1 to 3 double bonds, aryloxycarbonyl, formyl (—CHO), cyano, aminocarbonyl (—CONH$_2$), alkylaminocarbonyl, dialkylaminocarbonyl, arylaminocarbonyl, diarylaminocarbonyl, arylalkylaminocarbonyl, or

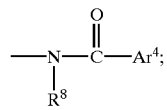

where any of the aryl groups are unsubstituted or substituted with one or more aryl substitutents, and any other groups set forth for $R^3$ are unsubstituted or substituted with halo, hydroxy or alkoxy; and
$R^8$ is hydrogen or straight or branched chain alkyl of 1 to 6 carbon atoms, which is unsubstituted or substituted with an alkyl group substitutent;
$Ar^3$ is a 6- to 10-membered aryl ring system or a 5- to 10-membered heteroaryl ring system containing one or more heteroatoms in which the aryl and heteroaryl ring systems are each optionally substituted with one or more aryl group substituents;

$Ar^4$ is
  (i) heterocycle containing 1 ring or 2 or more fused rings, wherein each ring contains one or more heteroatoms and is optionally substituted with one or more aryl group substituents;
  (ii) a radical of the formula:

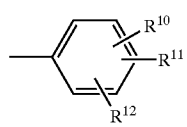

where, $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, $C_{3-6}$alkynyloxy, arylalkyloxy or aryloxy, in which each group is unsubstituted or substituted with one or more substituents selected from halo, halo alkyl and alkyl, and the alkyl groups are straight or branched chains that are lower alkyl; or
  (iii) 1- or 2-naphthyl, dihydronaphthyl, tetrahydronaphthyl, indenyl or dihydroindenyl, each of which is optionally substituted with one or more aryl group substituents;

R is hydrogen, alkyl, halo, haloalkyl, $OR^9$ or alkenyl;

$R^9$ is hydrogen, alkyl, arylalkyl, alkylcarbonyl, aminoalkyl, alkylaminoalkyl or dialkylaminoalkyl, in which the alkyl groups are straight or branched chains of 1 to 12 carbon atoms;

$R^4$ is selected from among:
  (i) a 6- to 10-membered aryl ring system or a 5- to 10-membered heteroaryl ring system containing one or more heteroatoms, wherein the aryl and heteroaryl ring systems are each optionally substituted with one or more aryl group substituents;
  (ii) heterocyclic rings which contain one to three heteroatoms and which are unsubstituted or substituted with halo, halo lower alkyl, hydroxy, lower alkoxy or lower alkyl;
  (iii) alkyl of 1 to 8 carbons, which is optionally substituted with hydroxy or alkylcarbonyloxy; alkenyl of 3 to 6 carbons; cycloalkylalkyl in which the cycloalkyl contains 3 to 8 carbons and the alkyl contains 1 to 3 carbons; cycloalkenylalkyl in which the cycloalkenyl contains 3 to 8 carbons and the alkyl contains 1 to 3 carbons;

(iv)

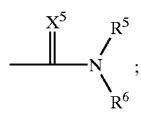

$X^5$ is O or S;
  $R^5$ and $R^6$ are independently selected from:
    (a) hydrogen, straight or branched chain alkyl of 1 to 12 carbon atoms, straight or branched chain alkenyl of 2 to 12 carbon atoms and one or two double bonds, a 6- to 10-membered aryl ring system, which is optionally substituted with one or more aryl group substituents, or arylalkyl; and
    (b) carbon chains, heteroatoms, and carbon chains containing one or more heteroatoms, so that, together with the nitrogen atom to which they are attached, form a 3- to 10-membered heterocyclic ring containing one or more heteroatoms that is unsubstituted or substituted with halo, halo lower alkyl or lower alkyl, hydroxy, lower alkoxy;
  (v) cyano, formyl, alkoxycarbonyl, aryloxycarbonyl, alkylcarbonyl or arylcarbonyl;
  (vi) —$NR^5COR^5$; and
  (vii) —$S(O)_r$alkyl or —$S(O)_r$aryl, where r is 1 or 2; and $R^7$ is selected from among:
  hydrogen;
  —OH;
  —$R^{14}OR^{13}$ in which $R^{13}$ is hydrogen, lower alkyl or alkanoyl containing 2 to 5 carbon atoms, and $R^{14}$ is lower alkenyl or lower alkyl;
  —$CH_2NR^{15}R^{16}$ in which $R^{15}$ is hydrogen, lower alkyl, lower alkanoyl, aryl or aroyl and $R^{16}$ is hydrogen or lower alkyl or, together with the nitrogen atom to which they are attached, $R^{15}$ and $R^{16}$ form a 3 to 7-membered ring which optionally contains an additional heteroatom selected from oxygen, nitrogen or sulfur;
  —$OR^{15}$;
  —C(O)H;
  —CN;
  —C(=O)—$NR^5R^6$;
  alkyl;
  aryl;
  —$C(O)OR^{17}$ in which $R^{17}$ is hydrogen, alkyl of 1 to 7 carbon atoms, alkenyl of 3 to 7 carbon atoms, an optionally substituted aryl ring system, an optionally substituted heteroaryl ring system containing one or more heteroatoms, arylalkyl, or a pharmaceutically acceptable cation;

wherein the optional aryl group substituents are selected from halo, hydroxy, alkyl, cycloalkyl, cycloalkylalkyl, aryl, heteroaryl, arylalkyl, heteroarylalkyl, alkenyl containing 1 to 2 double bonds, alkynyl containing 1 to 2 triple bonds, haloalkyl, polyhaloalkyl, formyl, alkylcarbonyl, arylcarbonyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfony;

or a salt, hydrate or N-oxide thereof;

the amount is effective to treat or prevent hyperalgesia; and wherein $R^3$ is $Ar^3$; —Y—$Ar^3$, where Y is alkylene of 1 to 3 carbon atoms; alkenylene of 2 to 4 carbon atoms; cycloalkyl of 3 to 8 carbons; heterocyclyl; alkenyl; alkanoyl that is optionally substituted with halo, hydroxy or alkoxy; alkenoyl of 3 to 10 carbons and 1 to 3 double bonds; optionally substituted aroyl; heteroaroyl; alkoxycarbonyl; alkenyloxycarbonyl of 3 to 10 carbons and 1 to 3 double bonds; aryloxycarbonyl; formyl (—CHO); cyano; aminocarbonyl (—CONH$_2$); alkylaminocarbonyl; dialkylaminocarbonyl; arylaminocarbonyl; diarylaminocarbonyl or arylalkylaminocarbonyl.

2. A method of preventing or treating peripheral hyperalgesia of claim 1, wherein the compounds of formula (I) are of the formula:

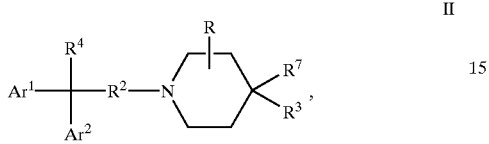
II wherein:

$R^4$ is phenyl, pyridyl, cyano or

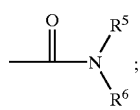

$R^5$ and $R^6$ are independently selected from:
(i) hydrogen, lower alkyl, phenyl or lower alkenyl, or
(ii) together with the nitrogen atom to which they are attached form a heterocycle selected from 1,3,4-oxadiazolyl, 4-morpholinyl, or di($C_1$–$C_6$ alkyl)-morpholinyl;

$R^2$ is —(CH$_2$)$_2$— or —CH$_2$CH(CH$_3$)—;

$R^7$ is —OH, —C(O)OR$^{17}$ in which R$^{17}$ is hydrogen, methyl or ethyl, or —C(O)H;

R is hydrogen, lower alkyl, —C(O)H, or —C(O)OH and is at the 3-position as follows:

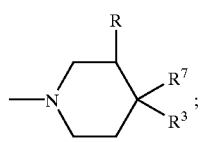

and $R^3$ is phenyl or halo-substituted phenyl.

3. The method of claim 2, wherein:
$R^7$ is —OH, —C(O)OH or —C(O)OCH$_2$CH$_3$;
$R^3$ is phenyl optionally substituted with alkyl, alkoxyalkyl, halo or trifluoroalkyl;
R is hydrogen or alkyl of 1 to 3 carbon atoms;
$R^2$ is lower alkylene;
$R^4$ is phenyl, pyridyl or:

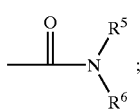

$R^5$ and $R^6$ are independently selected from:
(i) hydrogen, alkyl, phenyl, phenylalkyl or 2-propenyl, in which the alkyl groups are lower alkyl; or
(ii) together with the nitrogen to which they are attached form pyrrolidinyl, piperidinyl, $C_1$–$C_6$ alkylpiperidinyl, 4-morpholinyl or 2,6-di($C_1$–$C_6$ alkyl)morpholinyl; and Ar$^1$ and Ar$^2$ are independently selected from phenyl or pyridyl.

4. The method of claim 3, wherein:
R is hydrogen or methyl;
$R^3$ is phenyl optionally substituted with alkyl, alkoxyalkyl, halo or trifluoroalkyl;
$R^2$ is alkylene containing from 1 to 4 carbons;
Ar$^1$ and Ar$^2$ are independently phenyl, which is unsubstituted or substituted with lower alkyl, alkoxy lower alkyl, halo or halo lower alkyl;
$R^4$ is cyano or:

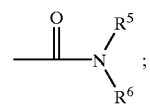

$R^5$ and $R^6$ are independently selected from:
(i) hydrogen, lower alkyl, phenyl, phenyl lower alkyl or 2-propenyl; or
(ii) together with the nitrogen atom to which they are attached, form pyrrolidinyl, piperidinyl, $C_1$–$C_6$ alkylpiperidinyl, 4-morpholinyl or 2,6-di($C_1$–$C_6$ alkyl)morpholinyl.

5. The method of claim 4 in which the compound of formula has the formula:

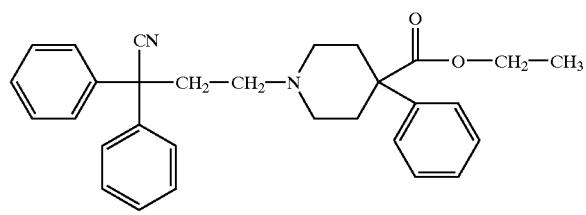

or

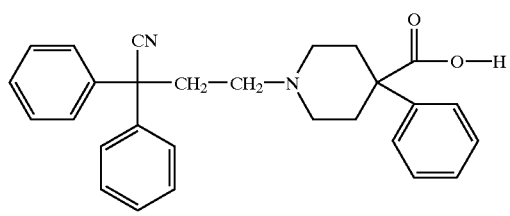

or a salt or N-oxide thereof.

6. The method of claim 5 wherein:
Ar$^1$ and Ar$^2$ are phenyl,
R is hydrogen or methyl,
$R^2$ is —(CH$_2$)$_2$— or —CH$_2$CH(CH$_3$)—,
$R^5$ and $R^6$ are independently methyl or ethyl or, together with the nitrogen to which they are attached, form pyrrolidinyl or piperidinyl;
$R^3$ is unsubstituted phenyl, 4-chlorophenyl, 4-bromophenyl, 4-fluorophenyl, 3,4-di-halophenyl or 3-trifluoromethylphenyl; and
$R^7$ is —OH.

7. The method of claim 6, wherein the compound is selected from compounds in which:
(i) Ar$^1$ and Ar$^2$ are phenyl, R is hydrogen, $R^2$ is —(CH$_2$)$_2$—, $R^5$ and $R^6$, together with the nitrogen to which they are attached, form pyrrolidine, and $R^3$ is 4-chlorophenyl or 3,4-dichlorophenyl:

(ii) Ar¹ and Ar² are phenyl, R is hydrogen, R² is —(CH₂)₂—, R⁵ and R⁶, together with the nitrogen to which they are attached, form piperidinyl, and R³ is phenyl;

(iii) Ar¹ and Ar² are phenyl, R² is —(CH₂)₂—, R is hydrogen, R⁵ and R⁶ are methyl and R³ is 4-bromophenyl;

(iv) Ar¹ and Ar² are phenyl, R² is —(CH₂)₂—, R is hydrogen, R⁵ is methyl, R⁶ is ethyl and R³ is 4-chlorophenyl;

(v) Ar¹ and Ar² are phenyl, R² is —CH₂CH(CH₃)—, R is hydrogen, R⁵ and R⁶ are methyl and R³ is 4-fluorophenyl; and (vi) Ar¹ and Ar² are phenyl, R² is —(CH₂)₂—, R is 4-methyl, R⁵ and R⁶ are methyl and R³ is 3-trifluoromethylphenyl or phenyl.

8. The method of claim 2, wherein the composition comprises 4-(p-chlorophenyl)-4-hydroxy-N-N-dimethyl-α,α-diphenyl-1-piperidinebutyramide that has the formula:

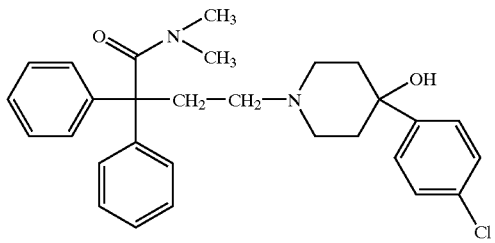

or a salt or N-oxide thereof.

9. The method of claim 8, wherein the peripheral hyperalgesia results from a bite, sting, burn, viral or bacterial infection, oral surgery, tooth extraction, injury to the skin and flesh, wound, abrasion, contusion, surgical incision, sunburn, rash or joint inflammation.

10. The method of claim 2, wherein the composition comprises 4-(p-chlorophenyl)-4-hydroxy-N-N-dimethyl-α,α-diphenyl-1-piperidinebutyramide hydrochloride.

11. The method of claim 1, wherein the compounds of formula (I) are of the formula:

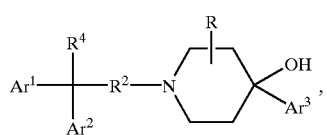

wherein:

Ar¹ and Ar² are each independently a 6- to 10-membered aryl ring system or a 5- to 10-membered heteroaryl ring system, wherein the aryl and heteroaryl ring systems are optionally substituted with up to three substituents selected from halo, alkyl and haloalkyl;

R² is straight or branched chain alkylene of 1 to 12 carbon atoms, or straight or branched chain alkenylene of 2 to 12 carbon atoms containing one double bond;

R is hydrogen, alkyl, halo lower alkyl or halo;

R⁴ is

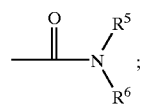

R⁵ and R⁶ are independently selected from:
(i) hydrogen, straight or branched chain alkyl or straight or branched chain alkenylene, or
(ii) together with the nitrogen atom to which they are attached, they form a 3- to 10-membered heterocyclic ring containing one or two heteroatoms; and Ar³ is a 6- to 10-membered aryl ring system or a 5- to 10-membered heteroaryl ring system containing one or more heteroatoms, wherein the aryl and heteroaryl ring systems are optionally substituted with one or more aryl group substituents.

12. The method of claim 1, wherein the compounds of formula (I) are of the formula:

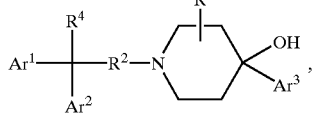

wherein:

Ar¹ and Ar² are each independently selected from phenyl, which is optionally substituted with up to three substituents selected from halo, halo alkyl or alkyl in which the alkyl groups are straight or branched chains of 1 to 6 carbons;

R² is straight or branched chain alkylene of 1 to 3 carbons or alkenyl of 2 to 3 carbons containing one double bond;

R is hydrogen, lower alkyl, halo lower alkyl or halo, and is in the 3-position;

R⁴ is:

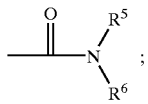

R⁵ and R⁶ are independently selected from:
(i) hydrogen, alkyl or alkenyl, in which the carbon chains are straight or branched chain of 1 to 6 carbons, or
(ii) together with the nitrogen atom to:which they are attached, they form pyrrolidinyl, piperidinyl, alkylpiperidinyl, morpholinyl, or di(C₁–C₆ alkyl)-morpholinyl; and Ar³ is a 6- to 10-membered aryl ring system, which is unsubstituted or substituted with up to three substituents selected from halo, halo lower alkyl and lower alkyl.

13. A method of preventing or treating peripheral hyperalgesia of claim 1, wherein the compounds of formula (I) are of the formula:

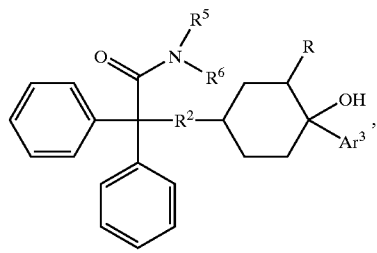

IV wherein:
Ar³ is phenyl, which is optionally substituted with halo; and
R² is alkylene containing 1 to 3 carbon atoms.

14. The method of claim 1, wherein the administration is effected intra-articularly.

15. The method of claim 1, wherein the composition is formulated for topical application to the eye.

16. A method of treating or preventing pain or irritation associated with hyperalgesia, comprising intra-articularly administering to a mammal in need of such treatment an effective amount of diphenoxylate or difenoxin, wherein the amount is effective to treat or prevent the hyperalgesia.

17. A method of preventing or treating peripheral hyperalgesia, comprising administering topically to a mammal in need of such prevention or treatment an effective amount of a composition, comprising in a vehicle formulated for topical administration, one or more compounds of the following formula (I):

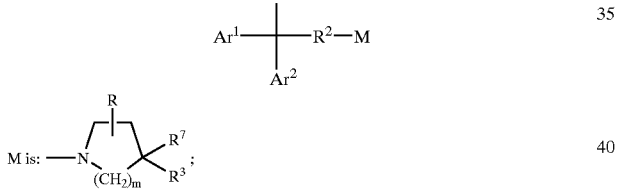

I wherein: each of Ar¹ and Ar² are independently selected from (i) or (ii) as follows:
(i) a 6- to 10-membered aryl ring system or a 5- to 10-membered heteroaryl ring system containing one or more heteroatoms, wherein the aryl and heteroaryl ring systems are each optionally substituted with one or more aryl group substituents, or
(ii) optionally substituted phenyl or pyridyl groups which, together with the carbon atoms to which they are attached, form a fused ring system so that the compounds of formula (I) have the formula:

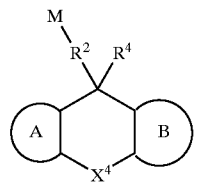

A and B independently represent fused phenyl or pyridyl rings;
$X^4$ is a direct bond, $-(CH_2)_n-$, $-CH=CH-$, $-CH=CHCH_2-$, $-(CH_2)_pO(CH_2)_q-$, $-(CH_2)_pS(O)_r(CH_2)_q-$, $-(CH_2)_pNR^{21}(CH_2)_q-$ or

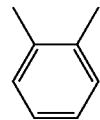

$R^{21}$ is hydrogen or lower alkyl;
m is an integer from 1 to 3;
n is an integer from 0 to 3;
each of p and q is 0 or 1, and the sum of p and q is no greater than 2;
r is 0 to 2;
$R^2$ is a direct bond, straight or branched chain alkylene of 1 to 12 carbon atoms, which is optionally substituted with one or more hydroxy groups, or alkenylene of 2 to 6 carbon atoms and one or two double bonds;
$R^3$ is selected from $Ar^3$, $-Y-Ar^3$ where Y is alkylene of 1 to 3 carbon atoms, alkenylene of 2 to 4 carbon atoms, cycloalkyl of 3 to 8 carbons, heterocycle, alkenyl, alkanoyl, alkenoyl of 3 to 10 carbons and 1 to 3 double bonds, aroyl, heteroaroyl, alkoxycarbonyl, alkenyloxycarbonyl of 3 to 10 carbons and 1 to 3 double bonds, aryloxycarbonyl, formyl (—CHO), cyano, aminocarbonyl (—CONH₂), alkylaminocarbonyl, dialkylaminocarbonyl, arylaminocarbonyl, diarylaminocarbonyl, arylalkylaminocarbonyl, or

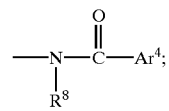

where any of the aryl groups are unsubstituted or substituted with one or more aryl substitutents, and any other groups set forth for $R^3$ are unsubstituted or substituted with halo, hydroxy or alkoxy; and
$R^8$ is hydrogen or straight or branched chain alkyl of 1 to 6 carbon atoms, which is unsubstituted or substituted with an alkyl group substitutent;
Ar³ is a 6- to 10-membered aryl ring system or a 5- to 10-membered heteroaryl ring system containing one or more heteroatoms in which the aryl and heteroaryl ring systems are each optionally substituted with one or more aryl group substituents;
Ar⁴ is
(i) heterocycle containing 1 ring or 2 or more fused rings, wherein each ring contains one or more heteroatoms and is optionally substituted with one or more aryl group substituents;
(ii) a radical of the formula:

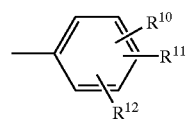

where, $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, $C_{3-6}$alkynyloxy, arylalkyloxy or aryloxy, in which each group is unsubstituted or substituted with one or more substituents selected from halo, halo alkyl and alkyl, and the alkyl groups are straight or branched chains that are lower alkyl; or (iii) 1- or 2-naphthyl, dihydronaphthyl, tetrahydronaphthyl, indenyl or dihydroindenyl, each of which is optionally substituted with one or more aryl group substituents;

R is hydrogen, alkyl, halo, haloalkyl, $OR^9$ or alkenyl;

$R^9$ is hydrogen, alkyl, arylalkyl, alkylcarbonyl, aminoalkyl, alkylaminoalkyl or dialkylaminoalkyl, in which the alkyl groups are straight or branched chains of 1 to 12 carbon atoms;

$R^4$ is selected from among:
(i) a 6- to 10-membered aryl ring system or a 5- to 10-membered heteroaryl ring system containing one or more heteroatoms, wherein the aryl and heteroaryl ring systems are each optionally substituted with one or more aryl group substituents;
(ii) heterocyclic rings which contain one to three heteroatoms and which are unsubstituted or substituted with halo, halo lower alkyl, hydroxy, lower alkoxy or lower alkyl;
(iii) alkyl of 1 to 8 carbons, which is optionally substituted with hydroxy or alkylcarbonyloxy; alkenyl of 3 to 6 carbons; cycloalkylalkyl in which the cycloalkyl contains 3 to 8 carbons and the alkyl contains 1 to 3 carbons; cycloalkenylalkyl in which the cycloalkenyl contains 3 to 8 carbons and the alkyl contains 1 to 3 carbons;

(iv)

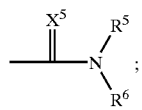

$X^5$ is O or S;
$R^5$ and $R^6$ are independently selected from:
(a) hydrogen, straight or branched chain alkyl of 1 to 12 carbon atoms, straight or branched chain alkenyl of 2 to 12 carbon atoms and one or two double bonds, a 6- to 10-membered aryl ring system, which is optionally substituted with one or more aryl group substituents, or arylalkyl; and
(b) carbon chains, heteroatoms, and carbon chains containing one or more heteroatoms, so that, together with the nitrogen atom to which they are attached, form a 3- to 10-membered heterocyclic ring containing one or more heteroatoms that is unsubstituted or substituted with halo, halo lower alkyl or lower alkyl, hydroxy, lower alkoxy;
(v) cyano, formyl, alkoxycarbonyl, aryloxycarbonyl, alkylcarbonyl or arylcarbonyl;
(vi) —$NR^5COR^5$; and
(vii) —$S(O)_r$alkyl or —$S(O)_r$aryl, where r is 1 or 2; and $R^7$ is selected from among:
hydrogen;
—OH;
—$R^{14}OR^{13}$ in which $R^{13}$ is hydrogen, lower alkyl or alkanoyl containing 2 to 5 carbon atoms, and $R^{14}$ is lower alkenyl or lower alkyl;
—$CH_2NR^{15}R^{16}$ in which $R^{15}$ is hydrogen, lower alkyl, lower alkanoyl, aryl or aroyl and $R^{16}$ is hydrogen or lower alkyl or, together with the nitrogen atom to which they are attached, $R^{15}$ and $R^{16}$ form a 3 to 7-membered ring which optionally contains an additional heteroatom selected from oxygen, nitrogen or sulfur;
—$OR^{15}$;
—C(O)H;
—CN;
—C(=O)—$NR^5R^6$;
alkyl;
aryl;
—$C(O)OR^{17}$ in which $R^{17}$ is hydrogen, alkyl of 1 to 7 carbon atoms, alkenyl of 3 to 7 carbon atoms, an optionally substituted aryl ring system, an optionally substituted heteroaryl ring system containing one or more heteroatoms, arylalkyl, or a pharmaceutically acceptable cation;

wherein the optional aryl group substituents are selected from halo, hydroxy, alkyl, cycloalkyl, cycloalkylalkyl, aryl, heteroaryl, arylalkyl, heteroarylalkyl, alkenyl containing 1 to 2 double bonds, alkynyl containing 1 to 2 triple bonds, haloalkyl, polyhaloalkyl, formyl, alkylcarbonyl, arylcarbonyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfony;

or a salt, hydrate or N-oxide thereof;
the amount is effective to treat or prevent hyperalgesia; and
the peripheral hyperalgesia results from a bite, sting, burn, viral or bacterial infection, oral surgery, tooth extraction, injury to the skin and flesh, wound, abrasion, contusion, surgical incision, sunburn, rash or joint inflammation.

18. A method of treating or preventing peripheral hyperalgesia, comprising topically applying or locally administering to a mammal in need of such treatment an effective amount of a composition, comprising an antihyperalgesically effective amount of diphenoxylate or difenoxin or derivatives or analogs thereof in a vehicle formulated for topical application or local administration, wherein diphenoxylate is (2,2-diphenyl-4-[(4-carbethoxy-4-phenyl)piperidino]butyronitrile) and has the formula:

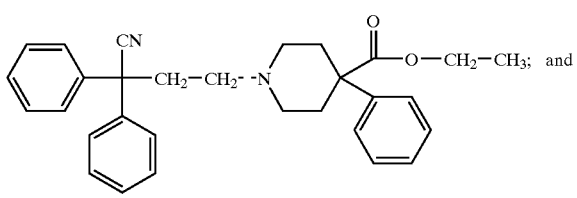

difenoxin is 1-(3-cyano-3,3-diphenylpropyl)-4-phenyl-4-piperidinecarboxylic acid.

19. The method of claim 18, wherein the hyperalgesic conditions is an ophthalmic conditions.

20. The method of claim 19, wherein the ophthalmic condition is selected from among corneal abrasions, post-radial keratectomy, eye surgery and inflammatory conjunctivitis.

21. The method of claim 18, wherein the compound is diphenoxylate.

22. The method of claim 18, which comprises administering topically the composition to a surface of the mammal, wherein the surface is selected from the group consisting of skin and mucosal surfaces.

23. The method of claim 22, wherein the surface comprises a skin surface.

24. The method of claim 23, wherein the hyperalgesic condition is associated with burns, abrasions, bruises, contusions, frostbite, rashes, acne, insect bites/stings, skin ulcers, mucositis, gingivitis, bronchitis, laryngitis, sore throat, shingles, fungal irritation, fever blisters, boils, Plantar's warts, surgical procedures or vaginal lesions.

25. The method of claim 22, wherein the surface comprises a mucosal surface.

26. The method of claim 22, wherein the mucosal surface comprises the mouth, esophagus or larynx.

27. The method of claim 22, wherein the mucosal surface comprises the bronchial passages or nasal passages.

28. The method of claim 22, wherein the mucosal surface comprises the vagina or rectum/anus.

29. The method of claim 22, which comprises preventing or treating a hyperalgesic condition associated with burns, abrasions, bruises, contusions, frostbite, rashes, acne, insect bites/stings, skin ulcers, mucositis, inflammation, gingivitis, bronchitis, laryngitis, sore throat, shingles, fungal irritation, fever blisters, boils, Plantar's warts or vaginal lesions.

30. The method of claim 22, which comprises preventing or treating a hyperalgesic condition associated with a skin ulcer and the skin ulcer is selected from the group consisting of diabetic and decubitus ulcers.

31. The method of claim 22, which comprises preventing or treating a hyperalgesic condition associated with a fungal irritation and the fungal irritation is selected from the group consisting of athlete's foot and jock itch.

32. The method of claim 22, which comprises preventing or treating a hyperalgesic condition associated with a vaginal lesion and the vaginal lesion is associated with mycosis or sexually transmitted diseases.

33. The method of claim 18, wherein the compound is topically applied to a surface in the eyes, mouth, larynx, esophagus, bronchial, nasal passages, vagina or rectum/anus.

34. The method of claim 33, wherein the compound is applied to a surface in the eyes.

35. The method of claim 18, wherein the condition treated or prevented is a hyperalgesic condition associated with inflammation and the inflammation is selected from the group consisting of periodontal inflammation, orthodontic inflammation, inflammatory conjunctivitis, hemorrhoids and venereal inflammations.

36. The method of claim 18, which comprises preventing or treating a hyperalgesic condition associated with an abrasion and the abrasion comprises a corneal abrasion.

37. The method of claim 18, which comprises preventing or treating a hyperalgesic condition associated with post-surgery recovery.

38. The method of claim 37, wherein the surgery is selected from the group consisting of radial keratectomy, tooth extraction, lumpectomy, episiotomy, laparoscopy and arthroscopy.

39. The method of claim 18, wherein the hyperalgesia is a hyperalgesic condition associated with allergic dermatitis, contact dermatitis, skin ulcers, inflammation, rashes, fungal irritation and hyperalgesic conditions associated with infectious agents.

* * * * *

UNITED STATES PATENT AND TRADEMARK OFFICE
CERTIFICATE OF CORRECTION

PATENT NO. : 6,573,282 B1
DATED : June 3, 2003
INVENTOR(S) : Yaksh et al.

It is certified that error appears in the above-identified patent and that said Letters Patent is hereby corrected as shown below:

<u>Column 49,</u>
Line 19, replace "(" with -- [ --;

<u>Column 52,</u>
Lines 59-61, the equation should read as:
$$\text{Inhibition (\%)} = \frac{\text{Threshold of the treated group} - \text{Threshold of the control group}}{\text{Threshold of the control group}} \times 100$$

<u>Column 91,</u>
Lines 32-34, the equation should read as:
$$\frac{(\text{mean formalin response} - \text{mean saline response}) - \text{individual response}}{\text{mean formalin response} - \text{mean saline response}} \times 100$$

Signed and Sealed this

Second Day of December, 2003

JAMES E. ROGAN
*Director of the United States Patent and Trademark Office*